US008202857B2

(12) United States Patent
Claremon et al.

(10) Patent No.: US 8,202,857 B2
(45) Date of Patent: Jun. 19, 2012

(54) 1,3-OXAZEPAN-2-ONE AND 1,3-DIAZEPAN-2-ONE INHIBITORS OF 11β-HYDROXYSTEROID DEHYDROGENASE 1

(75) Inventors: David A. Claremon, Maple Glen, PA (US); Linghang Zhuang, Chalfont, PA (US); Colin M. Tice, Ambler, PA (US); Suresh B. Singh, Kendall Park, NJ (US); Yuanjie Ye, Ambler, PA (US); Wei Zhao, Eagleville, PA (US); Katerina Leftheris, Skillman, NJ (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 365 days.

(21) Appl. No.: 12/583,009

(22) Filed: Aug. 11, 2009

(65) Prior Publication Data
US 2010/0041637 A1 Feb. 18, 2010

Related U.S. Application Data

(63) Continuation-in-part of application No. PCT/US2009/000853, filed on Feb. 11, 2009.

(60) Provisional application No. 61/065,301, filed on Feb. 11, 2008.

(51) Int. Cl.
| | |
|---|---|
| C07D 265/10 | (2006.01) |
| C07D 413/04 | (2006.01) |
| C07D 413/06 | (2006.01) |
| C07D 413/10 | (2006.01) |
| C07D 413/14 | (2006.01) |
| C07D 417/04 | (2006.01) |
| C07D 417/06 | (2006.01) |
| C07D 417/10 | (2006.01) |
| C07D 417/14 | (2006.01) |
| A61K 31/55 | (2006.01) |
| A61K 31/553 | (2006.01) |
| A61P 3/06 | (2006.01) |

(52) U.S. Cl. ............... 514/211.03; 514/218; 540/488; 540/492

(58) Field of Classification Search .......... 540/488, 540/492; 514/211.03, 218
See application file for complete search history.

(56) References Cited

U.S. PATENT DOCUMENTS

| | | |
|---|---|---|
| 3,341,538 A | 9/1967 | Block et al. |
| 3,681,349 A | 8/1972 | Schwan et al. |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 7,026,310 B2 | 4/2006 | Emig et al. |
| 7,056,912 B2 | 6/2006 | Emig et al. |
| 7,132,551 B2 | 11/2006 | Aquila et al. |
| 7,186,844 B2 | 3/2007 | Ikemoto |

(Continued)

FOREIGN PATENT DOCUMENTS

DE 1801556 A1 5/1970

(Continued)

OTHER PUBLICATIONS

Database CA [Online], Chemical Abstracts Service, Fukushima et al., "Preparation of Imidazolidinone Derivatives as 11.beta.-HSD1 Inhibitors", 2007, XP 002531878.
Gavezzotti, "Are Crystal Structures Predicatble?", Accounts of Chemical Research, 1994, vol. 27, pp. 309-314.
Vippagunta, et al., "Crystalline Solids", Advanced Drug Deliver Reviews, 2001, vol. 48, pp. 3-26.
U.S. Appl. No. 12/670,205, filed Jul. 25, 2008, Vitae Pharmaceuticals, Inc.
U.S. Appl. No. 12/670,209, filed Jul. 25, 2008, Vitae Pharmaceuticals, Inc.

(Continued)

*Primary Examiner* — Bruck Kifle
(74) *Attorney, Agent, or Firm* — McCarter & English LLP

(57) ABSTRACT

This invention relates to novel compounds of the Formula (I), (I*), (I**), I, Ia, Ib, Ic, Id, Ie, If, Ig, $Il^{1-3}$, $Im^{1-3}$, $In^{1-3}$, or $Io^{1-2}$, pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds and methods for their use in the reduction or control of the production of cortisol in a cell or the inhibition of the conversion of cortisone to cortisol in a cell.

75 Claims, No Drawings

U.S. PATENT DOCUMENTS

| | | |
|---|---|---|
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0264650 A1 | 10/2009 | Cho et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0028445 A1 | 2/2011 | Eckhardt et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112082 A1 | 5/2011 | Claremon et al. |
| 2011/0124635 A1 | 5/2011 | Claremon et al. |
| 2011/0190262 A1 | 8/2011 | Himmelsbach et al. |
| 2011/0224242 A1 | 9/2011 | Giethlen et al. |

FOREIGN PATENT DOCUMENTS

| | | |
|---|---|---|
| DE | 19918725 A1 | 10/2000 |
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A1 | 3/1995 |
| EP | 0471591 B1 | 5/1995 |
| EP | 0928789 A1 | 7/1999 |
| EP | 1156049 A | 11/2001 |
| EP | 1270724 A2 | 1/2003 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |
| JP | 2007 254409 | 10/2007 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | WO 97/36605 | 10/1997 |
| WO | WO 98/57940 | 12/1998 |
| WO | WO 99/05125 | 2/1999 |
| WO | WO 99/06395 | 2/1999 |
| WO | WO 01/00595 A1 | 1/2001 |
| WO | WO 01/44200 A2 | 6/2001 |
| WO | WO 01/55063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | WO 2004/046137 A1 | 6/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | WO 2005/113525 A1 | 12/2005 |
| WO | WO 2006/003494 A2 | 1/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | WO 2006/104280 A | 10/2006 |
| WO | WO 2006/109056 A1 | 10/2006 |
| WO | WO 2007/008529 A2 | 1/2007 |
| WO | WO 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | WO 2007/109456 A2 | 9/2007 |
| WO | WO 2007/118185 A2 | 10/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |
| WO | WO 2008/000951 | 1/2008 |
| WO | WO 2008/031227 A1 | 3/2008 |
| WO | WO 2008/036715 A1 | 3/2008 |
| WO | WO 2008/046758 A | 4/2008 |
| WO | WO 2008/059948 A | 5/2008 |
| WO | WO 2008/106128 A | 9/2008 |
| WO | WO 2008/106128 A | 9/2008 |
| WO | WO 2008/118332 A2 | 10/2008 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |

| WO | WO 2009/102428 | 8/2009 |
| WO | WO 2009/102460 | 8/2009 |
| WO | WO 2009/117109 | 9/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | WO 2010/010149 | 1/2010 |
| WO | WO 2010/010150 A1 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | WO 2010/091067 | 8/2010 |
| WO | WO 2010/127237 | 11/2010 |

OTHER PUBLICATIONS

U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.
U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
International Search Report—(PCT/US2010/023021) Date of Mailing Aug. 5, 2010.
International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Surgery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Supression of the IGF-I System in Diabetic Wounds", Surgery, 2000, vol. 127, pp. 687-695.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract, (1968).
Chemica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract, (1978).
Zhurnal Organicheskoi Khimii, 1978, vol. 14(5), pp. 1092-1094.

Database CA [Online], Chemicals Abstracts Service, Fukushima et al., "Preparation of Imidazolidinone Derivatives as 11.beta.-HSD1 inhibitors", XP 002531878, (2007).
"Khimiia Elementoorganicheskikh Soedineni", 1982, vol. 1982 pp. 22-26.
"Zhurnal Organicheskol Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b. Saitkulova, et al., "Synthesis involving bromozinc alcoholates of carboxylic acid esters", p. 764 col. 1, XP002504064 abstract.
Goubet, et al., "Conversion of a Thiohydrantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid, IX", Journal Fuer Praktische Chemie, vol. 328, 1986, pp. 163-172, XP002504062 p. 164, compound 4j.
Schoellkopf, et al., "Umsetzungen Alphametallierter Isocyanide Mit Einigen 1,3-Dipolen/Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools"with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.

International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Coiumbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP00256894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.
U.S. Appl. No. 12/747,391, filed Nov. 11, 2010, Claremon et al.
U.S. Appl. No. 12/990,296, filed Mar. 1, 2011, Claremon et al.
U.S. Appl. No. 12/990,306, filed Jun. 6, 2011, Claremon et al.
U.S. Appl. No. 12/991,722, filed Jan. 5, 2011, Peters, Stefan.
U.S. Appl. No. 13/054,949, filed Feb. 23, 2011, Eckhardt et al.
U.S. Appl. No. 13/054,954, filed Jan. 20, 2011, Himmelsbach et al.
U.S. Appl. No. 13/059,233, filed Feb. 16, 2011, Eckhardt et al.
U.S. Appl. No. 13/124,259, filed May 17, 2011, Eckhardt et al.
U.S. Appl. No. 13/147,637, filed Aug. 3, 2011, Claremon et al.
U.S. Appl. No. 13/054,959, filed Feb. 23, 2011, Fandrick et al.
CA 154 : 284276.
CA 1267843-31-1.
Sullivan, John M. and Efner, Howard F., "The Preparation of 6-Aryltetrahydro-1,3-oxazin-2-ones and Their Hydrolysis to 3-Substituted Propylamines," *The Journal of Organic Chemistry*; 33 (5): 2134-2136 (1968).
Wolfling, Janos et al., "Neighboring Group Participation Part 15. Stereoselective Synthesis of Some Steroidal Tetrahydrooxaziin-2-ones, as Novel Presumed Inhibitors of Human 5α-Reductase," *Steroids*; 69: 451-460 (2004).

1,3-OXAZEPAN-2-ONE AND 1,3-DIAZEPAN-2-ONE INHIBITORS OF 11β-HYDROXYSTEROID DEHYDROGENASE 1

RELATED APPLICATIONS

This application is a continuation-in-part of International Application No. PCT/US2009/000853, which designated the United States and was filed on Feb. 11, 2009, published in English, which claims the benefit of U.S. Provisional Application No. 61/065,301, filed on Feb. 11, 2008. The entire teachings of the above applications are incorporated herein by reference.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Opthalmol. Vis. Sci. 41: 1629-1683; Rauz et al. (2001) Invest. Opthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11β-HSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043,951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts or prodrugs thereof, are effective inhibitors of 11β-HSD1. Formula I and its constituent members are defined herein as follows:

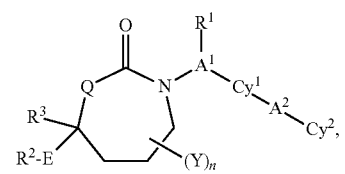

wherein $R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy or $(C_1-C_3)$alkoxy$(C_1-C_3)$alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, and $(C_1-C_3)$alkoxy$(C_1-C_3)$alkyl, wherein each is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$, $(R^4)_2NS(=O)_2O$, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, spirocycloalkyl; heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

Q is O or $NR^5$;

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

$R^5$ is H, $(C_1-C_6)$alkyl, halo$(C_1-C_6)$alkyl, or hydroxy$(C_1-C_6)$alkyl;

or a pharmaceutically acceptable salt, enantiomer or diastereomer thereof.

In another embodiment of the invention, Formula I and its constituent members are defined herein as follows:

$R^1$ is (a) absent or (b) is selected from $(C_1-C_6)$alkyl, $(C_2-C_6)$alkenyl, $(C_2-C_6)$alkynyl or $(C_1-C_3)$alkoxy$(C_1-C_3)$alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo $(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$R^3$ is selected from $(C_1-C_6)$alkyl, $(C_2-C_6)$alkenyl, $(C_2-C_6)$alkynyl and $(C_1-C_3)$alkoxy$(C_1-C_3)$alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4)_2NC(=O)NR^4-$, $R^4OC(=O)NR^4$, $(R^4)_2NC(=NCN)NR^4$, $(R^4O)_2P(=O)O-$, $(R^4O)_2P(=O)NR^4-$, $R^4OS(=O)_2NR^4$, $(R^4)_2NS(=O)_2O$, $(R^4)_2NS(=O)_2NR^4$, $R^4S(=O)_2NR^4-$, $R^4S(=O)_2NHC(=O)-$, $R^4S(=O)_2NHC(=O)O-$, $R^4S(=O)_2NHC(=O)NR^4$, $R^4OS(=O)_2NHC(=O)-$, $R^4OS(=O)_2NHC(=O)O-$, $R^4OS(=O)_2NHC(=O)NR^4$, $(R^4)_2NS(=O)_2NHC(=O)-$, $(R^4)_2NS(=O)_2NHC(=O)O-$, $(R^4)_2NS(=O)_2NHC(=O)NR^4$, $R^4C(=O)NHS(=O)_2-$, $R^4C(=O)NHS(=O)_2O-$, $R^4C(=O)NHS(=O)_2NR^4$, $R^4OC(=O)NHS(=O)_2-$, $R^4OC(=O)NHS(=O)_2O-$, $R^4OC(=O)NHS(=O)_2NR^4$, $(R^4)_2NC(=O)NHS(=O)_2-$, $(R^4)_2NC(=O)NHS(=O)_2O-$, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

Q is O or $NR^5$;

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl; and $R^5$ is H, $(C_1-C_6)$alkyl, halo$(C_1-C_6)$alkyl, or hydroxy$(C_1-C_6)$alkyl;

or a pharmaceutically acceptable salt, enantiomer or diastereomer thereof.

Another embodiment is a pharmaceutical composition comprising: i) a pharmaceutically acceptable carrier or diluent; and ii) compound of Formulas I, I*, I**, Ia, Ib, Ic, Id, Ie, If, Ig, Il$^{1-3}$, Im$^{1-3}$, In$^{1-3}$, or Io$^{1-2}$; or a pharmaceutically acceptable salt, enantiomer or diastereomer thereof Another embodiment of the invention is a method of inhibiting 11β-HSD1 activity comprising the step of administering to a mammal in need of such treatment an effective amount of a compound of Formulas I, I*, I**, Ia, Ib, Ic, Id, Ie, If, Ig, Il$^{1-3}$, Im$^{1-3}$, In$^{1-3}$, or Io$^{1-2}$ or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas I, I*, I**, Ia, Ib, Ic, Id, Ie, If, Ig, Il$^{1-3}$, Im$^{1-3}$, In$^{1-3}$, or Io$^{1-2}$ or a pharmaceutically acceptable, enantiomer or diastereomer thereof.

Another embodiment of the invention is the use of a compound of Formulas I, I*, I**, Ia, Ib, Ic, Id, Ie, If, Ig, Il$^{1-3}$, Im$^{1-3}$, In$^{1-3}$, or Io$^{1-2}$ or a pharmaceutically acceptable salt, enantiomer or diastereomer thereof for the manufacture of a medicament for inhibiting 11β-HSD1 activity in a mammal in need of such treatment.

Another embodiment of the invention is the use of a compound of Formulas I, I*, I**, Ia, Ib, Ic, Id, Ie, If, Ig, Il$^{1-3}$, Im$^{1-3}$, In$^{1-3}$, or Io$^{1-2}$ or a pharmaceutically acceptable salt, enantiomer or diastereomer thereof for the manufacture of a medicament for treating a subject with a disease associated with the activity or expression of 11β-HSD1.

Another embodiment of the invention is a compound of Formulas I, I*, I**, Ia, Ib, Ic, Id, Ie, If, Ig, Il$^{1-3}$, Im$^{1-3}$, In$^{1-3}$, or Io$^{1-2}$ or a pharmaceutically acceptable salt, enantiomer or diastereomer thereof for use in inhibiting 11β-HSD1 activity in a mammal in need of such treatment.

Another embodiment of the invention is a compound of Formulas I, I*, I**, Ia, Ib, Ic, Id, Ie, If, Ig, Il$^{1-3}$, Im$^{1-3}$, In$^{1-3}$, or Io$^{1-2}$ or a pharmaceutically acceptable salt, enantiomer or diastereomer thereof for use in for treating a subject with a disease associated with the activity or expression of 11β-HSD1.

The present invention further provides methods of inhibiting 11β-HSD1 by contacting 11β-HSD1 with a compound of Formula I, I*, I**, Ia, Ib, Ic, Id, Ie, If, Ig, Il$^{1-3}$, Im$^{1-3}$, In$^{1-3}$, or Io$^{1-2}$ of the invention.

The present invention further provides methods of inhibiting or reducing the conversion of cortisone to cortisol in a cell using a compound of Formula I, I*, I**, Ia, Ib, Ic, Id, Ie, If, Ig, Il$^{1-3}$, Im$^{1-3}$, In$^{1-3}$, or Io$^{1-2}$ of the invention.

The present invention further provides methods of inhibiting or reducing production of cortisol in a cell using a compound of Formula I, I*, I**, Ia, Ib, Ic, Id, Ie, If, Ig, Il$^{1-3}$, Im$^{1-3}$, In$^{1-3}$, or Io$^{1-2}$ of the invention.

The present invention further provides methods of increasing insulin sensitivity in a subject in need thereof using a compound of Formula I, I*, I**, Ia, Ib, Ic, Id, Ie, If, Ig, Il$^{1-3}$, Im$^{1-3}$, In$^{1-3}$, or Io$^{1-2}$ of the invention.

DETAILED DESCRIPTION OF THE INVENTION

A first embodiment is a compound of Structural Formula I, wherein $R^3$ is selected from substituted $(C_1-C_6)$alkyl, or optionally substituted $(C_2-C_6)$alkenyl, optionally substituted $(C_2-C_6)$alkynyl and optionally substituted $(C_1-C_3)$alkoxy$(C_2-C_3)$alkyl, wherein each substituted group represented by $R^3$ has up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$, $(R^4)_2NS(=O)_2O$, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

and the remaining values are as defined for Formula I above or a pharmaceutically acceptable salt, enantiomer or diastereomer thereof.

A second embodiment is a compound of Structural Formula I, wherein $R^2$ is aryl, heteroaryl, cycloalkyl or heterocyclyl, wherein each 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo ($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

$R^3$ is selected from substituted ($C_1$-$C_6$)alkyl, or optionally substituted ($C_2$-$C_6$)alkenyl, optionally substituted ($C_2$-$C_6$)alkynyl and optionally substituted ($C_1$-$C_3$)alkoxy($C_2$-$C_3$)alkyl, wherein each substituted group represented by $R^3$ has up to four groups independently selected from cyano, $R^4$, $(R^4)_2N$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$, $(R^4)_2NS(=O)_2$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

and the remaining values are as defined for Formula I above or a pharmaceutically acceptable salt, enantiomer or diastereomer thereof.

In a third embodiment, the variables in Formula (I) are as defined in the first or second embodiment, provided that the substituents for the aryl, heteroaryl, monocyclic cycloalkyl and monocyclic heterocyclyl group represented by $Cy^1$ can additionally be selected from ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl)}{($C_1$-$C_6$)alkyl}aminocarbonyl($C_1$-$C_6$)alkyl and di($C_3$-$C_6$)cycloalkylaminocarbonyl($C_1$-$C_6$)alkyl;

the substituents for the aryl, heteroaryl, cycloalkyl and heterocyclyl group represented by $Cy^2$ can additionally be selected from ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl; and the substituents for the aryl, heteroaryl, cycloalkyl and heterocyclyl group represented by $R^2$ can additionally be selected from ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl.

A fourth embodiment is a compound of Structural Formula II:

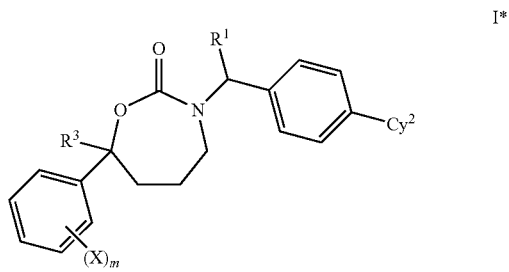

wherein $R^1$ is ($C_1$-$C_6$)alkyl, optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$Cy^2$ is aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)

cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylthio, (C₄-C₇)cycloalkylalkylthio, halo(C₁-C₆)alkylthio, halo(C₃-C₆)cycloalkylthio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylamino-sulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl;

Substituents X are independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylthio, (C₄-C₇)cycloalkylalkylthio, halo(C₁-C₆)alkylthio, halo(C₃-C₆)cycloalkylthio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl;

m is 0, 1, 2, 3, 4;

R³ is (C₁-C₆)alkyl substituted by up to four groups independently selected from cyano, oxo, HO—, (R⁴)₂N—, R⁴O₂C—, R⁴S, R⁴S(=O)—, R⁴S(=O)₂—, R⁴C(=O)NR⁴, (R⁴)₂NC(=O)—, (R⁴)₂NC(=O)O—, (R⁴)₂NC(=O)NR⁴—, R⁴OC(=O)NR⁴—, (R⁴)₂NC(=NCN)NR⁴, (R⁴O)₂P(=O)O—, (R⁴O)₂P(=O)NR⁴—, R⁴OS(=O)₂NR⁴—, (R⁴)₂NS(=O)₂O—, (R⁴)₂NS(=O)₂NR⁴, R⁴S(=O)₂NR⁴—, R⁴S(=O)₂NHC(=O)—, R⁴S(=O)₂NHC(=O)O—, R⁴S(=O)₂NHC(=O)NR⁴, R⁴OS(=O)₂NHC(=O)—, R⁴OS(=O)₂NHC(=O)O—, R⁴OS(=O)₂NHC(=O)NR⁴, (R⁴)₂NS(=O)₂NHC(=O)—, (R⁴)₂NS(=O)₂NHC(=O)O—, (R⁴)₂NS(=O)₂NHC(=O)NR⁴, R⁴C(=O)NHS(=O)₂—, R⁴C(=O)NHS(=O)₂O—, R⁴C(=O)NHS(=O)₂NR⁴, R⁴OC(=O)NHS(=O)₂—, R⁴OC(=O)NHS(=O)₂O—, R⁴OC(=O)NHS(=O)₂NR⁴, (R⁴)₂NC(=O)NHS(=O)₂—, (R⁴)₂NC(=O)NHS(=O)₂O—, (R⁴)₂NC(=O)NHS(=O)₂NR⁴, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, CO₂H, CONH₂, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, CO₂H, CONH₂, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, CO₂H, CONH₂, N-monoalkyl-substituted amido, N,N-dialkyl-substituted amido, or oxo);

or a pharmaceutically acceptable salt, enantiomer or diastereomer thereof.

In another embodiment, m is 1, 2, or 3 in Structural Formula I* and the remaining values are as described above.

A fifth embodiment is a compound of Structural Formula I**:

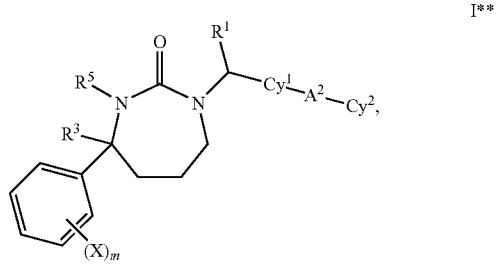

wherein

R¹ is (C₁-C₆)alkyl, optionally substituted with up to four groups independently selected from fluorine, cyano, oxo, R⁴, R⁴O—, (R⁴)₂N—, R⁴O₂C—, R⁴S, R⁴S(=O)—, R⁴S(=O)₂—, R⁴C(=O)NR⁴—, (R⁴)₂NC(=O)—, (R⁴)₂NC(=O)O—, (R⁴)₂NC(=O)NR⁴—, R⁴OC(=O)NR⁴—, (R⁴)₂NC(=NCN)NR⁴—, (R⁴O)₂P(=O)O—, (R⁴O)₂P(=O)NR⁴—, R⁴OS(=O)₂NR⁴—, (R⁴)₂NS(=O)₂O—, (R⁴)₂NS(=O)₂NR⁴—, R⁴S(=O)₂NR⁴—, R⁴S(=O)₂NHC(=O)—, R⁴S(=O)₂NHC(=O)O—, R⁴S(=O)₂NHC(=O)NR⁴—, R⁴OS(=O)₂NHC(=O)—, R⁴OS(=O)₂NHC(=O)O—, R⁴OS(=O)₂NHC(=O)NR⁴—, (R⁴)₂NS(=O)₂NHC(=O)—, (R⁴)₂NS(=O)₂NHC(=O)O—, (R⁴)₂NS(=O)₂NHC(=O)NR⁴—, R⁴C(=O)NHS(=O)₂—, R⁴C(=O)NHS(=O)₂O—, R⁴C(=O)NHS(=O)₂NR⁴—, R⁴OC(=O)

NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, aryl, cycloalkyl, heterocyclyl, heteroaryl, arylamino and heteroarylamino;

Cy$^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylthio, (C$_4$-C$_7$)cycloalkylalkylthio, halo(C$_1$-C$_6$)alkylthio, halo(C$_3$-C$_6$)cycloalkylthio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl and (C$_1$-C$_6$)alkylcarbonyl;

A$^2$ is a bond;

Cy$^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylthio, (C$_4$-C$_7$)cycloalkylalkylthio, halo(C$_1$-C$_6$)alkylthio, halo(C$_3$-C$_6$)cycloalkylthio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl and (C$_1$-C$_6$)alkylcarbonyl;

Substituents X are independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylthio, (C$_4$-C$_7$)cycloalkylalkylthio, halo(C$_1$-C$_6$)alkylthio, halo(C$_3$-C$_6$)cycloalkylthio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl and (C$_1$-C$_6$)alkylcarbonyl;

m is 0, 1, 2, 3, 4;

R$^3$ is selected from (C$_1$-C$_6$)alkyl substituted with up to four groups independently selected from cyano, oxo, R$^4$, HO—, (R$^4$)$_2$N—, R$^4$O$_2$C—, R$^4$S, R$^4$S(=O)—, R$^4$S(=O)$_2$—, R$^4$C(=O)NR$^4$, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$, (R$^4$O)$_2$P(=O)O—, (R$^4$O)$_2$P(=O)NR$^4$—, R$^4$OS(=O)$_2$NR$^4$, (R$^4$)$_2$NS(=O)$_2$O, (R$^4$)$_2$NS(=O)$_2$NR$^4$, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$, R$^4$OS(=O)$_2$NHC(=O)—, R$^4$OS(=O)$_2$NHC(=O)O—, R$^4$OS(=O)$_2$NHC(=O)NR$^4$, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$, R$^4$C(=O)NHS(=O)$_2$—, R$^4$C(=O)NHS(=O)$_2$O—, R$^4$C(=O)NHS(=O)$_2$NR$^4$, R$^4$OC(=O)NHS(=O)$_2$—, R$^4$OC(=O)NHS(=O)$_2$O—, R$^4$OC(=O)NHS(=O)$_2$NR$^4$, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);
or a pharmaceutically acceptable salt, enantiomer or diastereomer thereof.

In another embodiment, m is 1, 2, or 3 in Structural Formula I* and the remaining values are as described above.

A sixth embodiment is a compound of Formula I, I*, I** or any one of Formulas Ia-g wherein:
$R^1$ (for Formulas I, I*, I** and Id) is absent or is methyl or ethyl;
$A^1$ (for Formulas I, I*, I** and Id) is a bond or $CH_2$ or if $R^1$ is present, then $A^1$ is CH;
$Cy^1$ (for Formulas I, I*, I** and Ia-e) is phenyl, cyclopropyl, cyclohexyl, pyrrolidinyl, pyridyl, N-oxo-pyridyl, thiazolyl or pyrimidinyl optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;
$A^2$ (for Formulas I, I*, I** and Ia-e) is a bond, O, $OCH_2CO$ or C=O;
$Cy^2$ (for Formulas I, I*, I** and Ia-e) is (a) hydrogen or (b) phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl) aminocarbonyl, acetylamino-methyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;
n (for Formula I) is 0;
E (for Formulas I, Ia-c and Ie-g) is a bond or $CH_2$;
$R^2$ (for Formulas I, Ia-c and Ie-g) is isopropyl, thienyl, phenyl, or pyridyl, each optionally substituted with halo, methyl, methylthio or (4-morpholino)methyl;
$R^3$ (for Formulas I, I*, I**, and Ia-g) is methyl, ethyl, propyl, butyl, vinyl, allyl or ethoxyethyl, each optionally substituted with up to two groups independently selected from HO—, MeO—, $H_2N$—, MeC(=O)NH—, MeS(=O)$_2$NH—, $H_2NC$(=O)—, MeNHC(=O)—, $HO_2C$—, $(HO)_2P$(=O)O—, $H_2NS$(=O)$_2$O—, $H_2NS$(=O)$_2$NH—, MeNHC(=O)NH—, MeNHC(=O)O—, oxo, cyano, $HO_2C$—, $HOCH_2CH_2NH$—, 4-morpholino, $HOCH_2C$(=O)NH—, $H_2NCH_2C$(=O)NH—, EtNHC(=O)NH, MeOC(=O)NH—, MeNHC(=NC≡N)NH—, Me-, MeS—, $MeSO_2$— $MeSO_2N(Me)$-, MeS(=O)$_2$NHC(=O)—, imidazolylamino-, imidazolyl, tetrazolyl, $H_2NCONH$—, $H_2NCO_2$—, $HOCH_2CH_2O$—, MeNH—, $Me_2N$— and MeCONMe;
Q (Formulas I and Ia-g) is O or $NR^5$;
$R^5$ (Formulas I, I*, I**, and Ia-g) is hydrogen or methyl;
or a pharmaceutically acceptable salt, enantiomer or diastereomer thereof.

A seventh embodiment is a compound of Formula Ia:

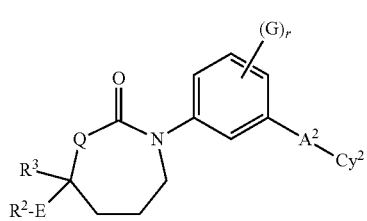

wherein $A^2$, $Cy^2$, E, Q, $R^2$, $R^3$, and $R^5$ are as defined for Formula I above; r is 0, 1, 2, 3 or 4; and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl or $(C_1-C_6)$alkylcarbonyl;
or a pharmaceutically acceptable salt, enantiomer or diastereomer thereof.

An eighth embodiment is a compound of Formula Ib:

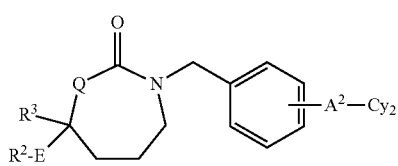

wherein $A^2$, $Cy^2$, Q, E, $R^2$, $R^3$ and $R^5$ are as defined for Formula I above;
or a pharmaceutically acceptable salt, enantiomer or diastereomer thereof.

A ninth embodiment is a compound of Formula Ic:

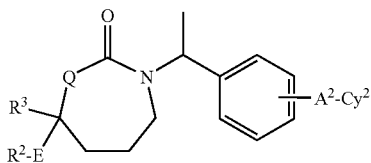

wherein $A^2$, $Cy^2$, E, Q, $R^2$, $R^3$ and $R^5$ are as defined for Formula I above;
or a pharmaceutically acceptable salt, enantiomer or diastereomer thereof.

A tenth embodiment is a compound of Formula Id:

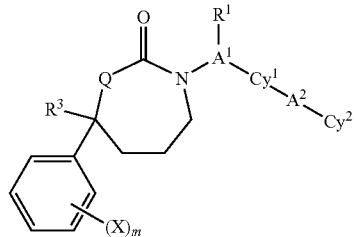

wherein $A^1$, $R^1$, $Cy^1$, $A^2$, $Cy^2$, Q, $R^3$, and $R^5$ are as defined for Formula I above; m is 0, 1, 2, 3 or 4; and substituents X are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

or a pharmaceutically acceptable salt, enantiomer or diastereomer thereof. In a specific embodiment, $A^2$-$Cy^2$ is meta or para to the carbon atom bonded to -$A_1$.

An eleventh embodiment is a compound of Formula Ie:

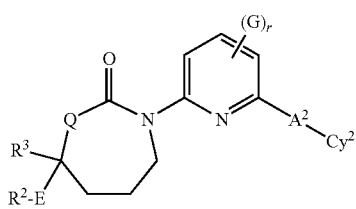

wherein $A^2$, $Cy^2$, E, Q, $R^2$, $R^3$, and $R^5$ are as defined for Formula I above, r is 0, 1, 2, 3 or 4; and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

or a pharmaceutically acceptable salt, enantiomer or diastereomer thereof.

A twelfth embodiment is a compound of Formula If:

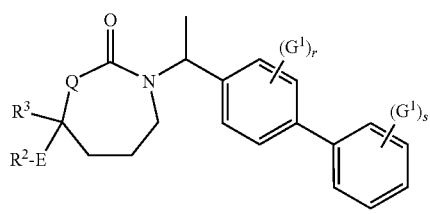

wherein E, Q, $R^2$, $R^3$, and $R^5$ are as defined for Formula I above, r and s are independently 0, 1, 2, 3 or 4; and $G^1$ and $G^2$ are independently selected from fluorine, chlorine, bromine, iodine, cyano, nitro, amino, hydroxy, carboxy, $(C_1\text{-}C_6)$alkyl, hydroxy$(C_1\text{-}C_6)$alkyl, $(C_3\text{-}C_6)$cycloalkyl, hydroxy$(C_3\text{-}C_6)$cycloalkyl, $(C_4\text{-}C_7)$cycloalkylalkyl, $(C_2\text{-}C_6)$alkenyl, halo$(C_2\text{-}C_6)$alkenyl, hydroxy$(C_2\text{-}C_6)$alkenyl, $(C_2\text{-}C_6)$alkynyl, $(C_3\text{-}C_6)$cycloalkyl$(C_2\text{-}C_4)$alkynyl, halo$(C_1\text{-}C_6)$alkyl, halo$(C_3\text{-}C_6)$cycloalkyl, halo$(C_4\text{-}C_7)$cycloalkylalkyl, $(C_1\text{-}C_6)$alkoxy, $(C_3\text{-}C_6)$cycloalkoxy, $(C_4\text{-}C_7)$cycloalkylalkoxy, halo$(C_1\text{-}C_6)$alkoxy, halo$(C_3\text{-}C_6)$cycloalkoxy, halo$(C_4\text{-}C_7)$cycloalkylalkoxy, $(C_1\text{-}C_6)$alkylthio, $(C_3\text{-}C_6)$cycloalkylthio, $(C_4\text{-}C_7)$cycloalkylalkylthio, halo$(C_1\text{-}C_6)$alkylthio, halo$(C_3\text{-}C_6)$cycloalkylthio, halo$(C_4\text{-}C_7)$cycloalkylalkylthio, $(C_1\text{-}C_6)$alkanesulfinyl, $(C_3\text{-}C_6)$cycloalkanesulfinyl, $(C_4\text{-}C_7)$cycloalkylalkanesulfinyl, halo$(C_1\text{-}C_6)$alkanesulfinyl, halo$(C_3\text{-}C_6)$cycloalkanesulfinyl, halo$(C_4\text{-}C_7)$cycloalkylalkanesulfinyl, $(C_1\text{-}C_6)$alkanesulfonyl, $(C_3\text{-}C_6)$cycloalkanesulfonyl, $(C_4\text{-}C_7)$cycloalkylalkanesulfonyl, halo$(C_1\text{-}C_6)$alkanesulfonyl, halo$(C_3\text{-}C_6)$cycloalkanesulfonyl, halo$(C_4\text{-}C_7)$cyclo-alkylalkanesulfonyl, $(C_1\text{-}C_6)$alkylamino, di$(C_1\text{-}C_6)$alkylamino, $(C_1\text{-}C_6)$alkoxy$(C_1\text{-}C_6)$alkoxy, halo$(C_1\text{-}C_6)$alkoxy$(C_1\text{-}C_6)$alkoxy, $(C_1\text{-}C_6)$alkoxycarbonyl, $H_2NCO$, $H_2NSO_2$, $(C_1\text{-}C_6)$alkylaminocarbonyl, di$(C_1\text{-}C_6)$alkylaminocarbonyl, $(C_1\text{-}C_3)$alkoxy$(C_1\text{-}C_3)$alkylaminocarbonyl, heterocyclylcarbonyl, $(C_1\text{-}C_6)$alkylaminosulfonyl, di$(C_1\text{-}C_6)$alkylaminosulfonyl, heterocyclsulfonyl, $(C_1\text{-}C_6)$alkylcarbonylamino, $(C_1\text{-}C_6)$alkylcarbonylamino$(C_1\text{-}C_6)$alkyl, $(C_1\text{-}C_6)$alkylsulfonylamino, $(C_1\text{-}C_6)$alkylsulfonylamino$(C_1\text{-}C_6)$alkyl, $(C_1\text{-}C_6)$alkoxycarbonyl$(C_1\text{-}C_6)$alkoxy, $(C_1\text{-}C_6)$alkoxy$(C_1\text{-}C_6)$alkyl, halo$(C_1\text{-}C_6)$alkoxy$(C_1\text{-}C_6)$alkyl, hydroxy$(C_1\text{-}C_6)$alkoxy, heteroaryl, amino$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$alkyl, amino$(C_2\text{-}C_6)$alkoxy, $(C_1\text{-}C_6)$alkylamino$(C_2\text{-}C_6)$alkoxy, di$(C_1\text{-}C_6)$alkylamino$(C_2\text{-}C_6)$alkoxyl and $(C_1\text{-}C_6)$alkylcarbonyl;

or a pharmaceutically acceptable salt, enantiomer or diastereomer thereof.

A thirteenth embodiment is a compound of Formula Ig:

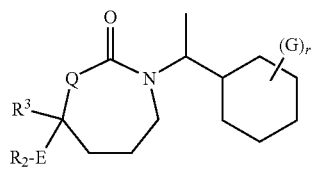

Ig wherein E, Q, $R^2$, $R^3$ and $R^5$ are as defined for Formula I above, r is 0, 1, 2, 3 or 4; and substituents G are independently selected from fluorine, chlorine, bromine, iodine, cyano, nitro, amino, hydroxy, carboxy, $(C_1\text{-}C_6)$alkyl, hydroxy$(C_1\text{-}C_6)$alkyl, $(C_3\text{-}C_6)$cycloalkyl, hydroxy$(C_3\text{-}C_6)$cycloalkyl, $(C_4\text{-}C_7)$cycloalkylalkyl, $(C_2\text{-}C_6)$alkenyl, halo$(C_2\text{-}C_6)$alkenyl, hydroxy$(C_2\text{-}C_6)$alkenyl, $(C_2\text{-}C_6)$alkynyl, $(C_3\text{-}C_6)$cycloalkyl$(C_2\text{-}C_4)$alkynyl, halo$(C_1\text{-}C_6)$alkyl, halo$(C_3\text{-}C_6)$cycloalkyl, halo$(C_4\text{-}C_7)$cycloalkylalkyl, $(C_1\text{-}C_6)$alkoxy, $(C_3\text{-}C_6)$cycloalkoxy, $(C_4\text{-}C_7)$cycloalkylalkoxy, halo$(C_1\text{-}C_6)$alkoxy, halo$(C_3\text{-}C_6)$cycloalkoxy, halo$(C_4\text{-}C_7)$cycloalkylalkoxy, $(C_1\text{-}C_6)$alkylthio, $(C_3\text{-}C_6)$cycloalkylthio, $(C_4\text{-}C_7)$cycloalkylalkylthio, halo$(C_1\text{-}C_6)$alkylthio, halo$(C_3\text{-}C_6)$cycloalkylthio, halo$(C_4\text{-}C_7)$cycloalkylalkylthio, $(C_1\text{-}C_6)$alkanesulfinyl, $(C_3\text{-}C_6)$cycloalkanesulfinyl, $(C_4\text{-}C_7)$cycloalkylalkanesulfinyl, halo$(C_1\text{-}C_6)$alkanesulfinyl, halo$(C_3\text{-}C_6)$cycloalkanesulfinyl, halo$(C_4\text{-}C_7)$cycloalkylalkanesulfinyl, $(C_1\text{-}C_6)$alkanesulfonyl, $(C_3\text{-}C_6)$cycloalkanesulfonyl, $(C_4\text{-}C_7)$cycloalkylalkanesulfonyl, halo$(C_1\text{-}C_6)$alkanesulfonyl, halo$(C_3\text{-}C_6)$cycloalkanesulfonyl, halo$(C_4\text{-}C_7)$cyclo-alkylalkanesulfonyl, $(C_1\text{-}C_6)$alkylamino, di$(C_1\text{-}C_6)$alkylamino, $(C_1\text{-}C_6)$alkoxy$(C_1\text{-}C_6)$alkoxy, halo$(C_1\text{-}C_6)$alkoxy$(C_1\text{-}C_6)$alkoxy, $(C_1\text{-}C_6)$alkoxycarbonyl, $H_2NCO$, $H_2NSO_2$, $(C_1\text{-}C_6)$alkylaminocarbonyl, di$(C_1\text{-}C_6)$alkylaminocarbonyl, $(C_1\text{-}C_3)$alkoxy$(C_1\text{-}C_3)$alkyl-aminocarbonyl, heterocyclylcarbonyl, $(C_1\text{-}C_6)$alkylaminosulfonyl, di$(C_1\text{-}C_6)$alkylaminosulfonyl, heterocyclsulfonyl, $(C_1\text{-}C_6)$alkylcarbonylamino, $(C_1\text{-}C_6)$alkylcarbonylamino$(C_1\text{-}C_6)$alkyl, $(C_1\text{-}C_6)$alkylsulfonylamino, $(C_1\text{-}C_6)$alkylsulfonylamino$(C_1\text{-}C_6)$alkyl, $(C_1\text{-}C_6)$alkoxycarbonyl$(C_1\text{-}C_6)$alkoxy, $(C_1\text{-}C_6)$alkoxy$(C_1\text{-}C_6)$alkyl, halo$(C_1\text{-}C_6)$alkoxy$(C_1\text{-}C_6)$alkyl, hydroxy$(C_1\text{-}C_6)$alkoxy, heteroaryl, amino$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$alkyl, amino$(C_2\text{-}C_6)$alkoxy, $(C_1\text{-}C_6)$alkylamino$(C_2\text{-}C_6)$alkoxy, di$(C_1\text{-}C_6)$alkylamino$(C_2\text{-}C_6)$alkoxyl and $(C_1\text{-}C_6)$alkylcarbonyl;

or a pharmaceutically acceptable salt, enantiomer or diastereomer thereof.

Another embodiment of the invention is a compound of any one of Formulas $II^{1-3}$ or a pharmaceutically acceptable salt, enantiomer or diastereomer thereof:

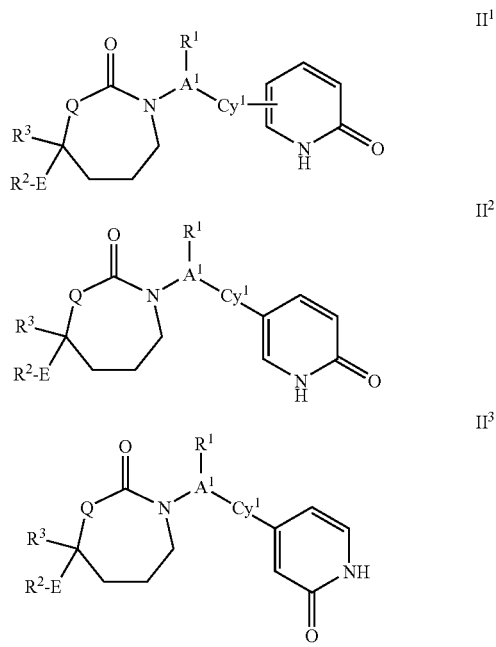

In Formulas $II^{1-3}$, the oxodihydropyridyl ring in Formulas $II^{1-3}$ are optionally substituted (substitution at ring carbons bonded to hydrogen and ring nitrogen atoms bonded to hydrogen atoms are encompassed, i.e., a "substitutable ring nitrogen atom") with up to four substituents as described above for $Cy^2$. Suitable substituents for $Cy^2$ and suitable values for Q, $R^1$, $R^2$, $R^3$, $A^1$, $Cy^1$ and E are as defined in any one of the first through twelfth embodiments. Alternatively, suitable substituents for $Cy^1$ and the oxodihydropyridyl ring in Formulas $II^{1-3}$ are as described for $G^1$ and $G^2$, respectively, in Formula If, and values for $R^1$, $R^2$, $R^3$, $A^1$, $Cy^1$ and E are as defined in any one of the first, second, third or fourth embodiments. Alternatively, suitable substituents for $Cy^1$ include $(C_1\text{-}C_4)$alkyl, $(C_1\text{-}C_4)$alkoxy, $(C_1\text{-}C_4)$haloalkyl, $(C_1\text{-}C_4)$haloalkoxy, halogen, cyano and nitro; suitable substituents for a substitutable ring nitrogen atom in the oxodihydropyridyl ring in Formulas $Il^{1-3}$ include $(C_1-C_4)$alkyl, $(C_3-C_4)$cycloalkyl, $(C_3-C_4)$cycloalkyl$(C_1-C_2)$alkyl, and $(C_1-C_4)$haloalkyl; suitable substituents for a ring carbon atom in the oxodihydropyridyl ring in Formulas $Il^{1-3}$ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino; and suitable values for $R^1$, $R^2$, $R^3$, $A^1$, $Cy^1$ and E are as defined in any one of the first, second, third or fourth embodiments.

For each of the embodiments described in the previous paragraph, Q is O or NH.

For each of the embodiments described in the paragraph immediately following Formulas $Il^{1-3}$, Q is O or NH and; $R^1$ is preferably methyl or ethyl.

For each of the embodiments described in the paragraph immediately following Formulas $Il^{1-3}$, Q is O or NH and; $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Il^{1-3}$, Q is O or NH and; $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Il^{1-3}$, Q is O or NH and; $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl, and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Il^{1-3}$, Q is O or NH and; $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl, and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Il^{1-3}$, Q is O or NH and; $R^1$ is preferably methyl or ethyl; and $R^3$ is 2-hydroxy-2-methylpropyl or 2-cyano-2-methylpropyl.

For each of the embodiments described in the paragraph immediately following Formulas $Il^{1-3}$, Q is O or NH and; $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $Il^{1-3}$, Q is O or NH and; $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl ring in Formulas $Il^{1-3}$ is $(C_1-C_4)$alkyl, $(C_3-C_4)$cycloalkyl, $(C_3-C_4)$cycloalkyl$(C_1-C_2)$alkyl, or $(C_1-C_2)$haloalkyl; and one or two ring carbon atoms in the oxodihydropyridyl ring in Formulas $Il^{1-3}$ are optionally substituted with methyl or ethyl.

Another embodiment of the invention is a compound of any one of Formulas $Im^{1-3}$, or a pharmaceutically acceptable salt, enantiomer or diastereomer thereof:

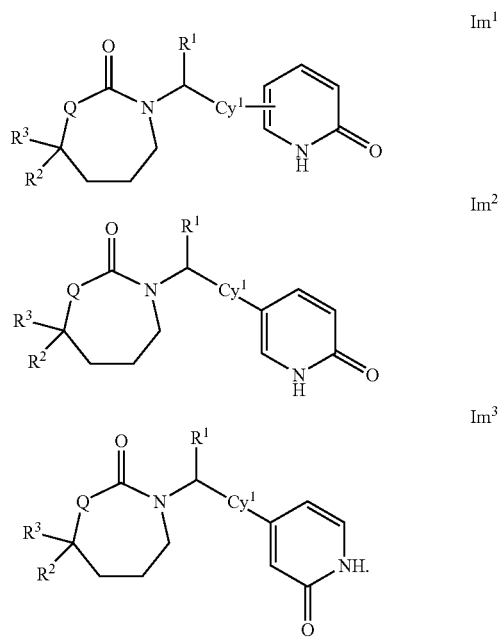

In Formulas $Im^{1-3}$, the oxodihydropyridyl ring are optionally substituted (substitution at ring carbons bonded to hydrogen and at nitrogen atoms bonded to hydrogen atoms are encompassed, i.e., a "substitutable ring nitrogen atom") with up to four substituents as described above for $Cy^2$. Suitable substituents for $Cy^2$ and suitable values for Q, $R^1$, $R^2$, $R^3$ and $Cy^1$ are as defined in any one of the first through twelfth embodiments. Alternatively, suitable substituents for $Cy^1$ and the oxodihydropyridyl ring in Formulas $Im^{1-3}$ are as described for $G^1$ and $G^2$, respectively, in Formula If, and values for $R^1$, $R^2$, $R^3$ and $Cy^1$ are as defined in any one of the first, second, third or fourth embodiments. Alternatively, suitable substituents for $Cy^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl ring in Formulas $Im^{1-3}$ include $(C_1-C_4)$alkyl, $(C_3-C_4)$cycloalkyl, $(C_3-C_4)$cycloalkyl$(C_1-C_2)$alkyl and $(C_1-C_4)$haloalkyl; suitable substituents for a ring carbon atom in the oxodihydropyridyl ring in Formulas $Im^{1-3}$ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino; and suitable values for $R^1$, $R^2$, $R^3$ and $Cy^1$ are as defined in any one of the first, second, third or fourth embodiments.

For each of the embodiments described in the previous paragraph, Q is O or NH.

For each of the embodiments described in the paragraph immediately following Formulas $Im^{1-3}$, Q is O or NH and; $R^1$ is preferably methyl or ethyl.

For each of the embodiments described in the paragraph immediately following Formulas $Im^{1-3}$, Q is O or NH and; $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Im^{1-3}$, Q is O or NH and; $R^1$ is preferably methyl or ethyl; and $R^3$ is $H_2NC(=O)$ $CMe_2CH_2$, 3-hydroxy-3-methylbutyl, 2-hydroxy-2-methylpropyl or 2-cyano-2-methylpropyl.

For each of the embodiments described in the paragraph immediately following Formulas $Im^{1-3}$, Q is O or NH and; $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Im^{1-3}$, Q is O or NH and; $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Im^{1-3}$, Q is O or NH and; $R^1$ is preferably methyl or ethyl; and $R^3$ is 2-hydroxy-2-methylpropyl or 2-cyano-2-methylpropyl.

For each of the embodiments described in the paragraph immediately following Formulas $Im^{1-3}$, Q is O or NH and; $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $Im^{1-3}$, Q is O or NH and; $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl ring in Formulas $Im^{1-3}$ is $(C_1-C_4)$alkyl, $(C_3-C_4)$cycloalkyl, $(C_3-C_4)$cycloalkyl$(C_1-C_2)$alkyl, or $(C_1-C_2)$haloalkyl; and one or two ring carbon atoms in the oxodihydropyridyl ring in Formulas $Im^{1-3}$ are optionally substituted with methyl or ethyl.

Another embodiment of the invention is a compound of any one for Formulas $In^{1-3}$, or a pharmaceutically acceptable salt thereof:

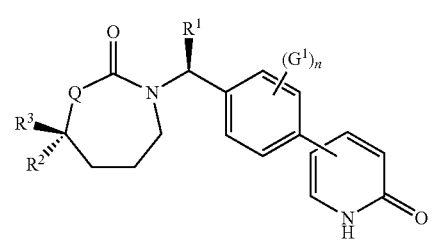

$In^1$

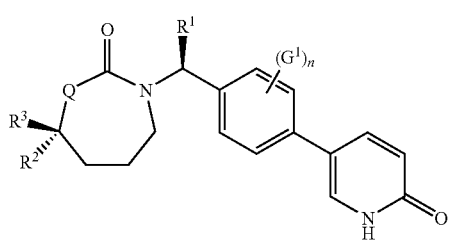

$In^2$

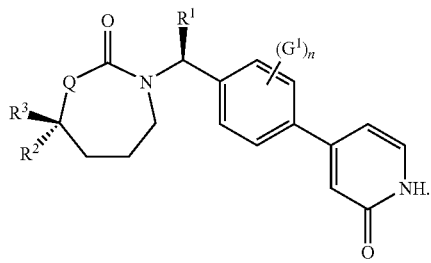

$In^3$

In Formulas $In^{1-3}$, the oxodihydropyridyl ring in Formulas $In^{1-3}$ are optionally substituted (substitution at ring carbons bonded to hydrogen and at nitrogen atoms bonded to hydrogen atoms are encompassed, i.e., a "substitutable ring nitrogen atom") with up to four substituents as described above for $Cy^2$; suitable values for $G^1$ are as described for $G^1$ in Formula If; n is 0, 1, 2 or 3; and suitable substituents for $Cy^2$ and suitable values for $R^1$, $R^2$ and $R^3$ are as defined in any one of the first through twelfth embodiments. Alternatively, n is 0, 1, 2 or 3; suitable values for $G^1$ and substituents for the oxodihydropyridyl ring in Formulas $In^{1-3}$ are as described for $G^1$ and $G^2$, respectively, in Formula If, and values for $R^1$, $R^2$ and $R^3$ are as defined in any one of the first, second, third or fourth embodiments. Alternatively, n is 0, 1, 2 or 3; suitable values for $G^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl ring in Formulas $In^{1-3}$ include $C_1-C_4$ alkyl, $(C_3-C_4)$cycloalkyl, $(C_3-C_4)$cycloalkyl$(C_1-C_2)$alkyl and $C_1-C_4$ haloalkyl; and suitable values for $R^1$, $R^2$ and $R^3$ are as defined in any one of the first, second, third or fourth embodiments.

For each of the embodiments described in the previous paragraph, Q is O or NH.

For each of the embodiments described in the paragraph immediately following Formulas $In^{1-3}$, Q is O or NH and; $R^1$ is preferably methyl or ethyl.

For each of the embodiments described in the paragraph immediately following Formulas $In^{1-3}$, Q is O or NH and; $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $In^{1-3}$, Q is O or NH and; $R^1$ is preferably methyl or ethyl; and $R^3$ is $H_2NC(=O)$ $CMe_2CH_2$, 3-hydroxy-3-methylbutyl, 2-hydroxy-2-methylpropyl or 2-cyano-2-methylpropyl.

For each of the embodiments described in the paragraph immediately following Formulas $In^{1-3}$, Q is O or NH and; $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $In^{1-3}$, Q is O or NH and; $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas In$^{1-3}$, Q is O or NH and; R$^1$ is preferably methyl or ethyl; and R$^3$ is 2-hydroxy-2-methylpropyl or 2-cyano-2-methylpropyl.

For each of the embodiments described in the paragraph immediately following Formulas In$^{1-3}$, Q is O or NH and; R$^1$ is preferably methyl or ethyl; R$^2$ is phenyl or fluorophenyl; and R$^3$ is 2-hydroxy-2-methylpropyl or 2-cyano-2-methylpropyl.

For each of the embodiments described in the paragraph immediately following Formulas In$^{1-3}$, Q is O or NH and; R$^1$ is preferably methyl or ethyl; R$^2$ is phenyl or fluorophenyl; R$^3$ is 2-hydroxy-2-methylpropyl or 2-cyano-2-methylpropyl; the substituent on the substitutable ring nitrogen atom in the oxodihydropyridyl ring in Formulas In$^{1-3}$ is (C$_1$-C$_4$)alkyl, (C$_3$-C$_4$)cycloalkyl, (C$_3$-C$_4$)cycloalkyl(C$_1$-C$_2$)alkyl, or (C$_1$-C$_2$)haloalkyl; and one or two ring carbon atoms in the oxodihydropyridyl ring in Formulas In$^{1-3}$ are optionally substituted with methyl or ethyl.

Another embodiment of the invention is a compound represented by any one of Formulas Io$^{1-2}$ or a pharmaceutically acceptable salt thereof:

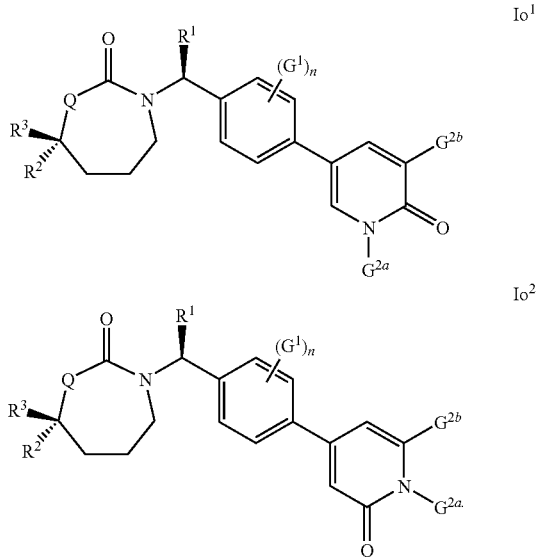

In Formulas Io$^{1-2}$, G$^1$ is (C$_1$-C$_4$)alkyl, (C$_1$-C$_4$)alkoxy, (C$_1$-C$_4$)haloalkyl, (C$_1$-C$_4$)haloalkoxy, halogen, cyano or nitro; n is 0, 1 or 2; G$^{2a}$ is (C$_1$-C$_4$)alkyl, (C$_3$-C$_4$)cycloalkyl or (C$_1$-C$_4$) haloalkyl; G$^{2b}$ is hydrogen, fluorine, chlorine, cyano, hydroxy, amino, (C$_1$-C$_4$)alkyl, (C$_3$-C$_4$)cycloalkyl, (C$_3$-C$_4$) cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl or (C$_1$-C$_4$)alkylcarbonylamino; and suitable values for R$^1$, R$^2$ and R$^3$ are as defined in any one of the first, second, third or fourth embodiments.

For each of the embodiments described in the previous paragraph, Q is O or NH.

For each of the embodiments described in the paragraph immediately following Formulas Io$^{1-2}$, Q is O or NH and; R$^1$ is preferably methyl or ethyl.

For each of the embodiments described in the paragraph immediately following Formulas Io$^{1-2}$, Q is O or NH and; R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Io$^{1-2}$, Q is O or NH and; R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Io$^{1-2}$, Q is O or NH and; R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Io$^{1-2}$, Q is O or NH and; R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Io$^{1-2}$, Q is O or NH and; R$^1$ is preferably methyl or ethyl; and R$^3$ is 2-hydroxy-2-methylpropyl or 2-cyano-2-methylpropyl.

For each of the embodiments described in the paragraph immediately following Formulas Io$^{1-2}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiment described in the paragraph immediately following Formulas Io$^{1-2}$, Q is O or NH and; R$^1$ is preferably methyl or ethyl; R$^2$ is phenyl or fluorophenyl; R$^3$ is 2-hydroxy-2-methylpropyl or 2-cyano-2-methylpropyl; the substituent G$^{2a}$ is selected from (C$_1$-C$_4$)alkyl, (C$_3$-C$_4$) cycloalkyl, (C$_3$-C$_4$)cycloalkyl(C$_1$-C$_2$)alkyl, and (C$_1$-C$_2$)haloalkyl; and G$^{2b}$ is optionally selected from hydrogen, methyl or ethyl.

In certain specific embodiments of the invention, the variables in the above-described structural formulas have the following values:

A$^1$ is (a) a bond, or (b) (C$_1$-C$_3$)alkylene, CH$_2$CH$_2$O, wherein the oxygen is attached to Cy$^1$, or CH$_2$C(=O), wherein the carbonyl carbon is attached to Cy$^1$.

Alternatively, A$^1$ is a bond. Alternatively, A$^1$ is (C$_1$-C$_3$) alkylene. In another specific embodiment, A$^1$ is methylene. In another specific embodiment, if R$^1$ is present, A$^1$ is CH. In another specific embodiment, if R$^1$ is ethyl or methyl and A$^1$ is CH.

R$^1$ is (a) absent or (b) is selected from (C$_1$-C$_6$)alkyl, (C$_2$-C$_6$)alkenyl, (C$_2$-C$_6$)alkynyl or (C$_1$-C$_3$)alkoxy(C$_1$-C$_3$)alkyl, wherein each is optionally substituted with up to four groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN) NR$^4$—, (R$^4$O)$_2$P(=O)O—, (R$^4$O)$_2$P(=O)NR$^4$—, R$^4$OS (=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$ NHC(=O)O—, R$^4$S(=O)$_2$NHC(=O)NR$^4$—, R$^4$OS(=O)$_2$ NHC(=O)—, R$^4$OS(=O)$_2$NHC(=O)O—, R$^4$OS(=O)$_2$ NHC(=O)NR$^4$—, (R$^4$)$_2$NS(=O)$_2$NHC(=O)—, (R$^4$)$_2$NS (=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C (=O)NHS(=O)₂NR⁴—, R⁴OC(=O)NHS(=O)₂—, R⁴OC(=O)NHS(=O)₂O—, R⁴OC(=O)NHS(=O)₂NR⁴—, (R⁴)₂NC(=O)NHS(=O)₂—, (R⁴)₂NC(=O)NHS(=O)₂O—, (R⁴)₂NC(=O)NHS(=O)₂NR⁴—, aryl, cycloalkyl, heterocyclyl, heteroaryl, arylamino and heteroarylamino. In another alternative, R¹ is (C₁-C₆)alkyl. Alternatively, R¹ is absent, or is methyl or ethyl.

Alternatively, R¹ is (C₁-C₆)alkyl, optionally substituted with up to four groups independently selected from fluorine, cyano, oxo, R⁴, R⁴O—, (R⁴)₂N—, R⁴O₂C—, R⁴S, R⁴S(=O)—, R⁴S(=O)₂—, R⁴C(=O)NR⁴—, (R⁴)₂NC(=O)—, (R⁴)₂NC(=O)O—, (R⁴)₂NC(=O)NR⁴—, R⁴OC(=O)NR⁴—, (R⁴)₂NC(=NCN)NR⁴—, (R⁴O)₂P(=O)O—, (R⁴O)₂P(=O)NR⁴—, R⁴OS(=O)₂NR⁴—, (R⁴)₂NS(=O)₂O—, (R⁴)₂NS(=O)₂NR⁴—, R⁴S(=O)₂NR⁴—, R⁴S(=O)₂NHC(=O)—, R⁴S(=O)₂NHC(=O)O—, R⁴S(=O)₂NHC(=O)NR⁴—, R⁴OS(=O)₂NHC(=O)—, R⁴OS(=O)₂NHC(=O)O—, R⁴OS(=O)₂NHC(=O)NR⁴—, (R⁴)₂NS(=O)₂NHC(=O)—, (R⁴)₂NS(=O)₂NHC(=O)O—, (R⁴)₂NS(=O)₂NHC(=O)NR⁴—, R⁴C(=O)NHS(=O)₂—, R⁴C(=O)NHS(=O)₂O—, R⁴C(=O)NHS(=O)₂NR⁴—, R⁴OC(=O)NHS(=O)₂—, R⁴OC(=O)NHS(=O)₂O—, R⁴OC(=O)NHS(=O)₂NR⁴—, (R⁴)₂NC(=O)NHS(=O)₂—, (R⁴)₂NC(=O)NHS(=O)₂O—, (R⁴)₂NC(=O)NHS(=O)₂NR⁴—, aryl, cycloalkyl, heterocyclyl, heteroaryl, arylamino and heteroarylamino.

Cy¹ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylthio, (C₄-C₇)cycloalkylalkylthio, halo(C₁-C₆)alkylthio, halo(C₃-C₆)cycloalkylthio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₂-C₆)alkoxyl or (C₁-C₆)alkylcarbonyl.

Alternatively, Cy¹ is optionally substituted aryl or optionally substituted heteroaryl. Alternatively, Cy¹ is optionally substituted phenyl or optionally substituted pyridyl. In another alternative, Cy¹ is optionally substituted monocyclic cycloalkyl. In another alternative, Cy¹ is optionally substituted cyclohexyl. In another alternative, Cy¹ is optionally substituted phenyl. In another alternative, Cy¹ is phenyl optionally substituted with fluorine, bromine, trifluoromethyl, fluorine, methoxy, methyl, fluorocarboxy, hydroxy alkyl, methoxycarbonyl, or methoxymethyl. In yet another specific embodiment, Cy¹ is substituted with fluorine, chlorine, bromine, methoxy, methoxycarbonyl, carboxy, or methyl. Alternatively, Cy¹ is pyridyl optionally substituted with chlorine. In yet another specific embodiment, Cy¹ is substituted with fluorine or bromine. In another embodiment A² is a bond, Cy² is H and Cy¹ is optionally substituted monocyclic cycloalkyl. In another embodiment A² is a bond, Cy² is H and Cy¹ is optionally substituted cyclohexyl. In another embodiment A² is a bond, Cy² is H and Cy¹ is phenyl substituted with fluorine, chlorine, bromine, methyl, methoxy, methoxycarbonyl, trifluoromethyl, hydroxymethyl or 2-hydroxy-2-propyl. In another embodiment, Cy¹ is 1-(t-BuOC(=O))pyrrolidin-3-yl).

Cy¹ is phenyl, cyclopropyl, cyclohexyl, pyrrolidinyl, pyridyl, N-oxo-pyridyl, thiazolyl or pyrimidinyl optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino.

A² is (a) a bond, O, S or NR⁴; or (b) (C₁-C₃)alkylene or (C₁-C₂)alkyleneoxy, each of which is optionally substituted with 1 to 4 groups independently selected from methyl, ethyl, trifluoromethyl or oxo.

Alternatively, A² is a bond. Alternatively, A² is a bond and Cy² is hydrogen. Alternatively, A² is a bond and Cy² is cyclopropyl. Alternatively, A² is a bond and Cy² is optionally substituted aryl or optionally substituted heteroaryl. In another specific embodiment, A² is a bond and Cy² is optionally substituted phenyl or optionally substituted pyridyl. In yet another specific embodiment, A² is a bond and Cy² is optionally substituted phenyl. In yet another specific embodiment, A² is a bond and Cy² is substituted with 1 to 4 groups independently selected from chlorine or fluorine. In yet another specific embodiment, A² is a bond and Cy² is difluorophenyl. In yet another specific embodiment, A² is a bond and Cy² is fluorophenyl. In yet another specific embodiment A² is a bond and Cy² is optionally substituted 2-thienyl, 1-pyrazolyl, 3-pyrazolyl, 1,2,4-thiadiazol-3-yl, thiazolyl or 2-oxo-1,2-dihydro-5-pyridyl. In yet another specific embodiment, A² is a bond and Cy² is phenyl or thienyl substituted with amino(C₁-C₆)alkyl.

Alternatively, A² is a bond, O, OCH₂CO or C=O.

Cy² is aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylthio, (C₄-C₇)cycloalkylalkylthio, halo(C₁-C₆)alkylthio, halo(C₃-C₆)cycloalkylthio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)

cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl.

Alternatively, $Cy^2$ is optionally substituted pyridyl. In one embodiment, $Cy^2$ is pyridyl optionally substituted with oxo, alkyl, methoxy, fluorine, chlorine, or trifluoromethyl. Alternatively, $Cy^2$ is optionally substituted thienyl. In one embodiment, $Cy^2$ is thienyl optionally substituted with MeCO, $H_2NCHMe$ or HOCHMe. Alternatively, $Cy^2$ is optionally substituted phenyl. In one embodiment, $Cy^2$ is phenyl optionally substituted with fluorine, chlorine, methoxy, methyl or cyano. Alternatively, $Cy^2$ is optionally substituted phenyl. In one embodiment, $Cy^2$ is thiazolyl or thiaziazol, each optionally substituted with methyl. Alternatively, $Cy^2$ is pyrazolyl optionally substituted with trifluoromethyl. Alternatively, $Cy^2$ is optionally substituted pyrazolyl, morpholinyl, or cyclopropyl.

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl or $(C_1-C_6)$alkylcarbonyl.

$Cy^2$ is (a) hydrogen or (b) phenyl, thienyl, pyridyl, N-oxopyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl.

Y is $(C_1-C_6)$alkyl or halo$(C_1-C_6)$alkyl.

n is 0, 1 or 2. In another embodiment, n is 0.

X is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl.

m is 0, 1, 2, 3, 4. Alternatively, m is 1, 2, 3, or 4. In another embodiment, m is 1, 2 or 3.

E is (a) a bond or (b) $(C_1-C_3)$alkylene or $(C_1-C_2)$alkylenyloxy, wherein the 0 is attached to $R^2$, each of which is optionally substituted with 1 to 4 groups independently selected from methyl, ethyl, trifluoromethyl or oxo.

E is a bond or $CH_2$.

In a specific embodiment E is a bond. In another specific embodiment, E is a bond when $R^2$ is optionally substituted aryl, optionally substituted heteroaryl or optionally substituted cycloalkyl. In another specific embodiment, E is a bond when $R^2$ is optionally substituted phenyl, optionally substituted thienyl or optionally substituted pyridyl. In yet another specific embodiment, E is a bond when $R^2$ is optionally substituted phenyl.

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl or $(C_1-C_6)$alkylcarbonyl.

$R^2$ is aryl, heteroaryl, cycloalkyl or heterocyclyl, wherein each 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl and E is a bond.

$R^2$ is optionally substituted aryl, optionally substituted heteroaryl or cycloalkyl or alkyl. In one specific embodiment, $R^2$ is optionally substituted phenyl, optionally substituted pyridyl or optionally substituted thienyl. In another embodiment, $R^2$ is optionally substituted alkyl. In one specific embodiment, $R^2$ is optionally substituted isopropyl. In one specific embodiment, $R^2$ is phenyl optionally substituted with methyl, chlorine, flourine, or methylthio. In another specific embodiment, $R^2$ is optionally substituted phenyl. In yet another specific embodiment, $R^2$ is fluorophenyl.

$R^2$ is isopropyl, thienyl, phenyl, or pyridyl, each optionally substituted with halo, methyl, methylthio or (4-morpholino)methyl.

$R^3$ is selected from $(C_1-C_6)$alkyl, $(C_2-C_6)$alkenyl, $(C_2-C_6)$alkynyl and $(C_1-C_3)$alkoxy$(C_1-C_3)$alkyl, wherein each is optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4$, $(R^4O)_2P(=O)O—$, $(R^4O)_2P(=O)NR^4—$, $R^4OS(=O)_2NR^4$, $(R^4)_2NS(=O)_2O—$, $(R^4)_2NS(=O)_2NR^4$, $R^4S(=O)_2NR^4—$, $R^4S(=O)_2NHC(=O)—$, $R^4S(=O)_2NHC(=O)O—$, $R^4S(=O)_2NHC(=O)NR^4$, $R^4OS(=O)_2NHC(=O)—$, $R^4OS(=O)_2NHC(=O)O—$, $R^4OS(=O)_2NHC(=O)NR^4$, $(R^4)_2NS(=O)_2NHC(=O)—$, $(R^4)_2NS(=O)_2NHC(=O)O—$, $(R^4)_2NS(=O)_2NHC(=O)NR^4$, $R^4C(=O)NHS(=O)_2—$, $R^4C(=O)NHS(=O)_2O—$, $R^4C(=O)NHS(=O)_2NR^4$, $R^4OC(=O)NHS(=O)_2—$, $R^4OC(=O)NHS(=O)_2O—$, $R^4OC(=O)NHS(=O)_2NR^4$, $(R^4)_2NC(=O)NHS(=O)_2—$, $(R^4)_2NC(=O)NHS(=O)_2O—$, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo).

$R^3$ is selected from substituted $(C_1-C_6)$alkyl, or optionally substituted $(C_2-C_6)$alkenyl, optionally substituted $(C_2-C_6)$alkynyl and optionally substituted $(C_1-C_3)$alkoxy$(C_2-C_3)$alkyl, wherein each substituted group represented by $R^3$ has up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4$, $(R^4O)_2P(=O)O—$, $(R^4O)_2P(=O)NR^4—$, $R^4OS(=O)_2NR^4$, $(R^4)_2NS(=O)_2O$, $(R^4)_2NS(=O)_2NR^4$, $R^4S(=O)_2NR^4—$, $R^4S(=O)_2NHC(=O)—$, $R^4S(=O)_2NHC(=O)O—$, $R^4S(=O)_2NHC(=O)NR^4$, $R^4OS(=O)_2NHC(=O)—$, $R^4OS(=O)_2NHC(=O)O—$, $R^4OS(=O)_2NHC(=O)NR^4$, $(R^4)_2NS(=O)_2NHC(=O)—$, $(R^4)_2NS(=O)_2NHC(=O)O—$, $(R^4)_2NS(=O)_2NHC(=O)NR^4$, $R^4C(=O)NHS(=O)_2—$, $R^4C(=O)NHS(=O)_2O—$, $R^4C(=O)NHS(=O)_2NR^4$, $R^4OC(=O)NHS(=O)_2—$, $R^4OC(=O)NHS(=O)_2O—$, $R^4OC(=O)NHS(=O)_2NR^4$, $(R^4)_2NC(=O)NHS(=O)_2—$, $(R^4)_2NC(=O)NHS(=O)_2O—$, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

In another embodiment, $R^3$ is selected from substituted $(C_1-C_6)$alkyl, or optionally substituted $(C_2-C_6)$alkenyl, optionally substituted $(C_2-C_6)$alkynyl and optionally substituted $(C_1-C_3)$alkoxy$(C_2-C_3)$alkyl, wherein each substituted group represented by $R^3$ has up to four groups independently selected from cyano, $R^4$, $(R^4)_2N—$, $R^4S$, $R^4S(=O)—$, $R^4S(=O)_2—$, $R^4C(=O)NR^4$, $(R^4)_2NC(=O)—$, $(R^4)_2NC(=O)O—$, $(R^4)_2NC(=O)NR^4$, $R^4OC(=O)NR^4$, $(R^4)_2NC(=NCN)NR^4$, $(R^4O)_2P(=O)O—$, $(R^4O)_2P(=O)NR^4$, $R^4OS(=O)_2NR^4$, $(R^4)_2NS(=O)_2O—$, $(R^4)_2NS(=O)_2NR^4$, $R^4S(=O)_2NR^4$, $R^4S(=O)_2NHC(=O)—$, $R^4S(=O)_2NHC(=O)O—$, $R^4S(=O)_2NHC(=O)NR^4$, $R^4OS(=O)_2NHC(=O)—$, $R^4OS(=O)_2NHC(=O)O—$, $R^4OS(=O)_2NHC(=O)NR^4$, $(R^4)_2NS(=O)_2NHC(=O)—$, $(R^4)_2NS(=O)_2NHC(=O)O—$, $(R^4)_2NS(=O)_2NHC(=O)NR^4$, $R^4C(=O)NHS(=O)_2—$, $R^4C(=O)NHS(=O)_2O—$, $R^4C(=O)NHS(=O)_2NR^4$, $R^4OC(=O)NHS(=O)_2—$, $R^4OC(=O)NHS(=O)_2O—$, $R^4OC(=O)NHS(=O)_2NR^4$, $(R^4)_2NC(=O)NHS(=O)_2—$, $(R^4)_2NC(=O)NHS(=O)_2O—$, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo).

$R^3$ is $(HO)_2P(=O)(C_1-C_4)$alkyl. $R^3$ is hydroxy$(C_2-C_5)$alkyl. In yet another specific embodiment $R^3$ is 3-hydroxybutyl, 3-hydroxy-3-methylbutyl, 3-hydroxypropyl, 2-hydroxypropyl, 2-hydroxy-2-methylpropyl, or 2-hydroxyethyl. Alternatively, $R^3$ is dihydroxy$(C_3-C_4)$alkyl. In yet another specific embodiment $R^3$ is 2,3-dihydroxypropyl. $R^3$ is amino$(C_2-C_5)$alkyl or methylamino$(C_2-C_5)$alkyl, each optionally substituted with hydroxy. In another specific embodiment, $R^3$ is $\omega$-$H_2NCO(C_1-C_3)$alkyl. In another specific embodiment, $R^3$ is $H_2NCONH(C_1-C_3)$alkyl, optionally substituted with hydroxy. In another specific embodiment, $R^3$ is $H_2NCH_2CONH(C_1-C_3)$alkyl, optionally substituted with hydroxy. In another specific embodiment, $R^3$ is $(C_1-C_3)$alkylHNCONH$(C_1-C_3)$alkyl. In yet another specific embodiment, $R^3$ is $H_2NC(=O)C_1-C_4$ alkyl. In yet another specific embodiment, $R^3$ is MeC$(=O)NHC_1-C_4$ alkyl. In yet another specific embodiment, $R^3$ is MeOC$(=O)NHC_1-C_4$ alkyl. In yet another specific embodiment, $R^3$ is MeNHC$(=O)C_1-C_4$ alkyl. In yet another specific embodiment $R^3$ is $H_2NC(=O)OC_1-C_4$ alkyl. In yet another specific embodiment, $R^3$ is MeHNC$(=O)OC_1-C_4$ alkyl. In yet another specific embodiment, $R^3$ is $(C_1-C_2)$alkoxy$(C_1-C_3)$alkyl, optionally substituted with hydroxy. In yet another specific embodiment, $R^3$ is $(C_1-C_2)$alkylthio$(C_1-C_3)$alkyl, optionally substituted with hydroxy. In yet another specific embodiment, $R^3$ is $H_2NSO_2O(C_2-C_4)$alkyl. In yet another specific embodiment, $R^3$ is $H_2NSO_2NH(C_2-C_4)$alkyl. In yet another specific embodiment, $R^3$ is oxo$(C_2-C_4)$alkyl. In yet another specific embodiment, $R^3$ is MeCO$(C_1-C_2$alkyl). In yet another specific embodiment, $R^3$ is HOCO$(C_1-C_2$alkyl). In yet another specific embodiment, $R^3$ is alkenyl. In yet another specific embodiment, $R^3$ is alkyl. In yet another specific embodiment, $R^3$ is allyl. In yet another specific embodiment, $R^3$ is MeC$(=O)NH(C_2-C_4)$alkyl. In yet another specific embodiment, $R^3$ is MeOC$(=O)NH(C_2-C_4)$alkyl. In yet another specific embodiment, $R^3$ is cyanoalkyl. In yet another specific embodiment, $R^3$ is alkylsulfonylaminoalkyl. In yet another specific embodiment, $R^3$ is alkylsulfonylalkyl. In yet another specific embodiment $R^3$ is MeSO$_2NH(C_2-C_4)$alkyl, optionally substituted with hydroxy. In yet another specific embodiment, $R^3$ is aminocarbonylaminoalkyl. In yet another specific embodiment, $R^3$ is aminocarboxyalkyl. In yet another specific embodiment $R^3$ is 2-(4-morpholino)ethyl. In yet another specific embodiment $R^3$ is 2-(1-imidazolyl)ethyl. In yet another specific embodiment $R^3$ is 2-(1-aminoimidazolyl)ethyl.

Alternatively, $R^3$ is $(C_1-C_6)$alkyl substituted by up to four groups independently selected from cyano, oxo, HO—, $(R^4)_2N—$, $R^4O_2C—$, $R^4S$, $R^4S(=O)—$, $R^4S(=O)_2—$, $R^4C(=O)NR^4$, $(R^4)_2NC(=O)—$, $(R^4)_2NC(=O)O—$, $(R^4)_2NC(=O)NR^4$, $R^4OC(=O)NR^4$, $(R^4)_2NC(=NCN)NR^4$, $(R^4O)_2P(=O)O—$, $(R^4O)_2P(=O)NR^4$, $R^4OS(=O)_2NR^4$, $(R^4)_2NS(=O)_2O$, $(R^4)_2NS(=O)_2NR^4$, $R^4S(=O)_2NR^4$, $R^4S(=O)_2NHC(=O)—$, $R^4S(=O)_2NHC(=O)O—$, $R^4S(=O)_2NHC(=O)NR^4$, $R^4OS(=O)_2NHC(=O)—$, $R^4OS(=O)_2NHC(=O)O—$, $R^4OS(=O)_2NHC(=O)NR^4$, $(R^4)_2NS(=O)_2NHC(=O)—$, $(R^4)_2NS(=O)_2NHC(=O)O—$, $(R^4)_2NS(=O)_2NHC(=O)NR^4$, $R^4C(=O)NHS(=O)_2—$, $R^4C(=O)NHS(=O)_2O—$, $R^4C(=O)NHS(=O)_2NR^4$, $R^4OC(=O)NHS(=O)_2—$, $R^4OC(=O)NHS(=O)_2O—$, $R^4OC(=O)NHS(=O)_2NR^4$, $(R^4)_2NC(=O)NHS(=O)_2—$, $(R^4)_2NC(=O)NHS(=O)_2O—$, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo).

$R^3$ is methyl, ethyl, propyl, butyl, vinyl, allyl or ethoxyethyl, each optionally substituted with up to two groups independently selected from HO—, MeO—, $H_2N—$, MeC$(=O)NH—$, MeS$(=O)_2NH—$, $H_2NC(=O)—$, MeNHC$(=O)$, $HO_2C—$, $(HO)_2P(=O)O—$, $H_2NS(=O)_2O—$, $H_2NS(=O)_2NH—$, MeNHC$(=O)NH—$, MeNHC$(=O)O$ oxo, cyano, HO$_2$C—, HOCH$_2$CH$_2$NH—, 4-morpholino, HOCH$_2$C(=O)NH—, H$_2$NCH$_2$C(=O)NH, EtNHC(=O)NH, MeOC(=O)NH—, MeNHC(=NC≡N)NH—, Me-, MeS—, MeSO$_2$—, MeSO$_2$N(Me)—, MeS(=O)$_2$NHC(=O)—, imidazolylamino-, imidazolyl, tetrazolyl, H$_2$NCONH—, H$_2$NCO$_2$—, HOCH$_2$CH$_2$O—, MeNH—, Me$_2$N— or MeCONMe.

R$^4$ is independently selected from H, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl and (C$_1$-C$_6$)alkoxy(C$_1$-C$_6$)alkyl.

R$^5$ is H, (C$_1$-C$_6$)alkyl, halo(C$_1$-C$_6$)alkyl, or hydroxy(C$_1$-C$_6$)alkyl. R$^5$ is hydrogen or methyl. In one specific embodiment, R$^5$ is hydrogen.

r is 0, 1, 2, 3 or 4.

s 0, 1, 2, 3 or 4.

G is fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylthio, (C$_4$-C$_7$)cycloalkylalkylthio, halo(C$_1$-C$_6$)alkylthio, halo(C$_3$-C$_6$)cycloalkylthio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl or (C$_1$-C$_6$)alkylcarbonyl.

G$^1$ and G$^2$ are independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylthio, (C$_4$-C$_7$)cycloalkylalkylthio, halo(C$_1$-C$_6$)alkylthio, halo(C$_3$-C$_6$)cycloalkylthio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkyl-aminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl and (C$_1$-C$_6$)alkylcarbonyl.

In another embodiment of the invention, the provisos applied to pharmaceutical compositions comprising compounds of Formula I, I*, I** also apply to methods of treatment utilizing any one of the compounds of Formula I, I*, I** or Formulas Ia-Ig, Il$^{1-3}$, Im$^{1-3}$, In$^{1-3}$, or Io$^{1-2}$.

Another embodiment of the invention is a compound of Formulas I, I*, I**, Ia, Ib, Ic, Id, Ie, If, Ig, Il$^{1-3}$, Im$^{1-3}$, In$^{1-3}$, or Io$^{1-2}$ or a pharmaceutically acceptable salt, enantiomer or diastereomer thereof wherein any of the following provisos apply Proviso 1: If (a) Q is O; (b) A$^1$-Cy$^1$ is alkyl substituted with aryl; or cycloalkyl or aryl; each optionally substituted by aryl, alkyl, alkenyl, alkynyl, alkoxy, formyl, carbonyl, carboxyl, alkoxycarbonyl, hydroxyl, mercapto, halogen, sulfonyl or amino; (c) R$^3$ is an alkyl, alkenyl, alkynyl optionally substituted with alkyl, alkoxy, oxo, carboxy, alkoxycarbonyl, hydroxy, mercapto, fluorine, sulfonyl, and amino; (d) then E-R$^2$ is not alkyl, aryl, cycloalkyl each optionally substituted with alkyl, alkenyl, alkynyl, aryl, alkoxy, oxo, carboxy, alkoxycarbonyl, hydroxy, mercapto, halogen, sulfonyl, or amino.

Proviso 2: If (a) A$^1$-Cy$^1$ is cycloalkyl; and (b) R$^3$ is alkyl optionally substituted with hydroxy or alkoxy; or alkoxyalkyl substituted with oxo; (c) then (i) E-R$^2$ is not alkyl optionally substituted with aryl, hydroxy or alkoxy; or (ii) E-R$^2$ is not unsubstituted cycloalkyl or unsubstituted aryl or (iii) E is not alkoxy and R$^2$ is not alkyl substituted with oxo.

Proviso 3: If (a) A$^1$ and A$^2$ are both bonds, (b) R$^3$ is an alkyl optionally substituted with amino, alkyl, alkoxy, oxo, carboxy, hydroxy, fluorine, or sulfonyl, or an unsubstituted alkynyl (c) E-R$^2$ is (i) a optionally substituted alkyl or an optionally substituted carbocyclic aromatic group wherein the substituent is an amino, alkyl, alkenyl, alkynyl, alkoxy, carboxy, hydroxy, halogen or sulfonyl, or (ii) an unsubstituted cycloalkyl, and (d) Cy$^2$ is H, then Cy$_1$ is not (i) an unsubstituted monocyclic cycloalkyl or (ii) a substituted or unsubstituted carbocyclic aromatic group.

Proviso 4: If (a) A$^1$ and A$^2$ are both bonds, (b) R$^3$ is an alkyl optionally substituted with amino, alkyl, alkoxy, oxo, carboxy, hydroxy, fluorine, or sulfonyl, or an unsubstituted alkynyl (c) E-R$^2$ is (i) a optionally substituted alkyl or an optionally substituted carbocyclic aromatic group wherein the substituent is an amino, alkyl, alkenyl, alkynyl, alkoxy, carboxy, hydroxy, halogen or sulfonyl, or (ii) an unsubstituted cycloalkyl, and (d) Cy$^1$ is an optionally substituted carbocyclic aromatic group, then Cy$^2$ is not an unsubstituted carbocyclic aromatic group.

Proviso 5: If (a) A$^1$ is alkyl optionally substituted with amino, alkyl, alkoxy, oxo, carboxy, hydroxy, fluorine, or sulfonyl, (b) R$^3$ is an alkyl substituted with amino, alkyl, alkoxy, oxo, carboxy, hydroxy, fluorine, or sulfonyl, or an unsubstituted alkynyl (c) E-$R^2$ is (i) a optionally substituted alkyl or an optionally substituted carbocyclic aromatic group wherein the substituent is an amino, alkyl, alkenyl, alkynyl, alkoxy, carboxy, hydroxy, halogen or sulfonyl, or (ii) an unsubstituted cycloalkyl, then $Cy^1$ is a carbocyclic aromatic group optionally substituted with $C_1$-$C_4$ alkoxy or halogen.

DEFINITIONS

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. A heterocyclyl can be optionally substituted with 1-4 substituents. Exemplary substituents include alkyl, haloalkyl and oxo.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The invention can also include solvates and hydrates.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

The following abbreviations have the indicated meanings:

| Abbreviation | Meaning |
| --- | --- |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC•HCl, EDCl | 1-[3-(dimethylamino)propyl]-3-ethylcarbodiimide hydrochloride equivalents |
| Equiv | |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |

-continued

| Abbreviation | Meaning |
| --- | --- |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthetic Methods

Compounds of Formula I can be prepared by several processes. In the discussion below, $A^1$, $A^2$, $Cy^1$, $Cy^2$, E, Q, $R^1$, $R^2$, $R^3$, $R^5$, Y and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I, wherein Q is $NR^5$ can be prepared by reaction of diamine intermediate of Formula II with a reagent of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or NaHCO$_3$ respectively, at −10° C. to 120° C.:

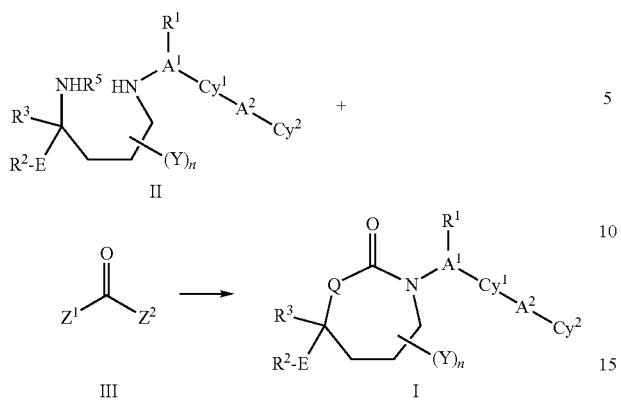

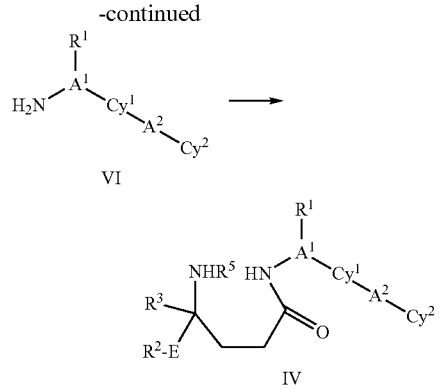

Certain instances of reagent III are especially convenient because they are commercially available. For example when $Z^1$ and $Z^2$ are both chloride, III is phosgene. When $Z^1$ and $Z^2$ are both 1-imidazolyl, III is carbonyl diimidazole. When $Z^1$ is chloride and $Z^2$ is p-nitrophenoxide, III is p-nitrophenyl chloroformate. When $Z^1$ and $Z^2$ are both $OCCl_3$, III is triphosgene and as little as one third of molar equivalent can be used.

Diamine intermediates of Formula II, wherein n=0, can be prepared by reduction of amides of Formula IV using a hydride reagent such as $BH_3$.THF solution, $BH_3.Me_2S$ or $LiAlH_4$ in an inert solvent ethereal such as THF or DME at 20° C. to 100° C. for between 1 h and 48 h:

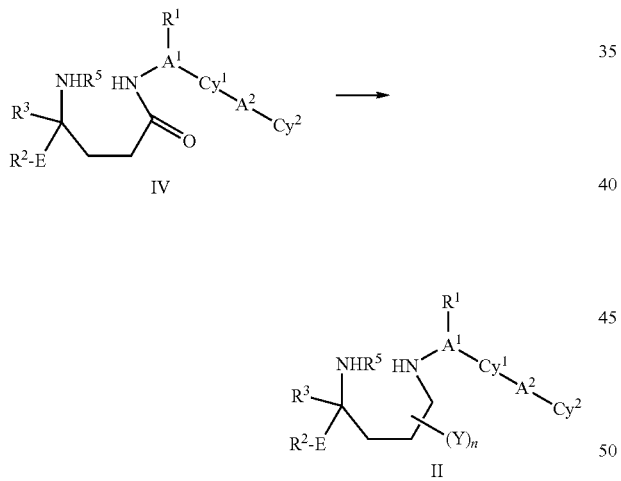

Aminoamide intermediates of Formula IV can be prepared by coupling of a γ-aminoacid of Formula V with an amine of Formula VI using standard peptide coupling reagents such as EDC in the presence of HOBt and N,N-diisopropylethylamine in an inert solvent such as $CH_2Cl_2$ at 0-30° C. for between 1 h and 24 h:

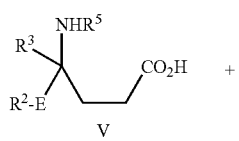

γ-Amino acids of Formula V can be prepared hydrolysis of γ-aminoesters of Formula VII, wherein $R^a$ is lower alkyl, with LiOH, NaOH or KOH.

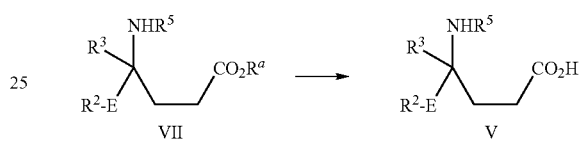

γ-Aminoesters of Formula VII, wherein $R^5$ is H, can be prepared by reduction of γ-nitroesters of Formula VIII.

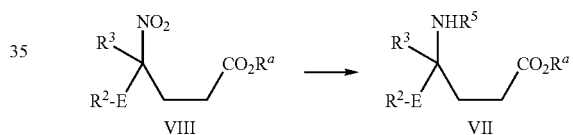

γ-Nitroesters of Formula VIII can be prepared by Michael addition of nitro compounds of Formula IX to acrylate esters of Formula X.

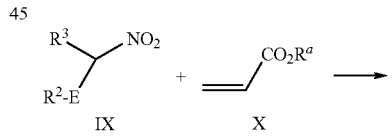

γ-Aminoacids of Formula V can also be prepared from homoallyl amines of Formula XI by hydroboration using a borane such as disiamylborane, followed by oxidation with, for example, Jones reagent.

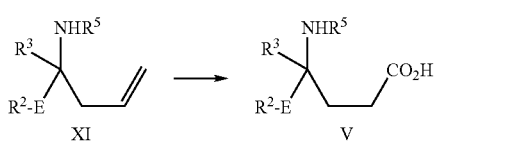
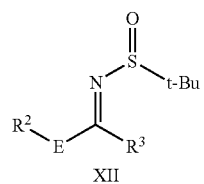

Homoallyl amines of Formula XI can be prepared by addition of allylmagnesium halides to sulfinylimines of Formula XII, followed by acid treatment to remove the t-butylsulfinyl group.

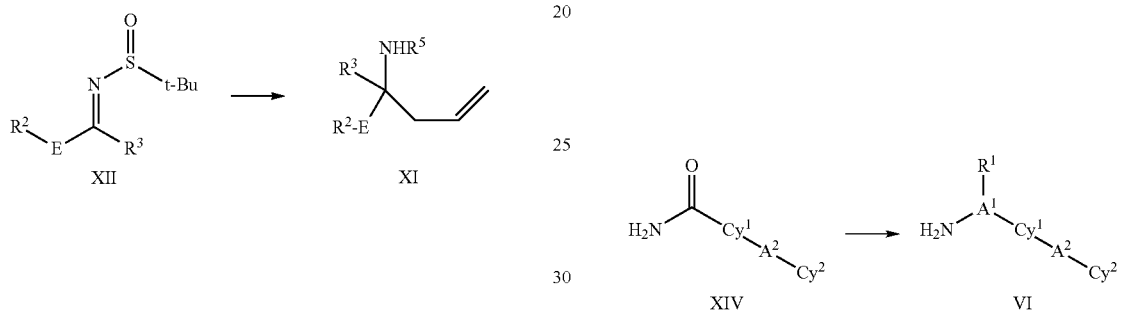

Sulfinylimines of Formula XII can be prepared by reaction of ketones of Formula XIII with 2-methylpropane-2-sulfinamide.

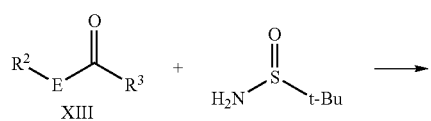

Amine intermediates of Formula VI, wherein $A^1=CH_2$ and $R^1$ is absent, can be prepared by reduction of amides of Formula XIV using a hydride reagent such as $BH_3$.THF solution, $BH_3.Me_2S$ or $LiAlH_4$ in an inert solvent ethereal such as THF or DME at 20° C. to 100° C. for between 1 h and 48 h:

Amine intermediates of Formula VI, wherein $A^1$ is a bond, $R^1$ is absent and $Cy^1$ is not an aromatic or heteroaromatic ring, can be prepared from ketones of formula XV via oximes of Formula XVI or by reductive amination of ketones of Formula XV with ammonia:

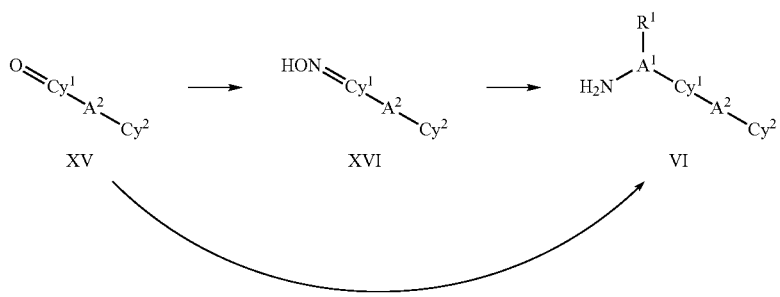

Methods for the conversion of ketones to oximes are described in Smith, M. B. and March, J. "March's Advanced Organic Chemistry" pp 1194-1195, 5th Edition, Wiley, New York, N.Y., 2001. Methods for the reduction of oximes to primary amines are described in Smith, M. B. and March, J. "March's Advanced Organic Chemistry" p 1555, 5th Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Amine intermediates of Formula VI, wherein $A^1$ is CH, can be prepared from ketones of Formula XVII by reductive amination with ammonia.

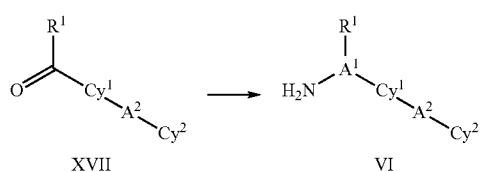

Amine intermediates of Formula VI, wherein $A^1$ is CH, can be prepared from alcohols of Formula XVIII via azides of Formula XIX. The conversion of alcohols of Formula XVIII to azides of Formula XIX can be accomplished with, for example, diphenylphosphoryl azide. Reduction of azides of Formula XIX to amines of Formula VI can be effected, for example, by hydrogenation in the presence of a palladium catalyst or by reaction with triphenylphosphine in wet THF.

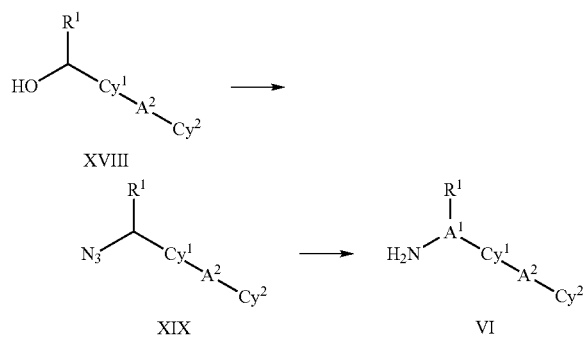

Amine intermediates of Formula VI, wherein $A^1$ is CH, can be prepared by reaction of sulfinyl imine intermediates of Formula XX with organometallic reagents of Formula XXI, wherein M is Li, MgCl, MgBr or MgI, followed by treatment with acid to remove the t-butylsulfinyl group.

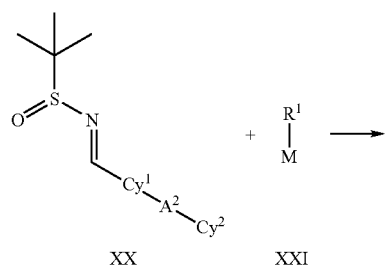

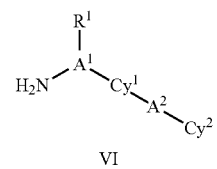

Sulfinyl imines of Formula XX can be prepared by treatment of aldehyde intermediates of Formula XXII with 2-methylpropane-2-sulfinamide.

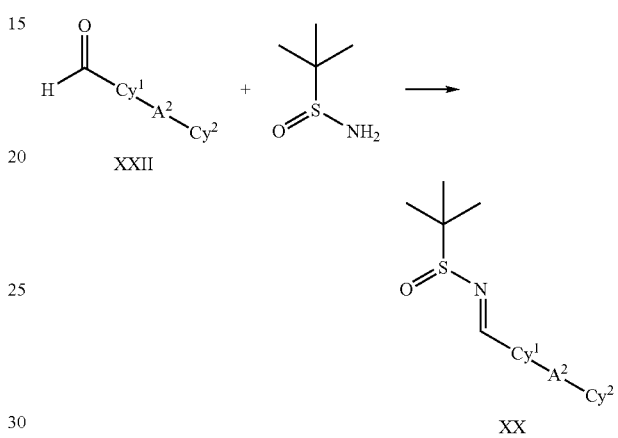

Intermediates of Formula II, wherein $A^1$ is $CH_2$ and $R^1$ is absent, can be prepared by reduction of amide intermediates of formula XXIII using hydride reagents such as $BH_3$.THF solution, $BH_3$.$Me_2$S or $LiAlH_4$ in an inert solvent ethereal such as THF or DME at 20° C. to 100° C. for between 1 h and 48 h:

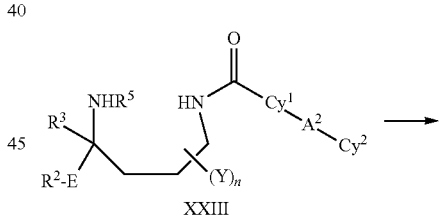

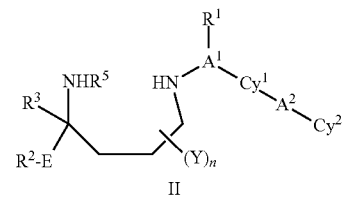

Amide intermediates of Formula XXIII can be prepared by reaction of diamine intermediates of Formula XXIV with activated carboxylic acids of Formula XXV wherein $Z^3$ is chloride or an activated ester, such as an N-hydroxysuccinimide ester:

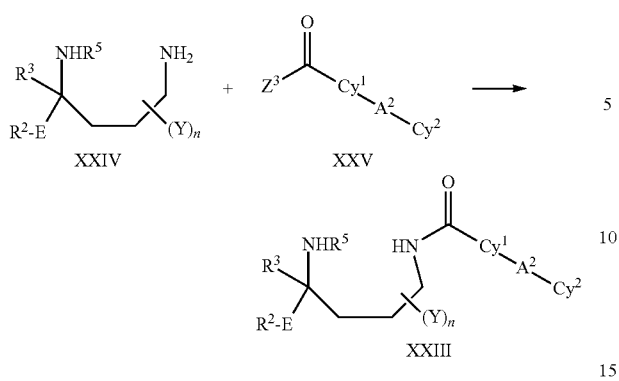

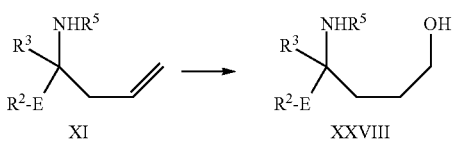

Aminoalcohol intermediates of Formula XXVIII can be prepared by hydroboration of homoallylic amines of Formula XI:

Diamine intermediates of Formula XXIV, wherein n is 0, can be prepared directly by treatment of sulfonate intermediates of Formula XXVI, wherein $R^c$ is for example methyl, trifluoromethyl or p-methylphenyl, with ammonia. Alternatively, sulfonate intermediates of Formula XXVI can be treated with $NaN_3$ to give azides XXVII, followed by reduction using $PPh_3$ in wet THF or $H_2$ gas and a palladium catalyst to give diamines of Formula XXIV.

Diamine intermediates of Formula II, wherein $A^1$ is $CH_2$ and $R^1$ is absent, can be prepared by reaction of, preferably protected, diamines of Formula XXIV with aldehydes of Formula XXII in the presence of a reducing agent such as $NaCNBH_3$ or $Na(OAc)_3BH$:

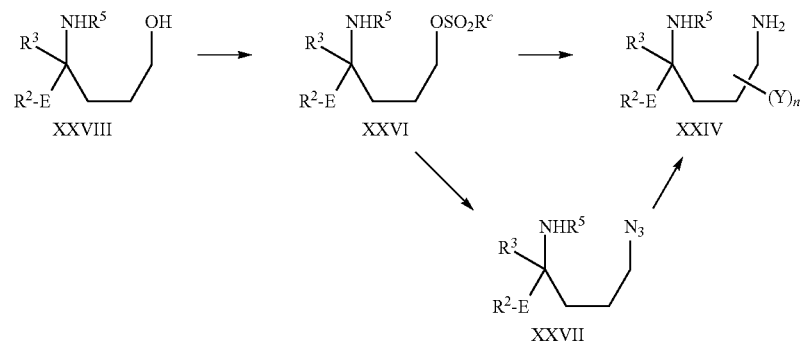

Sulfonate intermediates of Formula XXVI are prepared by reaction of, preferably N-protected, aminoalcohol intermediates Formula XXVIII with $R^cSO_2Cl$ or $(R^cSO_2)_2O$. In addition sulfonate intermediates of Formula XXVI can be reacted with amines of Formula VI to afford diamine intermediates of Formula II:

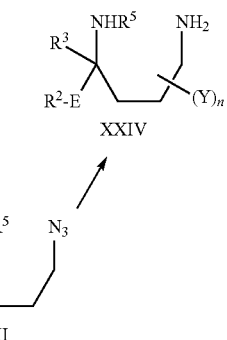

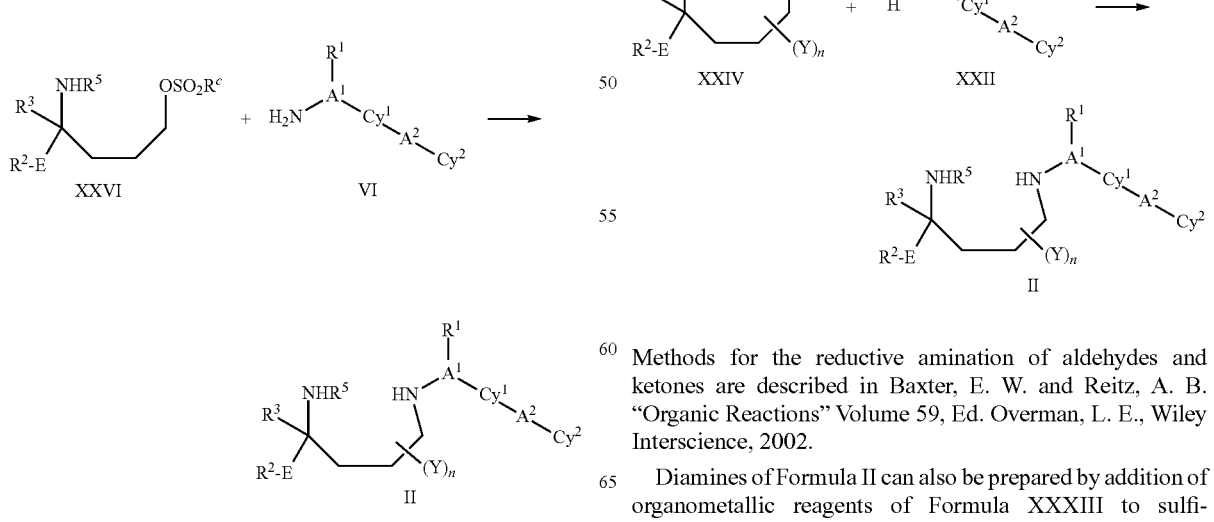

Methods for the reductive amination of aldehydes and ketones are described in Baxter, E. W. and Reitz, A. B. "Organic Reactions" Volume 59, Ed. Overman, L. E., Wiley Interscience, 2002.

Diamines of Formula II can also be prepared by addition of organometallic reagents of Formula XXXIII to sulfinylimines of Formula XXXIV.

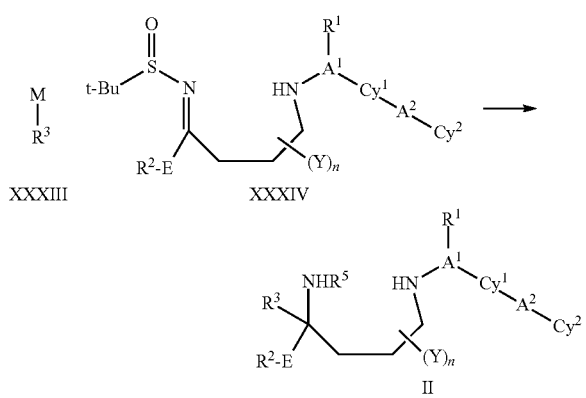

Sulfinylimines of Formula XXXIV can be prepared by condensation of ketoamides of Formula XXXI with 2-methylpropane-2-sulfinamide.

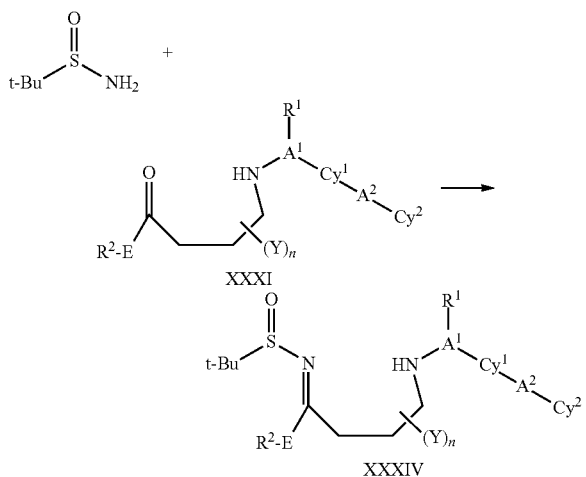

In a second process compounds of Formula I, wherein $R^1$ is absent and $A^1$ is $CH_2$, can be prepared by reaction of compounds of Formula XXXV, with alkylating agents of Formula XXXVI, wherein $Z^4$ is a leaving group such as Br, I, $OSO_2Me$, $OSO_2CF_3$ or $OSO_2Ph$, in the presence of a base such as NaH or $K_2CO_3$:

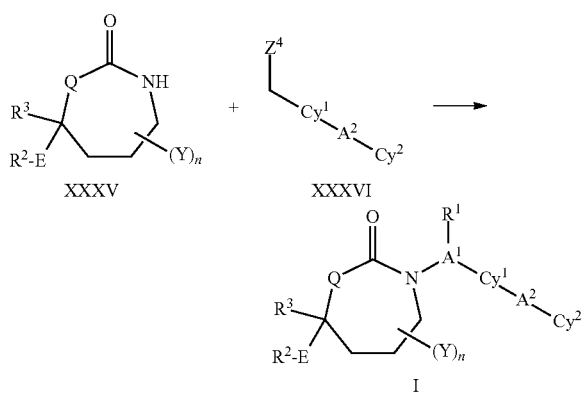

Compounds of Formula XXXV, wherein Q is $NR^5$, can be prepared by treatment of compounds of Formula XXIV with various reagents of Formula II, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at −10° C. to 120° C.:

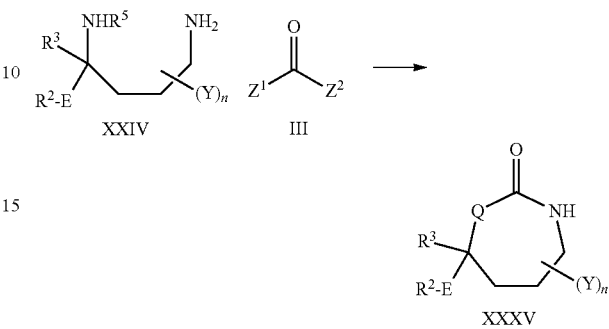

Compounds of Formula XXXV, wherein n is 0, Q is O or $NR^5$ and $R^5$ is $(C_1-C_6)$alkyl, can be prepared by treatment of intermediates of Formula XXXVII with strong bases, such as sodium hydride, in inert solvents, such as DMF.

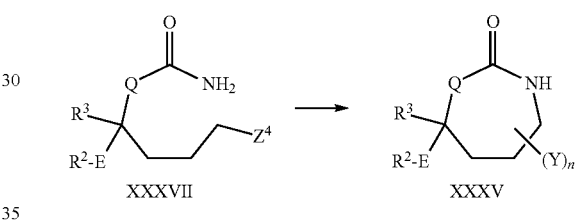

Intermediates of Formula XXXVII, wherein Q is O, can be prepared from alcohols of Formula XXXVIII by treatment with HNCO, prepared from in situ from KNCO and $CF_3CO_2H$, with $Me_3SiNCO$ or with $Cl_3CC(=O)NCO$.

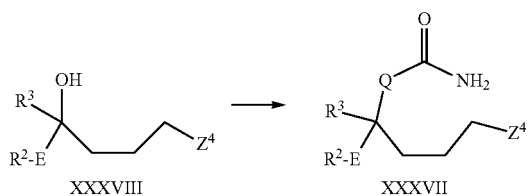

Alcohols of Formula XXXVIII, wherein $Z^4$ is a sulfonate, such as $OSO_2Me$, $OSO_2CF_3$ or $OSO_2Ph$, can be prepared diols of Formula XXXIX by treatment with a sulfonyl chlorides, such as $MeSO_2Cl$ or $PhSO_2Cl$, or sulfonic anhydrides, such as methanesulfonic anhydride or triflic anhydride.

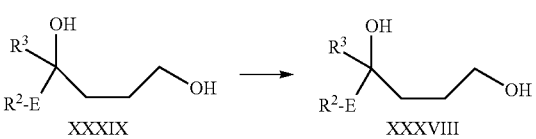

Diols of Formula XXXIX can be prepared by hydroboration of homoallylic alcohols of Formula XL, using, for example diasiamylborane.

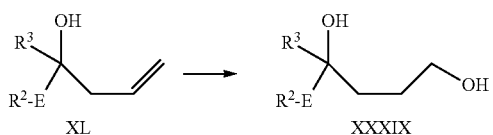

Homoallylic alcohols of Formula XL can be prepared from aldehydes or ketones of Formula XIII and allyl organometallic reagents of Formula XLI, wherein M is MgBr, MgCl or SiMe$_3$.

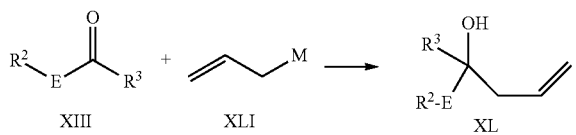

In a third process, compounds of Formula I wherein n is 0, Q is O or NR$^5$ and R$^5$ is (C$_1$-C$_6$)alkyl, can be prepared by treatment of compounds of Formula XLII, wherein Z$^5$ is a leaving group such as Cl, Br, I, OSO$_2$Me, OSO$_2$CF$_3$ or OSO$_2$Ph, with strong bases, such as NaH, in inert solvents, such as DMF.

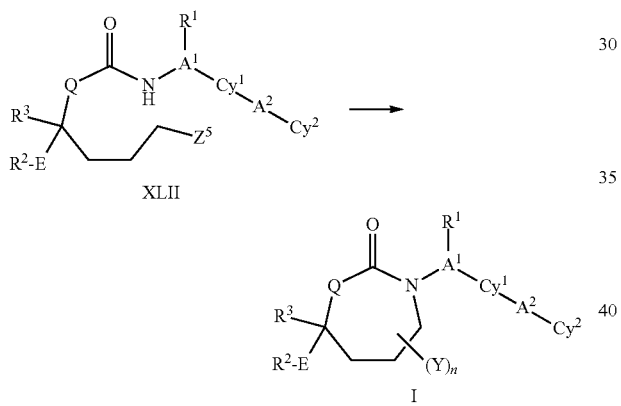

Compounds of Formula XLII, wherein Q is O and Z$^5$ is a sulfonate such as OSO$_2$Me, OSO$_2$CF$_3$ or OSO$_2$Ph, can be prepared by reaction of intermediates of Formula XXXVIII by treatment with isocyanates of Formula XLIII, in the presence of base, such as NaH or DBU.

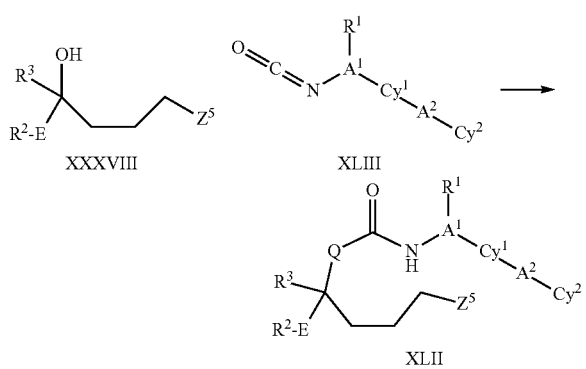

In a fourth process, compounds of Formula I, wherein Q is O, can be prepared by subjecting carbonates of Formula XLIV, wherein R$^b$ is lower alkyl or phenyl, to base in an inert solvent at from about 20° C. to about 175° C.

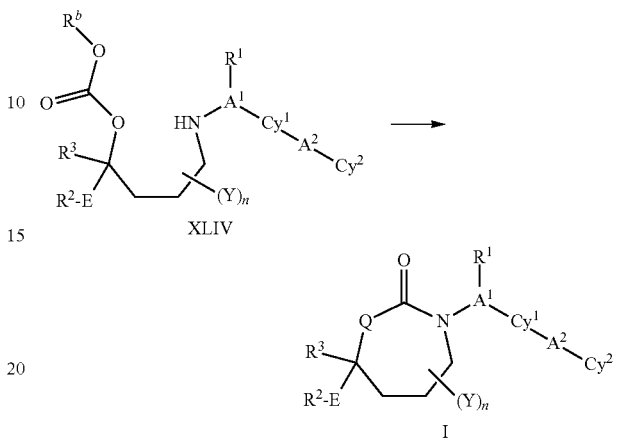

Carbonates of Formula XLIV can be prepared by deprotection of precursors such as XLV.

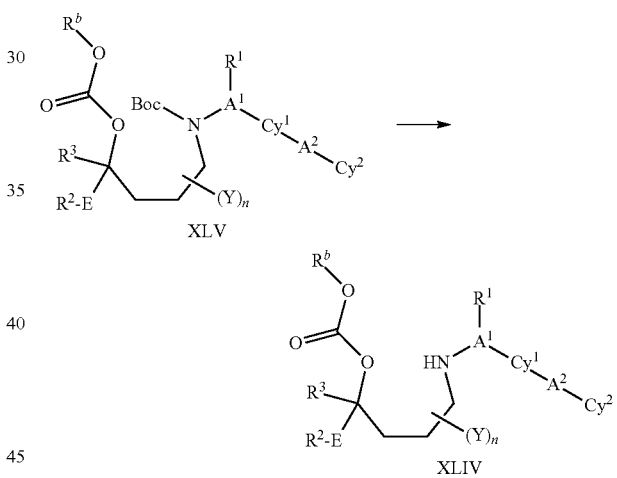

In a fifth process a compound of Formula I can be prepared from another compound of Formula I. For example:

(1) a compound of Formula I wherein Cy$^1$ is substituted with bromine or iodine, A$^2$ is a bond and Cy$^2$ is hydrogen can be reacted with an optionally substituted aryl or heteroarylboronic acid or ester in the presence of a palladium catalyst to give a compound of Formula I wherein A$^2$ is a bond and Cy$^2$ is optionally substituted aryl or heteroaryl.

(2) a compound of Formula I wherein R$^1$ or R$^3$ is ω-hydroxy(C$_2$-C$_6$)alkyl can be oxidized to a compound of Formula I wherein R$^1$ or R$^3$ is ω-carboxy(C$_1$-C$_5$)alkyl using Jones reagent.

(3) a compound of Formula I wherein R$^1$ or R$^3$ is ω-carboxy(C$_1$-C$_6$)alkyl can be coupled with ammonia or a (C$_1$-C$_6$) alkylamine using a standard peptide coupling reagent such as EDC to afford a compound of Formula I wherein R$^1$ or R$^3$ is ω-H$_2$NC(=O)(C$_1$-C$_6$)alkyl or ω-{(C$_1$-C$_6$)alkylNHC(=O)} (C$_1$-C$_6$)alkyl.

(4) a compound of Formula I wherein R$^1$ or R$^3$ is ω-hydroxy(C$_1$-C$_6$)alkyl can be converted to its methanesulfonate or trifluoromethanesulfonate, treated with sodium azide and reduced to give a compound of Formula I, wherein $R^1$ or $R^3$ is ω-amino($C_1$-$C_6$)alkyl.

(5) a compound of Formula I wherein $R^1$ or $R^3$ is amino ($C_1$-$C_6$)alkyl can be reacted with acetic anhydride or acetyl chloride to give a compound of Formula I wherein $R^1$ or $R^3$ is {acetylamino}($C_1$-$C_6$)alkyl.

(6) a compound of Formula I wherein $R^1$ or $R^3$ is amino ($C_1$-$C_6$)alkyl can be reacted with methanesulfonyl chloride to give a compound of Formula I wherein $R^1$ or $R^3$ is {methanesulfonylamino}($C_1$-$C_6$)alkyl.

(7) a compound of Formula I, wherein $R^1$ is ($C_2$-$C_6$)alkenyl, is hydroborated to afford a compound of Formula I wherein $R^1$ is hydroxy($C_2$-$C_6$)alkyl, (8) a compound of Formula I, wherein $R^3$ is ($C_2$-$C_6$)alkenyl, is hydroborated to afford a compound of Formula I wherein $R^3$ is hydroxy($C_2$-$C_6$)alkyl.

(9) a compound of Formula I, wherein $R^1$ is ($C_2$-$C_6$)alkenyl, can be reacted with osmium tetroxide and N-methylmorpholine-N-oxide to afford a compound of Formula I wherein $R^1$ is vicinal dihydroxy($C_2$-$C_6$)alkyl,

(10) a compound of Formula I, wherein $R^3$ is ($C_2$-$C_6$) alkenyl, can be reacted with osmium tetroxide and N-methylmorpholine-N-oxide to afford a vicinal diol compound of Formula I wherein $R^3$ is vicinal dihydroxy($C_2$-$C_6$)alkyl.

(11) a compound of Formula I, wherein $R^1$ is $H_2C=CH$ ($C_0$-$C_4$)alkyl-, can be reacted with ozone followed by $NaBH_4$ to give a compound of Formula I wherein $R^1$ is ω-hydroxy ($C_1$-$C_5$)alkyl.

(12) a compound of Formula I, wherein $R^3$ is $H_2C=CH$ (C0—$C_4$)alkyl-, can be reacted with ozone followed by $NaBH_4$ to give a compound of Formula I wherein $R^3$ is ω-hydroxy($C_1$-$C_5$)alkyl.

(13) a compound of Formula I wherein $R^1$ or $R^3$ is amino ($C_1$-$C_6$)alkyl can be reacted with an ($C_1$-$C_6$)alkyl isocyanate to give a compound of Formula I wherein $R^1$ or $R^3$ is ($C_1$-$C_6$) alkylaminocarbonylamino($C_1$-$C_6$)alkyl.

(14) a compound of Formula I wherein $R^1$ or $R^3$ is amino ($C_1$-$C_6$)alkyl can be reacted with an ($C_1$-$C_6$)alkyl chloroformate to give a compound of Formula I wherein $R^1$ or $R^3$ is ($C_1$-$C_6$)alkoxycarbonylamino($C_1$-$C_6$)alkyl.

(15) a compound of Formula I wherein $R^1$ or $R^3$ is amino ($C_1$-$C_6$)alkyl can be reacted with chlorosulfonyl isocyanate or sulfamide to give a compound of Formula I wherein $R^1$ or $R^3$ is aminosulfonylamino($C_1$-$C_6$)alkyl.

(16) a compound of Formula I wherein $R^1$ or $R^3$ is amino ($C_1$-$C_6$)alkyl can be reacted with a ($C_1$-$C_6$)alkylsulfamoyl chloride to give a compound of Formula I wherein $R^1$ or $R^3$ is ($C_1$-$C_6$)alkylaminosulfonylamino($C_1$-$C_6$)alkyl.

(17) a compound of Formula I wherein $R^1$ or $R^3$ is hydroxy ($C_1$-$C_6$)alkyl can be reacted with chlorosulfonyl isocyanate to give a compound of Formula I wherein $R^1$ or $R^3$ is aminosulfonyloxy($C_1$-$C_6$)alkyl.

(18) a compound of Formula I wherein $R^1$ or $R^3$ is hydroxy ($C_1$-$C_6$)alkyl can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I wherein $R^1$ or $R^3$ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy($C_1$-$C_6$) alkyl.

(19) a compound of Formula I wherein $R^1$ or $R^3$ is hydroxy ($C_1$-$C_6$)alkyl can be reacted with $POCl_3$ to give a compound of Formula I wherein $R^1$ or $R^3$ is $(HO)_2P(=O)O(C_1$-$C_6)$ alkyl.

(20) a compound of Formula I wherein $Cy^1$ is substituted with bromine or iodine, $A^2$ is a bond and $Cy^2$ is hydrogen can be reacted with a cyclic amine in the presence of a palladium catalyst to give a compound of Formula I wherein $A^2$ is a bond and $Cy^2$ is a cyclic amino moiety attached through its nitrogen atom.

(21) a compound of Formula I wherein Q is $NR^5$ and $R^5$ is H can be reacted with an ($C_1$-$C_6$)alkyl halide in the presence of a strong base such as sodium hydride to afford a compound of Formula I wherein Q is $NR^5$ and $R^5$ is ($C_1$-$C_6$)alkyl.

(22) a compound of Formula I wherein $R^1$ or $R^3$ is ω-$H_2NCO$($C_1$-$C_5$)alkyl can be reacted with TFAA in the presence of pyridine to afford a compound of Formula I wherein $R^1$ or $R^3$ is ω-cyano($C_1$-$C_5$)alkyl.

(23) a compound of Formula I, wherein $R^1$ or $R^3$ is ω-$MeO_2C$($C_1$-$C_5$)alkyl can be reacted with at least 2 equivalents of MeMgBr to afford a compound of Formula I, wherein $R^1$ or $R^3$ is $HOC(Me)_2$($C_1$-$C_5$)alkyl.

(24) a compound of Formula I wherein $R^1$ or $R^3$ is ω-hydroxy($C_1$-$C_6$)alkyl can be converted to its methanesulfonate or trifluoromethanesulfonate and reacted with morpholine to give a compound of Formula I, wherein $R^1$ or $R^3$ is ω-(4-morpholino)($C_1$-$C_6$)alkyl.

Purification Methods

Compounds of the invention can be purified by high pressure liquid chromatography (prep HPLC). Unless otherwise specified, prep HPLC refers to preparative reverse phase HPLC on a C-18 column eluted with a water/acetonitrile gradient containing 0.01% TFA run on a Gilson 215 system.

LC-MS Methods

Method 1 [LC-MS (3 min)]
Column: Chromolith SpeedRod, RP-18e, 50×4.6 mm; Mobil phase: A: 0.01% TFA/water, B: 0.01% TFA/$CH_3CN$; Flow rate: 1 mL/min; Gradient:

| Time (min) | A % | B % |
| --- | --- | --- |
| 0.0 | 90 | 10 |
| 2.0 | 10 | 90 |
| 2.4 | 10 | 90 |
| 2.5 | 90 | 10 |
| 3.0 | 90 | 10 |

Method 2 [LC-MS (16 min)]
Column: Chromolith SpeedRod, RP-18e, 50×4.6 mm; Mobil phase: A: 0.01% TFA/water, B: 0.01% TFA/$CH_3CN$; Flow rate: 1 mL/min; Gradient:

| Time (min) | A % | B % |
| --- | --- | --- |
| 0.0 | 90 | 10 |
| 14.0 | 10 | 90 |
| 15.0 | 10 | 90 |
| 15.1 | 90 | 10 |
| 16.0 | 90 | 10 |

Method 3 [30-90]

| | |
| --- | --- |
| Column | YMC-PACK ODS-AQ, 50 × 2.0 mm 5 μm |
| Mobile Phase | A: water (4 L) + TFA (1.5 mL)) B: acetonitrile (4 L) + TFA (0.75 mL)) |

-continued

| | TIME (min) | A % | B % |
|---|---|---|---|
| | 0 | 70 | 30 |
| | 2.2 | 10 | 90 |
| | 2.5 | 10 | 90 |
| Flow Rate | 1 mL/min | | |
| Wavelength | UV220 | | |
| Oven Temp | 50° C. | | |
| MS ionization | ESI | | |

Method 4 [10-80]

| Column | YMC-PACK ODS-AQ, 50 × 2.0 mm 5 μm | | |
|---|---|---|---|
| Mobile Phase | A: water (4 L) + TFA (1.5 mL)) | | |
| | B: acetonitrile (4 L) + TFA (0.75 mL)) | | |
| | TIME (min) | A % | B % |
| | 0 | 90 | 10 |
| | 2.2 | 20 | 80 |
| | 2.5 | 20 | 80 |
| Flow Rate | 1 mL/min | | |
| Wavelength | UV 220 nm | | |
| Oven Temp | 50° C. | | |
| MS ionization | ESI | | |

EXAMPLE 1

(S)-1-((S)-1-(4-bromophenyl)ethyl)-4-(3-hydroxypropyl)-4-phenyl-1,3-diazepan-2-one

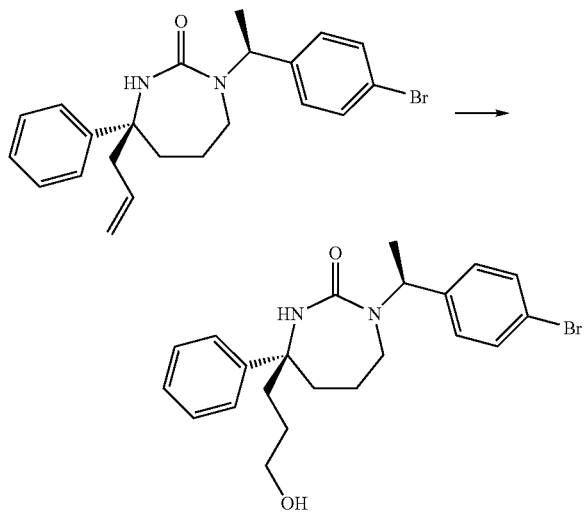

A stirred solution of (S)-4-allyl-1-((S)-1-(4-bromophenyl)ethyl)-4-phenyl-1,3-diazepan-2-one (70 mg, 0.17 mmol) in dry THF (2 mL) was cooled in an ice bath and 0.5 M disiamylborane (2 mL, 1.0 mmol) was added dropwise over 2 min The ice bath was allowed to melt and the mixture was stirred overnight at rt. Water (5 mL) was added, followed by solid $NaBO_3 \cdot H_2O$ (180 mg, 1.8 mmol). The mixture was stirred at rt for 2 h and concentrated. The aqueous residue was extracted with EtOAc (2×60 mL). The combined EtOAc extracts were dried over $Na_2SO_4$ and concentrated to afford an oil (94 mg). Preparative HPLC afforded (S)-1-((S)-1-(4-bromophenyl)ethyl)-4-(3-hydroxypropyl)-4-phenyl-1,3-diazepan-2-one (47 mg, 64%) as an oil. LC-MS Method 2 $t_R$=8.55 min, m/z=433, 431. $^1$H NMR (CDCl$_3$) 1.23 (m, 1H), 1.44 (d, 3H), 1.52 (m, 3H), 1.81 (m, 2H), 1.95 (m, 1H), 2.39 (m, 1H), 2.80 (m, 2H), 3.57 (m, 2H), 4.38 (1H), 5.30 (q, 1H), 5.90 (1H), 6.68 (d, 2H), 7.23 (d, 2H), 7.33 (m, 1H), 7.40 (4H).

EXAMPLE 2

(S)-4-allyl-1-((S)-1-(4-bromophenyl)ethyl)-4-phenyl-1,3-diazepan-2-one and (R)-4-allyl-1-((S)-1-(4-bromophenyl)ethyl)-4-phenyl-1,3-diazepan-2-one

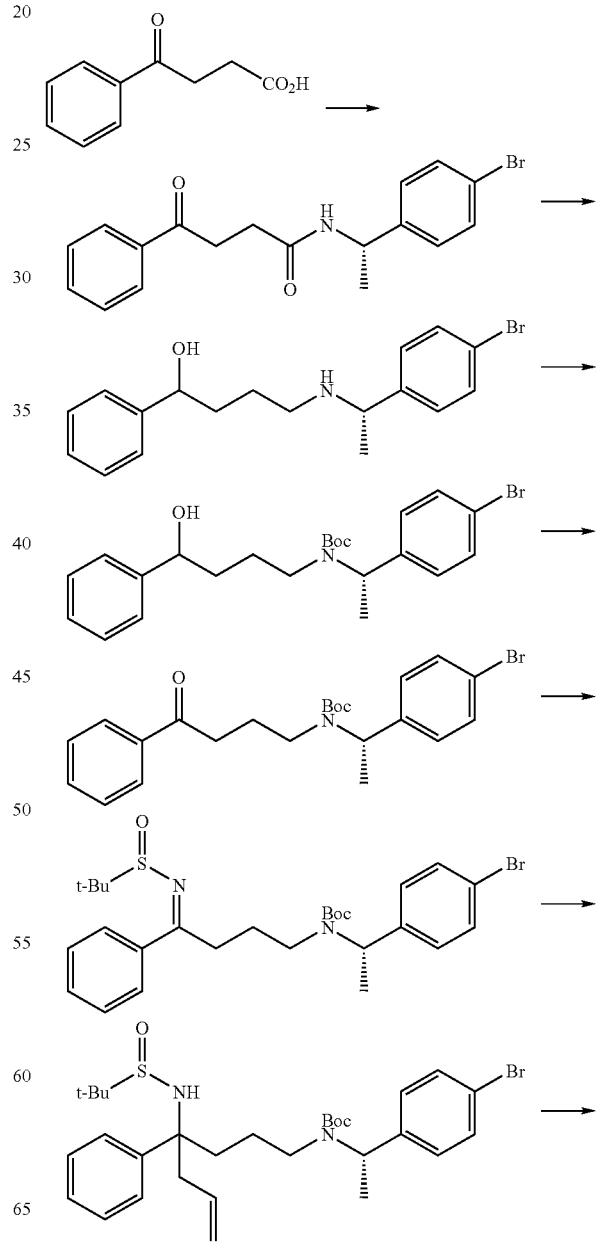

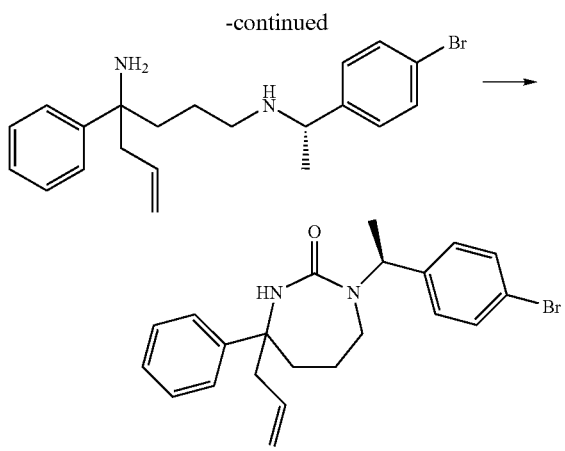

Step 1

To a stirred solution of benzoylpropionic acid (2.00 g, 11.2 mmol), (S)-1-(4-bromophenyl)ethanamine (2.25 g, 11.2 mmol), HOBt (1.72 g, 11.2 mmol) and i-Pr$_2$NEt (2.2 mL, 12.3 mmol) in CH$_2$Cl$_2$ (40 mL) was added EDC.HCl (2.37 g, 12.3 mmol). The mixture was stirred at rt for 4 h and diluted with EtOAc (140 mL) and 5% aq HCl (50 mL). The mixture was filtered and (S)—N-(1-(4-bromophenyl)ethyl)-4-oxo-4-phenylbutanamide (3.80 g, 93%) was collected as a white solid. $^1$H NMR (d$_6$-DMSO) δ 1.28 (d, 3H), 2.50 (m, 2H), 3.19 (m, 2H), 4.82 (m, 1H), 7.23 (d, 2H), 7.47 (4H), 7.59 (m, 1H), 7.92 (d, 2H), 8.38 (d, 1H).

Step 2

A 250-mL RBF equipped with a magnetic stirbar was charged with solid (S)—N-(1-(4-bromophenyl)ethyl)-4-oxo-4-phenylbutanamide (2.85 g, 7.9 mmol) and placed in an ice bath. To the stirred solid was added 1.0 M BH$_3$ in THF (30 mL, 30 mmol). The ice bath was removed and the mixture was stirred at rt for 2.5 h. The mixture was poured into 5% aq HCl (100 mL) and concentrated under reduced pressure to remove the THF. The aqueous residue was basified to pH 14 by portionwise addition of NaOH pellets. The mixture was extracted with CH$_2$Cl$_2$ (2×100 mL). The combined CH$_2$Cl$_2$ extracts were dried over Na$_2$SO$_4$. Removal of the solvent afforded crude 4-((S)-1-(4-bromophenyl)ethylamino)-1-phenylbutan-1-ol (2.58 g, 94%) as an oil. LC-MS Method 1 t$_R$=1.20 min, m/z=348, 350.

Step 3

To a stirred solution of crude 4-((S)-1-(4-bromophenyl) ethylamino)-1-phenylbutan-1-ol (2.46 g, 7.1 mmol) in THF (40 mL) was added 10% aq K$_2$CO$_3$ (40 mL), followed by di-t-butyl dicarbonate (1.90 g, 8.5 mmol). The mixture was stirred overnight at rt and concentrated to remove THF. The aqueous residue was extracted with EtOAc (2×80 mL). The combined EtOAc extracts were washed with brine (40 mL) and dried over MgSO$_4$. Removal of the solvent left tert-butyl (S)-1-(4-bromophenyl)ethyl(4-hydroxy-4-phenylbutyl)carbamate (3.24 g, quant). LC-MS Method 1 t$_R$=1.20 min, m/z=472, 470, 350, 348.

Step 4

To a stirred solution of tert-butyl (S)-1-(4-bromophenyl) ethyl(4-hydroxy-4-phenylbutyl)carbamate (3.24 g, 7.1 mmol) in CH$_2$Cl$_2$ (20 mL) at rt was added 15% Dess-Martin periodinane solution in CH$_2$Cl$_2$ (23 mL, 10.8 mmol). The mixture was stirred overnight at rt. Satd aq NaHCO$_3$ (50 mL) was added and the mixture was stirred for 10 min Solid Na$_2$S$_2$O$_3$ (5 g) was added and stirring was continued for 1 h. The mixture was extracted with CH$_2$Cl$_2$ (2×100 mL) and the combined organic layer was washed with brine (35 mL) and dried over Na$_2$SO$_4$. Removal of the solvent left an amber oil (3.19 g) which was purified by chromatography on a 40-g silica cartridge eluted with a 0-100% EtOAc in hexanes gradient to afford (S)-tert-butyl 1-(4-bromophenyl)ethyl(4-oxo-4-phenylbutyl)carbamate (2.32 g, 72%) as a yellow oil. LC-MS Method 1 t$_R$=2.40 min, m/z=470, 468, 348, 346.

Step 5

A stirred mixture of (S)-tert-butyl 1-(4-bromophenyl)ethyl (4-oxo-4-phenylbutyl)carbamate (2.16 g, 4.84 mmol), t-BuSONH$_2$ (586 mg, 4.84 mmol), Ti(OEt)$_4$ (2.21 g, 9.67 mmol) and dry THF (30 mL) was heated at reflux for 24 h. The mixture was concentrated and the residue was diluted with EtOAc (90 mL) and brine (30 mL). The mixture was filtered through Celite and the organic layer of the filtrate was separated, washed with brine (20 mL) and dried over Na$_2$SO$_4$. Removal of the solvent afforded a yellow oil (2.39 g) which was purified by chromatography on silica gel to afford tert-butyl (S)-1-(4-bromophenyl)ethyl(4-(tert-butylsulfinylimino)-4-phenylbutyl)carbamate (1.35 g, 51%) as a yellow solid. LC-MS Method 1 t$_R$=2.45 min, m/z=551, 549.

Step 6

A stirred solution of tert-butyl (S)-1-(4-bromophenyl)ethyl (4-(tert-butylsulfinylimino)-4-phenylbutyl)carbamate (926 mg, 1.69 mmol) in dry THF (25 mL) was cooled in a dry ice/i-PrOH bath and 1 M allylmagnesium bromide (4.2 mL, 4.2 mmol) was added dropwise over 2 min The mixture was stirred in the cooling bath for 3 h, diluted with satd aq NH$_4$Cl (50 mL) and extracted with EtOAc (2×50 mL). The combined EtOAc extracts were washed with brine (15 mL), dried over Na$_2$SO$_4$ and concentrated to afford tert-butyl (S)-1-(4-bromophenyl)ethyl(4-(1,1-dimethylethylsulfinamido)-4-phenylhept-6-enyl)carbamate (990 mg, 99%) as an oil. LC-MS Method 1 t$_R$=2.47 min, m/z=593, 591.

Step 7

To an ice-cold, stirred solution of tert-butyl (S)-1-(4-bromophenyl)ethyl(4-(1,1-dimethylethylsulfinamido)-4-phenylhept-6-enyl)carbamate (990 mg, 1.67 mmol) in CH$_2$Cl$_2$ (5 mL) was added 4 M HCl in dioxane (10 mL, 40 mmol). The mixture was stirred overnight at rt and concentrated to afford an off-white solid (940 mg). The solid was redissolved in 5% aq HCl (25 mL), washed with ether (75 mL) and basified with NaOH. The basic aqueous solution was extracted with CH$_2$Cl$_2$ (2×60 mL). The combined CH$_2$Cl$_2$ extracts were dried over Na2SO4 and concentrated to afford N$^1$—((S)-1-(4-bromophenyl)ethyl)-4-phenylhept-6-ene-1,4-diamine (522 mg, 80%) as an oil. LC-MS Method 1 t$_R$=0.97 min, m/z=389, 387.

Step 8

To a stirred, ice-cold solution of N$^1$—((S)-1-(4-bromophenyl)ethyl)-4-phenylhept-6-ene-1,4-diamine (284 mg, 0.73 mmol) in CH$_2$Cl$_2$ (50 mL) was added i-Pr$_2$NEt (0.39 mL, 2.2 mmol), followed by a solution of triphosgene (72 mg, 0.24 mmol) in CH$_2$Cl$_2$ (4 mL). The mixture was allowed to warm to rt and stirred overnight. The mixture was concentrated and the residue was taken up in ether (90 mL) and 5% aq HCl (20 mL). The organic layer was separated, washed with brine, dried over Na$_2$SO$_4$ and concentrated to leave a 1:1 mixture of the diastereomers of 4-allyl-1-((S)-1-(4-bromophenyl) ethyl)-4-phenyl-1,3-diazepan-2-one (292 mg). This material was combined with product from another similar reaction (total weight 554 mg). Chromatography on a 40-g silica gel cartridge eluted with a 0-60% EtOAc in hexanes gradient afforded the two diastereomers of 4-allyl-1-((S)-1-(4-bromophenyl)ethyl)-4-phenyl-1,3-diazepan-2-one.

Isomer 1: (R)-4-allyl-1-((S)-1-(4-bromophenyl)ethyl)-4-phenyl-1,3-diazepan-2-one (160 mg, 29%). LC-MS Method 1 $t_R$=2.20 min, m/z=415, 413. $^1$H NMR (CDCl$_3$) [selected resonances] 1.22 (d, 3H), 5.51 (q, 1H).

Isomer 2: (S)-4-allyl-1-((S)-1-(4-bromophenyl)ethyl)-4-phenyl-1,3-diazepan-2-one (154 mg, 28%). LC-MS Method 1 $t_R$=2.20 min, m/z=415, 413. $^1$H NMR (CDCl$_3$) 1.15 (m, 1H), 1.39 (m, 1H), 1.43 (d, 3H), 1.84 (m, 1H), 2.40 (m, 2H), 2.45 (m, 1H), 2.78 (m, 2H), 4.99 (s, 1H), 4.18 (m, 2H), 5.26 (q, 1H), 5.43 (m, 1H), 6.62 (d, 2H), 7.18 (d, 2H), 7.28 (m, 1H), 7.39 (m, 4H).

EXAMPLE 3

Isomer 1: (R)-1-((S)-1-(4-bromophenyl)ethyl)-4-(2-hydroxyethyl)-4-phenyl-1,3-diazepan-2-one

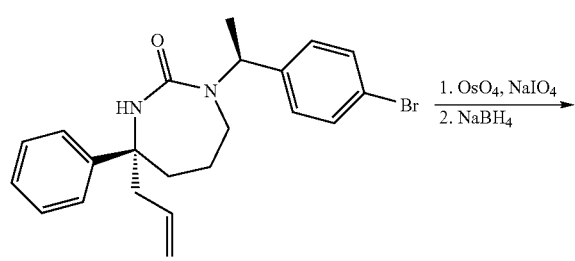

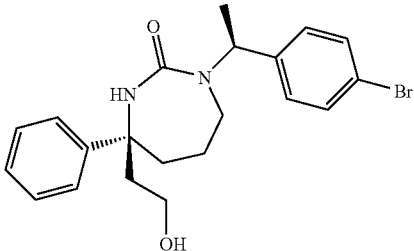

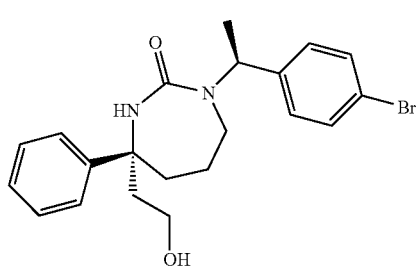

To a stirred solution of (R)-4-allyl-1-((S)-1-(4-bromophenyl)ethyl)-4-phenyl-1,3-diazepan-2-one (51 mg, 0.12 mmol) in THF (2 mL) and water (2 mL) were added NaIO$_4$ (132 mg, 0.62 mmol) and 2.5% OSO$_4$ in t-BuOH (0.032 mL, 0.003 mmol). The mixture was stirred at rt for 5 h and concentrated under reduced pressure. The residue was partitioned between EtOAc (90 mL) and brine (20 mL). The organic layer was concentrated and the residue was dissolved in MeOH (20 mL). The solution was cooled in an ice bath and NaBH$_4$ (50 mg) was added. The mixture was stirred overnight and concentrated. The residue was taken up in EtOAc (90 mL), washed with 5% aq HCl (20 mL) and satd aq NaHCO$_3$ (20 mL), and dried over Na$_2$SO$_4$. Removal of the solvent left an oil (43 mg) which was purified by prep HPLC to afford (R)-1-((S)-1-(4-bromophenyl)ethyl)-4-(2-hydroxyethyl)-4-phenyl-1,3-diazepan-2-one (19 mg, 37%) as an oil. LC-MS Method 2 $t_R$=8.7 min, m/z=419, 417; $^1$H NMR (CDCl$_3$) δ 1.0-1.2 (2H), 1.23 (d, 3H), 1.77 (m, 1H), 2.01 (m, 1H), 2.24 (m, 2H), 2.66 (m, 1H), 2.89 (m, 1H), 3.45 (m, 1H), 3.72 (m, 1H), 4.10 (br s, 1H), 5.50 (q, 1H), 6.79 (s, 1H), 7.24 (3H), 7.37 (2H), 7.43 (4H)

Isomer 2: (S)-1-((S)-1-(4-bromophenyl)ethyl)-4-(2-hydroxyethyl)-4-phenyl-1,3-diazepan-2-one The title compound was prepared from (S)-4-allyl-1-((S)-1-(4-bromophenyl)ethyl)-4-phenyl-1,3-diazepan-2-one following a procedure analogous to that described immediately above. $^1$H NMR (CDCl$_3$) δ 1.1-1.25 (2H), 1.42 (d, 3H), 1.77 (m, 1H), 1.99 (m, 1H), 2.20 (m, 1H), 2.38 (m, 1H), 2.78 (m, 2H), 3.54 (m, 1H), 3.74 (m, 1H), 5.30 (q, 1H), 6.68 (d, 2H), 7.20 (d, 2H), 7.3-7.5 (5H)

EXAMPLE 4

(4S)-1-((S)-1-(4-bromophenyl)ethyl)-4-(2-hydroxypropyl)-4-phenyl-1,3-diazepan-2-one

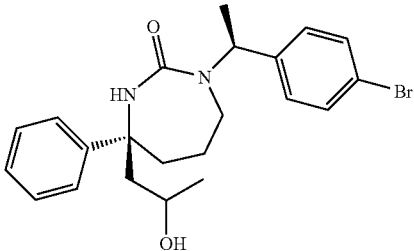

The title compound was isolated as a minor byproduct from the procedure described in Example 1. $^1$H NMR (CDCl$_3$) δ [selected resonances] 1.16 (d, 3H), 1.2-1.3 (2H), 1.46 (d, 3H), 4.11 (m, 1H), 5.29 (q, 1H)

EXAMPLE 5

3-((S)-1-((S)-1-(4-bromophenyl)ethyl)-2-oxo-4-phenyl-1,3-diazepan-4-yl)propanamide

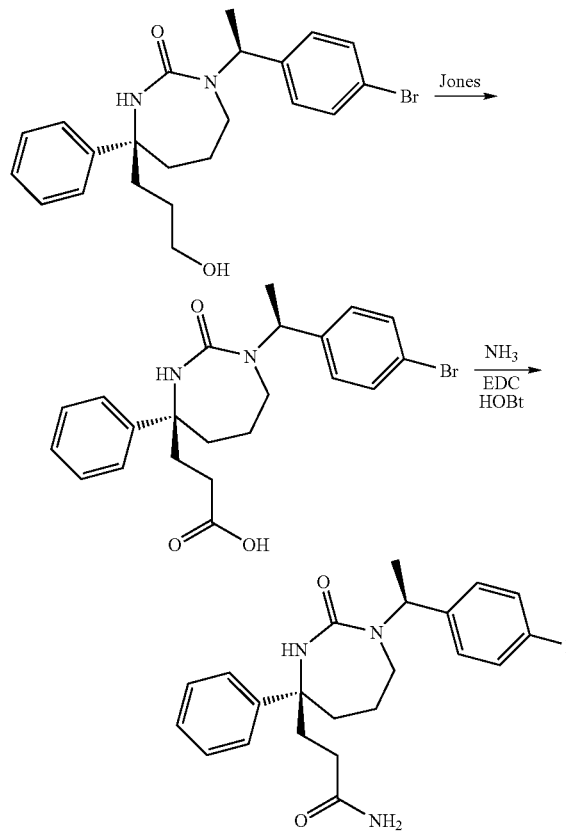

Step 1

A stirred mixture of Jones reagent (0.25 mL) and acetone (2 mL) was cooled in an ice bath and a solution of (S)-1-((S)-1-(4-bromophenyl)ethyl)-4-(3-hydroxypropyl)-4-phenyl-1,3-diazepan-2-one (45 mg, 0.11 mmol) in acetone (6 mL) was added dropwise over 10 min The mixture was stirred in the ice bath for 2 h and i-PrOH (2 mL) was added. The mixture was concentrated under reduced pressure. The residue was taken up in EtOAc (100 mL), washed with water (15 mL) and brine (15 mL), and dried over Na$_2$SO$_4$. Removal of the solvent afforded crude 3-((S)-1-((S)-1-(4-bromophenyl)ethyl)-2-oxo-4-phenyl-1,3-diazepan-4-yl)propanoic acid (33 mg, 69%) which was used without further purification.

Step 2

A stirred solution of 3-((S)-1-((S)-1-(4-bromophenyl)ethyl)-2-oxo-4-phenyl-1,3-diazepan-4-yl)propanoic acid (33 mg, 0.067 mmol), HOBt.H$_2$O (58 mg, 0.38 mmol), i-Pr$_2$NEt (0.14 mL, 0.76 mmol) in CH$_2$Cl$_2$ (9 mL) was cooled in an ice bath. 0.5 M NH$_3$ in dioxane (0.8 mL, 0.4 mmol) was added, followed by EDC.HCl (73 mg, 0.38 mmol). The mixture was allowed to warm to rt and stirred for 3 d. The mixture was diluted with EtOAc (80 mL), washed with 5% aq HCl (20 mL) and brine (20 mL). The combined aqueous washes were back extracted with EtOAc (20 mL). The combined EtOAc layer was dried over Na2SO4 and concentrated t leave an oil (34 mg). This oil was dissolved in THF (2 mL) and conc NH$_4$OH (1 mL). The mixture was stirred overnight at rt and heated in the microwave at 100° C. for 30 min and at 120° C. for 30 min The mixture was concentrated and the residue was purified by prep HPLC to afford 3-((S)-1-((S)-1-(4-bromophenyl)ethyl)-2-oxo-4-phenyl-1,3-diazepan-4-yl)propanamide (0.5 mg, 1%). LC-MS Method 1 $t_R$=1.73 min, m/z=446, 444; $^1$H NMR (CDCl$_3$) δ [selected resonances] 1.50 (d, 3H), 5.30 (q, 1H), 6.73 (d, 2H)

EXAMPLE 6

(S)-4-(2-hydroxyethyl)-1-((S)-1-(4-(6-methoxypyridin-3-yl)phenyl)ethyl)-4-phenyl-1,3-diazepan-2-one

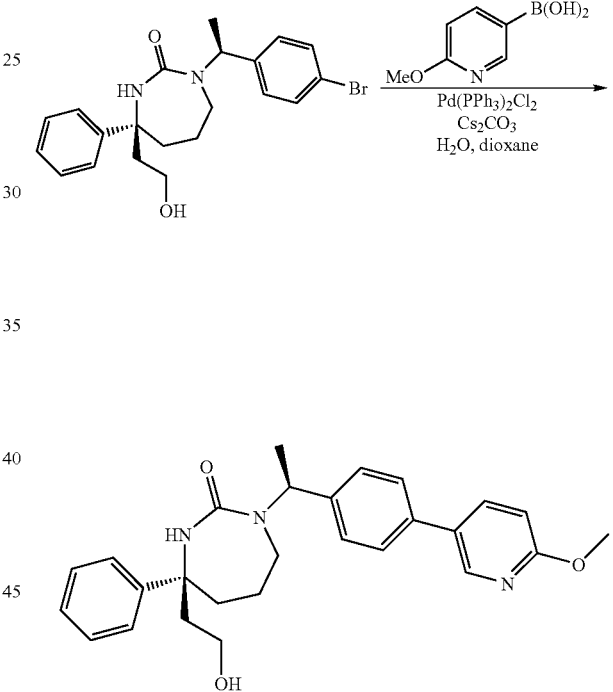

A microwave vial was charged with (S)-1-((S)-1-(4-bromophenyl)ethyl)-4-(2-hydroxyethyl)-4-phenyl-1,3-diazepan-2-one (7 mg, 0.017 mmol), 6-methoxypyridine-3-boronic acid (10.6 mg, 0.069 mmol), Cs$_2$CO$_3$ (180 mg, 0.55 mmol), PdCl$_2$(PPh$_3$)$_2$ (3.0 mg, 0.004 mmol), water (0.75 mmol) and dioxane (1.5 mL). The mixture was sparged with N$_2$ for 15 min and heated at 120° C. in the microwave for 0.5 h. The mixture was diluted with H$_2$O (5 mL) and applied to a 10-mL ChemElut cartridge. After standing for 5 min, the cartridge was eluted with EtOAc (50 mL). The eluate was concentrated to leave a brown oil (13 mg) which was purified by prep HPLC to afford (S)-4-(2-hydroxyethyl)-1-((S)-1-(4-(6-methoxypyridin-3-yl)phenyl)ethyl)-4-phenyl-1,3-diazepan-2-one (4.0 mg, 52%). LC-MS Method 1 $t_R$=1.82 min, m/z=446; $^1$H NMR (CDCl$_3$) δ 1.26 (m, 1H), 1.52 (m, 1H), 1.54 (d, 3H), 1.82 (m, 1H), 2.1-2.3 (2H), 2.42 (m, 1H), 2.8-3.0

(m, 2H), 3.51 (m, 1H), 3.72 (m, 1H), 3.99 (s, 3H), 5.52 (q, 1H), 6.83 (d, 1H), 7.03 (d, 2H), 7.30 (d, 3H), 7.43 (4H), 7.78 (d, 1H), 8.37 (s, 1H).

EXAMPLE 7

(S)-1-((S)-1-(4-bromophenyl)ethyl)-4-(2-methylallyl)-4-phenyl-1,3-diazepan-2-one

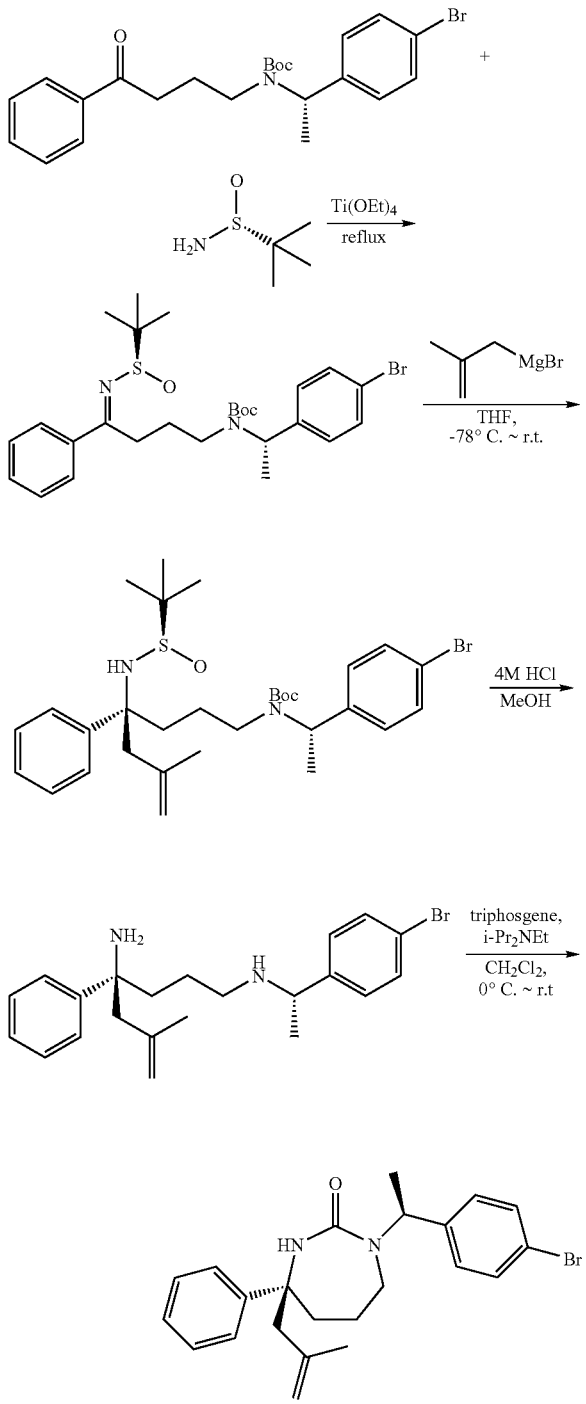

Step 1

(S)-tert-butyl 1-(4-bromophenyl)ethyl(4-oxo-4-phenylbutyl)carbamate (3.14 g, 7.04 mmol), (R)-t-Butylsulfinamide, Ti(OEt)$_4$ (125 μL, 1.5 equiv) were mixed with dry THF (80 mL) and heated at reflux for overnight. LC-MS found most of starting material was consumed. The mixture was diluted with ether (200 mL), washed with water (50 mL), brine (30 mL), dried over Na$_2$SO$_4$. After filtration and concentration, the residue was purified by chromatography on a 120-g silica gel cartridge, eluted with a 10~35% EtOAc in hexanes gradient, to afford tert-butyl (S)-1-(4-bromophenyl)ethyl((E)-4-((R)-tert-butylsulfinylimino)-4-phenylbutyl)carbamate (1.97 g, 51%) product and recovered starting material (0.72 g). LC-MS Method 1 $t_R$=2.43 min, m/z 549, 551 (M+1)

Step 2

A solution of tert-butyl (S)-1-(4-bromophenyl)ethyl((E)-4-((R)-tert-butylsulfinylimino)-4-phenylbutyl)carbamate (1.97 g, 3.59 mmol) in dry THF (60 mL) was cooled to −78° C. A solution of 2-methylallylmagnesium chloride (0.5M in THF, 14.4 mL, 2 equiv) was added slowly. After 2 h, the mixture was warmed to rt and stirred for 1 h. LC-MS found reaction completed. The mixture was quenched with satd aq NH$_4$Cl (10 mL), diluted with ether (100 mL), washed with water (30 mL), brine (25 mL), dried over Na$_2$SO$_4$. Filtration and concentration gave crude tert-butyl (S)-1-(4-bromophenyl)ethyl((S)-4-((R)-1,1-dimethylethylsulfinamido)-6-methyl-4-phenylhept-6-enyl)carbamate (2.30 g) which was used for next steps without further purifications. LC-MS Method 1 $t_R$=2.53 min, m/z 605, 607(M+1).

Step 3

Crude tert-butyl (S)-1-(4-bromophenyl)ethyl((S)-4-((R)-1,1-dimethylethylsulfinamido)-6-methyl-4-phenylhept-6-enyl)carbamate (1.5 g, 2.48 mmol) was dissolved in 1M HCl in methanol solution (120 mL, mixed from 4M HCl in 1,4-Dioxane solution and methanol). The mixture was stirred for 3 h at rt. LC-MS found the reaction completed. The mixture was basified with KOH, concentrated to remove methanol and extracted with CH$_2$Cl$_2$ (3×25 mL). The combined organic layers were washed with brine (20 mL) and dried over Na$_2$SO$_4$. After filtration and concentration, crude (S)—N$^1$—((S)-1-(4-bromophenyl)ethyl)-6-methyl-4-phenylhept-6-ene-1,4-diamine HCl salt 0.92 g, 93%) was left as a brown oil, which was used for in the next step without further purifications. LC-MS Method 1 $t_R$=1.07 min, m/z 401, 403(M+1).

Step 4

A solution of (S)—N$^1$—((S)-1-(4-bromophenyl)ethyl)-6-methyl-4-phenylhept-6-ene-1,4-diamine HCl salt (0.88 g, 2.2 mmol) in CH$_2$Cl$_2$ (120 mL) was cooled to 0° C. and i-Pr$_2$NEt (1.15 mL, 3 equiv) was added. A solution of triphosgene (215 mg, 0.33 equiv) in CH$_2$Cl$_2$ (15 mL) was added dropwise over 10 min The mixture was stirred for 3 h at 0° C. LC-MS found the reaction completed. The mixture was concentrated, redissolved in 6:1 Ether/EtOAc (70 mL), washed with 1% aq HCl (2×15 mL), satd aq NaHCO$_3$ (10 mL) and brine (10 mL), and dried over over Na$_2$SO$_4$. After filtration and concentration, the residue was purified by chromatography on a 40-g silica gel cartridge, eluted with a 5~40% EtOAc in Hexanes gradient, to afford (S)-1-((S)-1-(4-bromophenyl)ethyl)-4-(2-methylallyl)-4-phenyl-1,3-diazepan-2-one (487 mg, 52%) as a clear oil. LC-MS Method 1 $t_R$=2.25 min, m/z 427, 429 (M+1); $^1$H NMR (CDCl$_3$) δ 7.42 (d, 2H), 7.35 (t, 2H), 7.28-7.20 (m, 3H), 6.76 (d, 2H), 5.37 (q, 1H), 5.21 (s, 1h), 4.98 (s, 1H), 4.85 (s, 1H), 2.78 (m, 2H), 2.44 (m, 3H), 1.89 (td, 1H), 1.43 (d, 3H), 1.24 (m, 1H), 1.11 (s, 3H).

EXAMPLE 8

(S)-1-((S)-1-(4-bromophenyl)ethyl)-4-(2-hydroxy-2-methylpropyl)-4-phenyl-1,3-diazepan-2-one

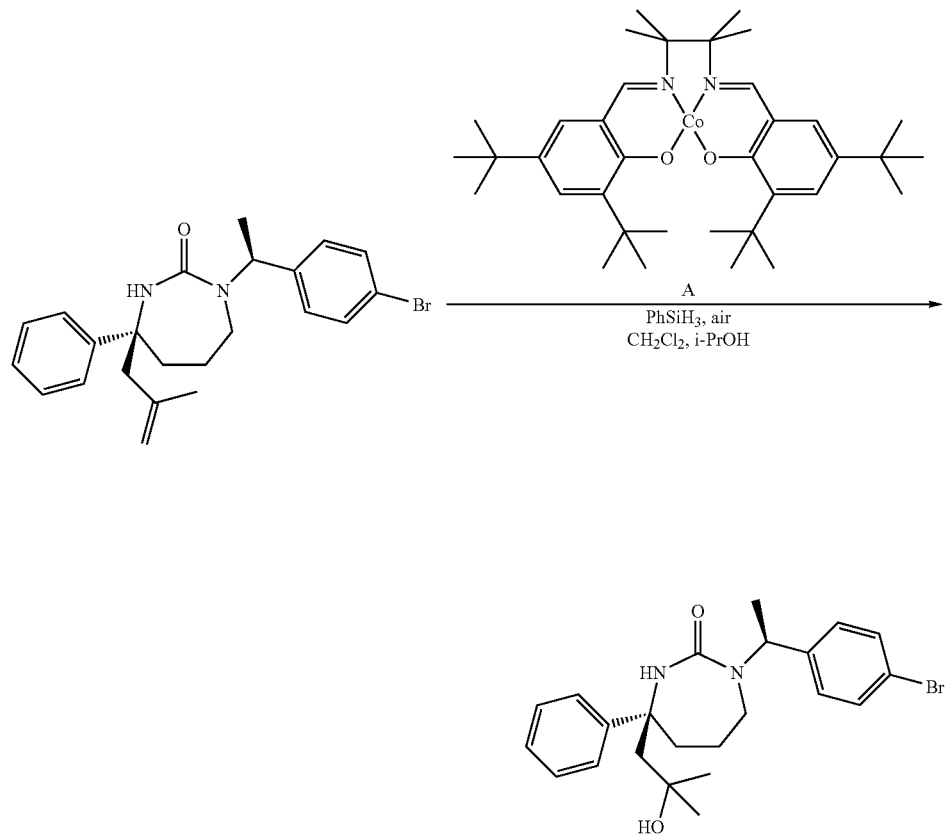

To a solution of (S)-1-((S)-1-(4-bromophenyl)ethyl)-4-(2-methylallyl)-4-phenyl-1,3-diazepan-2-one (23 mg, 0.054 mmol) in 2:1 i-Propanol/CH$_2$Cl$_2$ (2 mL) was added the cobalt catalyst A, prepared as described below, (c.a. 1 mg, cat. amount) and phenylsilane (250 µL, excess). The mixture was stirred vigorously in open air for 1 h. LC-MS found the reaction completed. The mixture was quenched with 1% aq HCl, concentrated and purified by prep HPLC to afford the title compound (9.1 mg, 38%). LC-MS Method 1 $t_R$=2.12 min., m/z 445, 447(M+1); $^1$H NMR (CDCl$_3$) δ 7.48 (d, 2H), 7.37-7.22 (m, 5H), 6.97 (d, 2H), 5.52 (q, 1H), 2.84 (td, 1H), 2.65 (dt, 1H), 2.28-2.07 (m, 3H), 1.89 (d, 1H), 1.45 (d, 3H), 1.21 (s, 3H), 1.07 (m, 1H), 0.62 (s, 3H).

A 50-mL flask was charged with N,N'-bis(3,5-di-tert-butylsalicylidene)-1,1,2,2-tetramethylethenediamine (0.430 g, 0.78 mmol, 1.0 equiv), EtOH (17 mL), and Co(OAc)$_2$ (0.139 g, 0.78 mmol, 1.0 equiv). The mixture was degassed and then heated to reflux under nitrogen for 3 h, cooled to rt. The precipitate was filtered and the purple solid was washed with EtOH (10 mL) and dried under high vacuum to give cobalt catalyst A. (0.353 g, 75%).

EXAMPLE 9

(S)-1-((S)-1-(4-(1-methyl-2-oxo-1,2-dihydropyridin-4-yl)phenyl)ethyl)-4-(2-methylallyl)-4-phenyl-1,3-diazepan-2-one

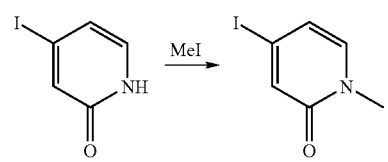

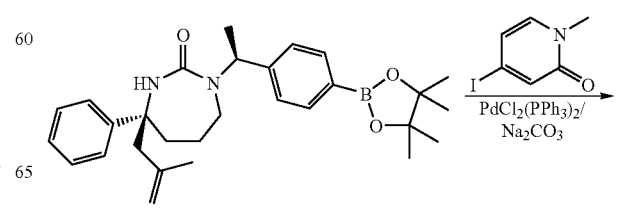

-continued

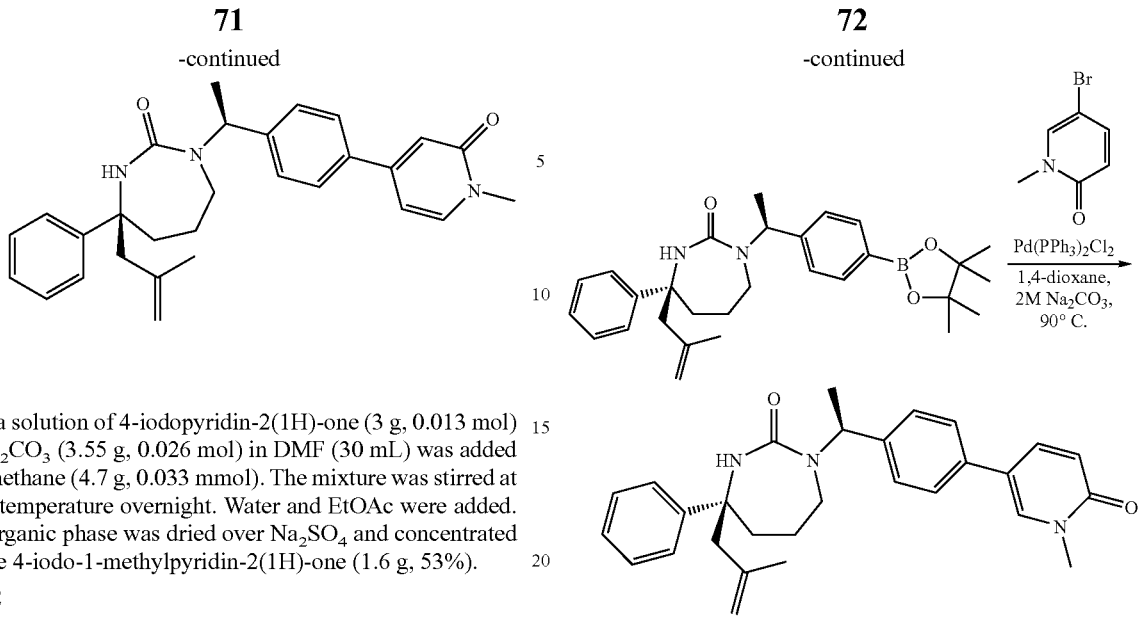

Step 1

To a solution of 4-iodopyridin-2(1H)-one (3 g, 0.013 mol) and K₂CO₃ (3.55 g, 0.026 mol) in DMF (30 mL) was added iodomethane (4.7 g, 0.033 mmol). The mixture was stirred at room temperature overnight. Water and EtOAc were added. The organic phase was dried over Na₂SO₄ and concentrated to give 4-iodo-1-methylpyridin-2(1H)-one (1.6 g, 53%).

Step 2

The title compound was prepared following a procedure analogous to that described in Example 10 Step 3 using (S)-4-(2-methylallyl)-4-phenyl-1-((S)-1-(4-(4,4,5,5-tetramethyl-1,3,2-dioxaborolan-2-yl)phenyl)ethyl)-1,3-diazepan-2-one and 4-iodo-1-methylpyridin-2(1H)-one.

EXAMPLE 10

(S)-1-((S)-1-(4-(1-methyl-6-oxo-1,6-dihydropyridin-3-yl)phenyl)ethyl)-4-(2-methylallyl)-4-phenyl-1,3-diazepan-2-one

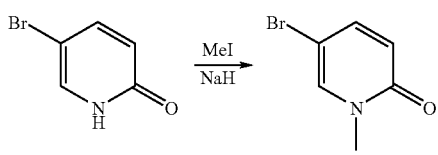

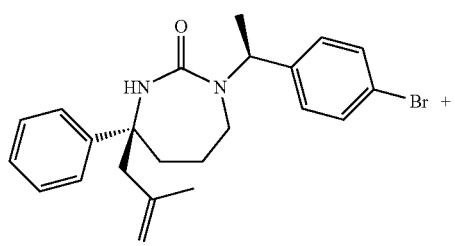

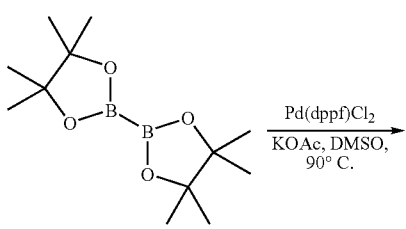

Step 1

To a suspension of NaH (4.8 g, 0.2 mol) in THF (10 mL) was added a solution of 5-bromopyridin-2(1H)-one (8.6 g, 0.05 mol) in THF (120 mL) at 0° C. The resulting mixture was stirred for 1 h and CH₃I (35.5 g, 0.25 mol) was added. The mixture was stirred for 3 h. The reaction was quenched with aqueous NH₄Cl solution. The organic phase was concentrated to give the crude product, which was purified by column chromatography to give 5-bromo-1-methylpyridin-2(1H)-one (8.9 g, 96.78%). ¹H NMR (CDCl₃): δ=3.5 (S, 3H), 6.52 (m, 1H), 7.32 (m, 1H), 7.45 (m, 1H).

Step 2

A mixture of (S)-1-((S)-1-(4-bromophenyl)ethyl)-4-(2-methylallyl)-4-phenyl-1,3-diazepan-2-one (450 mg, 1.01 mmol), bis(pinacolato)diboron (335 mg, 1.3 equiv.), potassium acetate (317 mg, 3.2 equiv.), and Pd(dppf)Cl₂CH₂Cl₂ (27 mg, 0.033 equiv.) were mixed with dry DMSO (8 mL). The mixture was vacuumed and refilled with Nitrogen gas (3×), before being heated to 90° C. overnight. After being cooled down, the mixture was diluted with EtOAc (50 mL) and washed with water (15 mL). The aqueous layer was extracted with EtOAc (10 mL). The combined organic layers were washed by water (10 mL), brine (10 mL), dried over Na₂SO₄. After filtration and concentration, the residue was purified by chromatography on a 12-g silica gel cartridge, eluted with a 5-30% EtOAc in hexanes gradient, to afford (S)-4-(2-methylallyl)-4-phenyl-1-((S)-1-(4-(4,4,5,5-tetramethyl-1,3,2-dioxaborolan-2-yl)phenyl)ethyl)-1,3-diazepan-2-one (416.7 mg, 83%). LC-MS Method 1 $t_R$=2.39 min., m/z 475(M+1).

Step 3

(S)-4-(2-methylallyl)-4-phenyl-1-((S)-1-(4-(4,4,5,5-tetramethyl-1,3,2-dioxaborolan-2-yl)phenyl)ethyl)-1,3-diazepan-2-one (38 mg, 0.08 mmol), 5-bromo-1-methylpyridin-2(1H)-one (23 mg, 1.5 equiv.), Pd(PPh₃)₂Cl₂ (2 mg, cat. amount), 2M aq Na₂CO₃ (500 μL, excess), and 1,4-Dioxane (4 mL) were mixed. The mixture was evacuated and refilled with nitrogen gas (3×), before being heated to 90° C. overnight. After being cooled down, the mixture was concentrated, acidified with 5% aq HCl and purified by prep HPLC to afford (S)-1-((S)-1-(4-(1-methyl-6-oxo-1,6-dihydropyridin-3-yl)phenyl)ethyl)-4-(2-methylallyl)-4-phenyl-1,3-diazepan-2-one (16 mg, 44%). LC-MS Method 1 $t_R$=1.76 min., m/z 456 (M+1); ¹H NMR (CD₃OD) δ 7.90 (s, 1H), 7.80 (dd, 1H), 7.47 (d, 2H), 7.39 (t, 2H), 7.30 (d, 3H), 6.96 (d, 2H), 6.61 (d, 1H), 5.32 (q, 1H), 5.02 (d, 1H), 3.61 (s, 3H), 2.59-2.45 (m, 2H), 1.49 (d, 3H), 1.15 (s, 3H).

EXAMPLE 11

(S)-4-(2-hydroxy-2-methylpropyl)-1-((S)-1-(4-(1-methyl-2-oxo-1,2-dihydropyridin-4-yl)phenyl)ethyl)-4-phenyl-1,3-diazepan-2-one

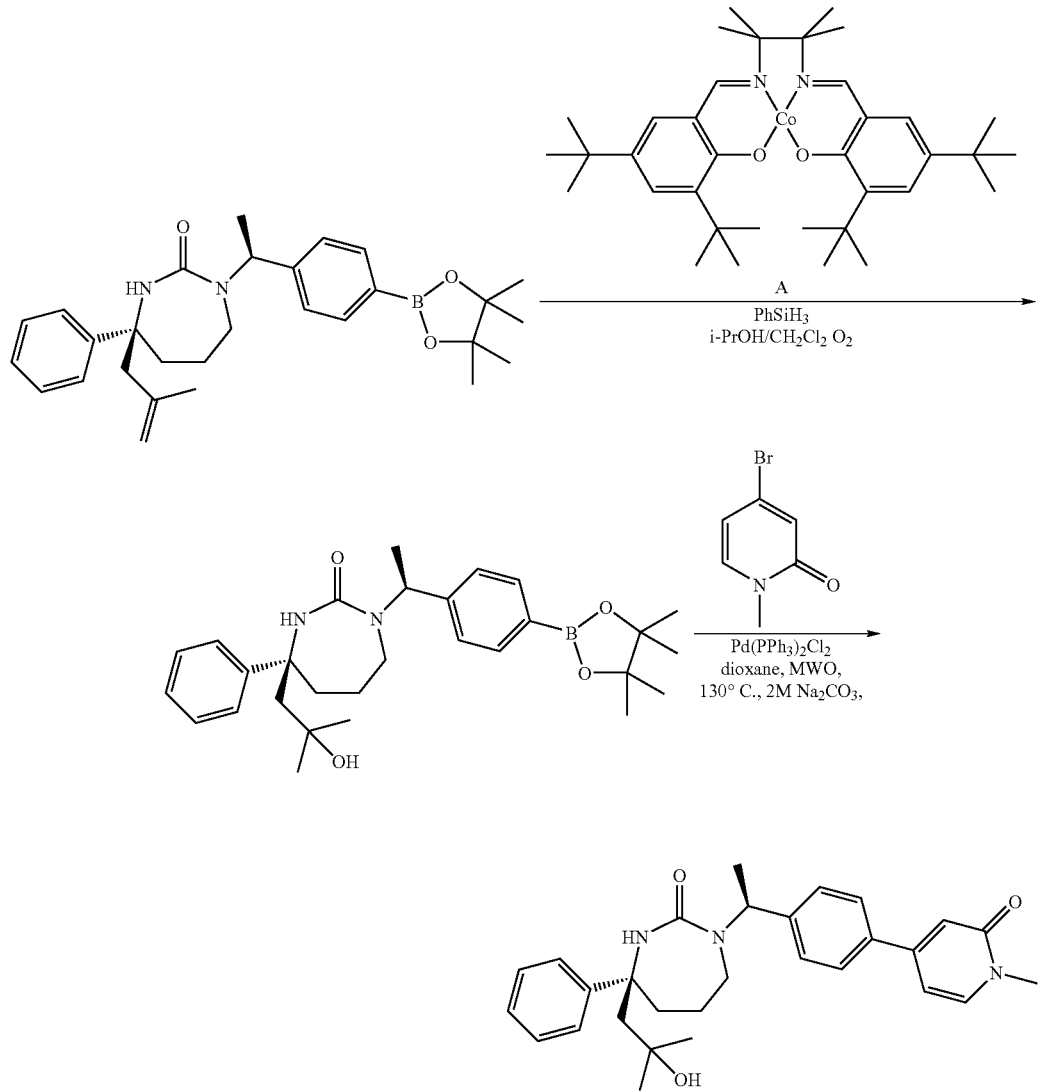

Step 1

To a solution of (S)-4-(2-methylallyl)-4-phenyl-1-((S)-1-(4-(4,4,5,5-tetramethyl-1,3,2-dioxaborolan-2-yl)phenyl) ethyl)-1,3-diazepan-2-one (260 mg, 0.55 mmol) in 2:1 i-propanol/CH₂Cl₂ (10 mL) was added cobalt catalyst A (7 mg, 2% mol) and phenylsilane (1 mL, excess). The mixture was stirred vigorously in open air for 1 h. LC-MS found the reaction completed. The mixture was quenched with 1% aq HCl, concentrated and purified by chromatography on a 12 g-silica gel cartridge, eluted with a 50~100% EtOAc in hexanes gradient, to afford (S)-4-(2-hydroxy-2-methylpropyl)-4-phenyl-1-((S)-1-(4-(4,4,5,5-tetramethyl-1,3,2-dioxaborolan-2-yl)phenyl)ethyl)-1,3-diazepan-2-one (163 mg, 60%). LC-MS Method 1 $t_R$=2.13 min., m/z 492(M+1).

Step 2

(S)-4-(2-hydroxy-2-methylpropyl)-4-phenyl-1-((S)-1-(4-(4,4,5,5-tetramethyl-1,3,2-dioxaborolan-2-yl)phenyl)ethyl)-1,3-diazepan-2-one (10 mg, 0.02 mmol), 4-bromo-1-methylpyridin-2(1H)-one (7.6 mg, 2 equiv.), Pd(PPh₃)₂Cl₂ (1 mg, cat. amount), 2M aq Na₂CO₃ solution (200 μL, excess), and 1,4-dioxane (2 mL) were mixed. The mixture was evacuated and refilled with Nitrogen gas 3×, before being heated to 130° C. in the microwave oven for 2 h. After being cooled down, the mixture was concentrated, acidified with 5% aq HCl and purified by prep HPLC to afford (S)-4-(2-hydroxy-2-methylpropyl)-1-((S)-1-(4-(1-methyl-2-oxo-1,2-dihydropyridin-4-yl)phenyl)ethyl)-4-phenyl-1,3-diazepan-2-one (3.7 mg, 38%). LC-MS Method 1 $t_R$=1.53 min., m/z 474 (M+1); H¹ NMR (CD₃OD) δ 7.63 (d, 1H), 7.51 (d, 2H), 7.43 (d, 2H), 7.32 (t, 2H), 7.22 (t, 1H), 7.14 (d, 2H), 6.74-6.59 (m, 2H), 5.42 (q, 1H), 3.55 (s, 3H), 2.89 (m, 1H), 2.71 (m, 1H), 2.34 (d, 1H), 1.49 (d, 3H), 1.12 (s, 3H), 0.54 (s, 3H).

EXAMPLE 12

(S)-4-(2-hydroxy-2-methylpropyl)-1-((S)-1-(4-(1-methyl-6-oxo-1,6-dihydropyridin-3-yl)phenyl)ethyl)-4-phenyl-1,3-diazepan-2-one

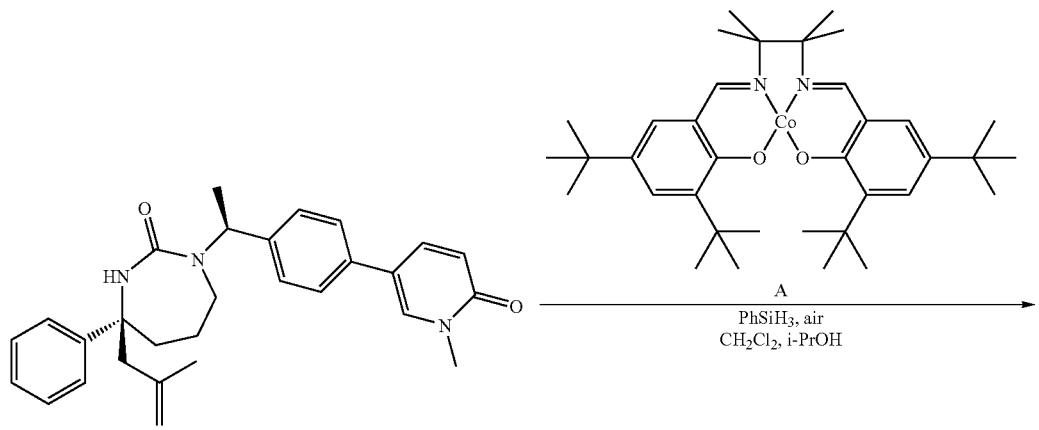

To a solution of (S)-1-((S)-1-(4-(1-methyl-6-oxo-1,6-dihydropyridin-3-yl)phenyl)ethyl)-4-(2-methylallyl)-4-phenyl-1,3-diazepan-2-one (4 mg, 0.0088 mmol) in 2:1 i-Propanol/CH$_2$Cl$_2$ (2 mL) was added the cobalt catalyst A (c.a. 1 mg, cat. amount) and phenylsilane (100 µL, excess). The mixture was stirred vigorously in open air for 1 h. LC-MS found the reaction completed. The mixture was quenched by 1% aq HCl, concentrated and purified by prep HPLC to afford (S)-4-(2-hydroxy-2-methylpropyl)-1-((S)-1-(4-(1-methyl-6-oxo-1,6-dihydropyridin-3-yl)phenyl)ethyl)-4-phenyl-1,3-diazepan-2-one (1.4 mg, 34%). LC-MS Method 1 t$_R$=1.56 min., m/z 473 (M+1); $^1$H NMR (CD$_3$OD) δ 7.93 (s, 1H), 7.83 (dd, 1H), 7.56 (d, 2H), 7.40-7.34 (m, 4H), 7.27 (t, 1H), 7.16 (d, 2H), 6.62 (d, 1H), 5.46 (q, 1H), 3.63 (s, 3H), 2.93 (m, 1H), 2.76 (m, 1H), 2.39 (d, 1H), 1.52 (d, 3H), 1.17 (s, 3H), 0.59 (s, 3H).

EXAMPLE 13

(S)-1-((S)-1-(4-(1-cyclopropyl-2-oxo-1,2-dihydropyridin-4-yl)phenyl)ethyl)-4-(2-hydroxy-2-methylpropyl)-4-phenyl-1,3-diazepan-2-one

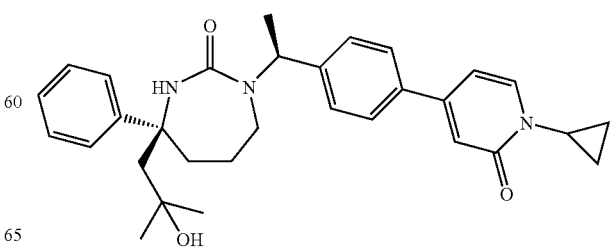

The title compound was prepared from (S)-4-(2-hydroxy-2-methylpropyl)-4-phenyl-1-((S)-1-(4-(4,4,5,5-tetramethyl-1,3,2-dioxaborolan-2-yl)phenyl)ethyl)-1,3-diazepan-2-one and 1-cyclopropyl-4-iodopyridin-2(1H)-one following a procedure analogous to that described in Example 11 Step 2. 1-cyclopropyl-4-iodopyridin-2(1H)-one was prepared as described below.

A mixture of 4-iodopyridin-2(1H)-one (0.2425 g, 1.10 mmol, 1.0 equiv), Cu(OAc)$_2$ (0.2146 g, 1.18 mmol, 1.07 equiv), bipyridine (0.1832 g, 1.17 mmol, 1.07 equiv), cyclopropylboronic acid (0.2122 g, 2.47 mmol, 2.25 equiv) and Na$_2$CO$_3$ (0.2638 g, 2.49 mmol, 2.27 equiv) in dichloroethane (10 mL) was stirred at 70° C. for 18 h. The reaction mixture was quenched with satd aq NH$_4$Cl, diluted with CH$_2$Cl$_2$, and dried over Na$_2$SO$_4$. After the solvent was removed under reduced pressure, the residue was purified by chromatography on silica gel eluted with hexanes/ethyl acetate to afford 0.2309 g (81%) of 1-cyclopropyl-4-iodopyridin-2(1H)-one.

EXAMPLE 14

3-((1S)-1-(4-bromophenyl)ethyl)-7-(2-methylallyl)-7-phenyl-1,3-oxazepan-2-one

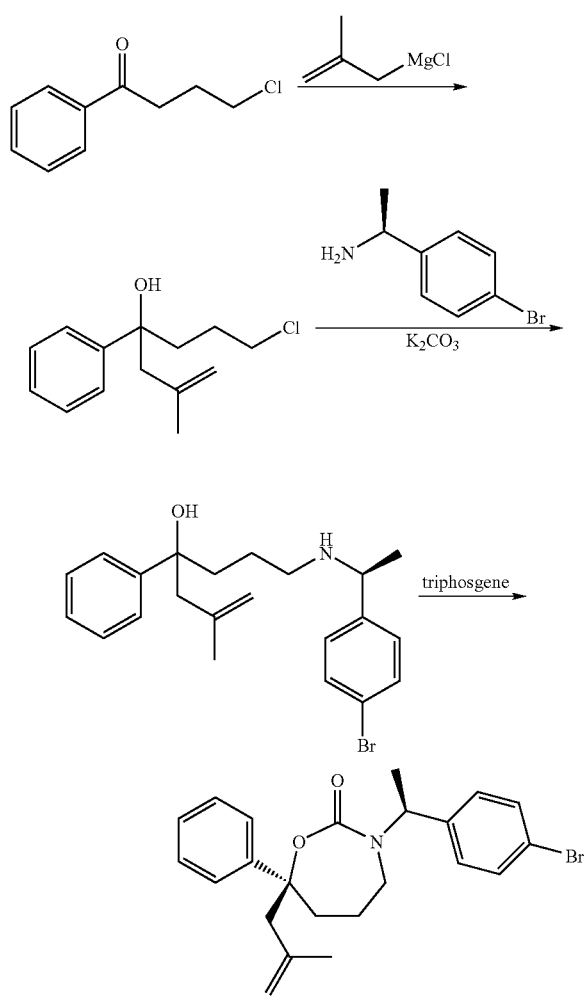

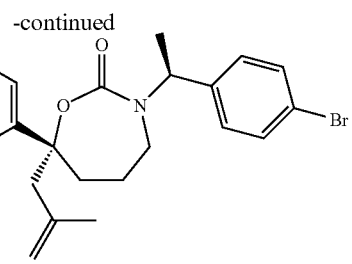

Step 1

To a solution of compound 4-chloro-1-phenylbutan-1-one (3.64 g, 0.02 mol) in THF (60 mL) was added (2-methylallyl)magnesium chloride (60 mL, 1 mol/L) at −78° C. The mixture was stirred at room temperature for 1 h. TLC showed the disappearance of the starting material. The mixture was quenched with satd aq NH$_4$Cl and extracted with EtOAc. The combined organic phase was dried over Na$_2$SO$_4$ and concentrated to give the crude final product, which was purified by chromatography to afford the compound 7-chloro-2-methyl-4-phenylhept-1-en-4-ol (4.2 g, 90%).

Step 2

To a solution of (S)-1-(4-bromo-phenyl)-ethyl amine (3.58 g, 0.018 mol) in dry CH$_3$CN (350 mL) was added 3-((1S)-1-(4-bromophenyl)ethyl)-7-(2-methylallyl)-7-phenyl-1,3-oxazepan-2-one (4.2 g, 0.018 mol), KI (3.19 g, 0.019 mol), and K$_2$CO$_3$ (3.73 g, 0.027 mol). The mixture was stirred at reflux overnight, filtered, and concentrated to give the crude product, which was purified by column chromatography to give 7-((1S)-1-(4-bromophenyl)ethylamino)-2-methyl-4-phenyl-hept-1-en-4-ol (2.2 g, 30%) as an oil.

Step 3

To a solution of compound 7-((1S)-1-(4-bromophenyl)ethylamino)-2-methyl-4-phenylhept-1-en-4-ol (2.2 g, 5.5 mmol) in CH$_2$Cl$_2$ (50 mL) was added triphosgene (3.2 g, 11 mmol) and Et$_3$N (1.7 g, 16.5 mmol) at 0° C. The mixture was stirred at room temperature overnight, and put at room temperature for 3 days, the volatile was evaporated. The resulting mixture was washed with 1 N aq HCl and extracted with CH$_2$Cl$_2$. The combined organic phase was dried over Na$_2$SO$_4$ and concentrated to give the crude final product, which was purified by chromatography to afford two isomers.

Isomer 1: (S)-3-((S)-1-(4-bromophenyl)ethyl)-7-(2-methylallyl)-7-phenyl-1,3-oxazepan-2-one (400 mg, 17%). LC-MS Method 1 t$_R$=2.34 min, m/z=450, 452 (M+Na); $^1$H NMR (CDCl$_3$) δ 7.48 (d, 2H), 7.40 (t, 2H), 7.33 (m, 1H), 7.27 (d, 2H), 6.62 (d, 2H), 5.23 (q, 1H), 4.80 (s, 1H), 4.59 (s, 1H), 2.98-2.83 (m, 2H), 2.67 (s, 3H), 2.44 (dt, 1H), 2.08 (m, 1H), 1.51 (s, 3H), 1.46 (d, 3H), 1.30 (m, 1H).

Isomer 2: (R)-3-((S)-1-(4-bromophenyl)ethyl)-7-(2-methylallyl)-7-phenyl-1,3-oxazepan-2-one. (300 mg, 13%). LC-MS Method 1 t$_R$=2.33 min, m/z=450, 452 (M+1). $^1$H NMR (CDCl$_3$) δ 7.46 (d, 4H), 7.33 (t, 2H), 7.26 (m, 3H), 5.46 (q, 1H), 4.77 (s, 1H), 4.56 (s, 1H), 3.05 (m, 1H), 2.87 (dt, 1H), 2.67 (q, 2H), 2.31 (dt, 1H), 2.05 (m, 1H), 1.47 (s, 3H), 1.39 (m, 1H), 1.31 (d, 3H), 1.19 (m, 1H).

Alternate Method for Step 3

A solution of 7-((1S)-1-(4-bromophenyl)ethylamino)-2-methyl-4-phenylhept-1-en-4-ol (111.7 mg, 0.279 mmol) in anhydrous acetonitrile (7 mL) was cooled to 0° C. Triethylamine (78 μL, 2 equiv) and 20% phosgene in toluene solution (161 μL, 1.1 equiv) were added sequentially and slowly. After stirring 2 h at 0° C., NaH (60% in mineral oil, 22 mg, 2 equiv) was added. The mixture was stirred overnight and the ice bath was allowed to melt. LC-MS showed the reaction was complete. The mixture was cooled to 0° C. again, quenched by addition of satd aq NH₄Cl (2 mL), concentrated to remove the organic solvents, diluted with ether (10 mL), washed with 1% HCl (3 mL), satd aq NaHCO₃ (2 mL) and brine (2 mL), and dried over Na₂SO₄. After filtration and concentration, the residue was purified by chromatography on a 12-g silica cartridge, eluted with a 15~40% EtOAc in hexanes gradient, to afford 3-((1S)-1-(4-bromophenyl)ethyl)-7-(2-methylallyl)-7-phenyl-1,3-oxazepan-2-one (49.6 mg, 42%) as a mixture of two diastereomers.

EXAMPLE 15

3-((1S)-1-(4-bromophenyl)ethyl)-7-(2-hydroxy-2-methylpropyl)-7-phenyl-1,3-oxazepan-2-one Isomer 1

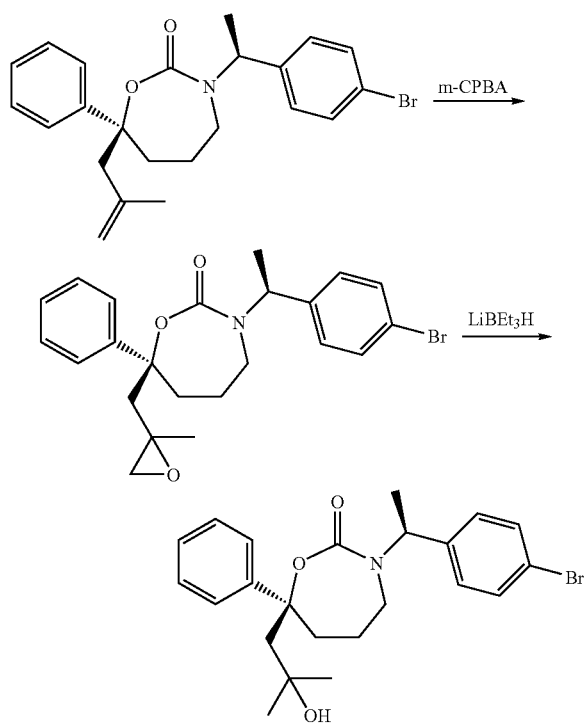

Step 1

To a solution of (S)-3-((S)-1-(4-bromophenyl)ethyl)-7-(2-methylallyl)-7-phenyl-1,3-oxazepan-2-one (300 mg, 0.7 mmol) in dry CH₂Cl₂ (20 mL) was added m-CPBA (605 mg, 3.5 mmol) at room temperature. The reaction mixture was stirred until the starting material was completed. The mixture was diluted with (CH₃)₃COCH₃ (30 mL), washed by 30% Na₂S₂O₃, and NaHCO₃ (aq.) for three times, dried over Na₂SO₄, filtered, and concentrated to give (7S)-3-((S)-1-(4-bromophenyl)ethyl)-7-((2-methyloxiran-2-yl)methyl)-7-phenyl-1,3-oxazepan-2-one (280 mg, 90%), which was used directly for the next step without further purification.

Step 2

To a solution of (7S)-3-((S)-1-(4-bromophenyl)ethyl)-7-((2-methyloxiran-2-yl)methyl)-7-phenyl-1,3-oxazepan-2-one (280 mg, 0.63 mmol) in THF (10 mL) was added dropwise 1 M LiEt₃BH in THF (Super-hydride, 6.3 mL, 6.3 mmol) at 0° C. under N₂ for 30 min. The resulting solution was stirred at room temperature for 1 h, quenched with H₂O₂ (7 mL), diluted with (CH₃)₃COCH₃ (30 mL), washed with water, 30% aq Na₂S₂O₃ and brine. The organic phase was dried over Na₂SO₄, and concentrated to give the crude product, which was purified by prep TLC afford (S)-3-((S)-1-(4-bromophenyl)ethyl)-7-(2-hydroxy-2-methylpropyl)-7-phenyl-1,3-oxazepan-2-one (150 mg, 53%). (S)-3-((S)-1-(4-bromophenyl)ethyl)-7-(2-hydroxy-2-methylpropyl)-7-phenyl-1,3-oxazepan-2-one. LC-MS Method 30-90 $t_R$=1.199 min, m/z=470; ¹H NMR (CDCl₃) d 0.83 (s, 3H), 1.05 (m, 1H), 1.13 (s, 3H), 1.42 (m, 1H), 1.48 (d, 3H), 2.1-2.35 (m, 4H), 2.72 (m, 1H), 3.13 (m, 1H), 3.95 (s, 1H), 5.50 (m, 1H), 7.02 (d, 2H), 7.22 (m, 1H), 7.30 (m, 2H), 7.32-7.48 (m, 4H).

Isomer 2

(R)-3-((S)-1-(4-bromophenyl)ethyl)-7-(2-hydroxy-2-methylpropyl)-7-phenyl-1,3-oxazepan-2-one was prepared following procedures analogous to those described immediately above starting with (R)-3-((S)-1-(4-bromophenyl)ethyl)-7-(2-methylallyl)-7-phenyl-1,3-oxazepan-2-one. LC-MS Method 30-90 $t_R$=1.192 min, m/z=467.9; ¹H NMR (CDCl₃) d 0.65 (m, 1H), 0.82 (m, 4H), 1.10 (s, 3H), 1.43 (d, 3H), 1.90 (m, 2H), 2.13 (d, 1H), 2.32 (d, 1H), 2.69 (m, 1H), 3.25 (m, 1H), 4.14 (s, 1H), 5.52 (m, 1H), 7.18 (m, 3H), 7.28 (m, 2H), 7.40 (m, 4H)

EXAMPLE 16

3-((S)-1-(4-(2-methoxypyridin-4-yl)phenyl)ethyl)-7-(2-methylallyl)-7-phenyl-1,3-oxazepan-2-one

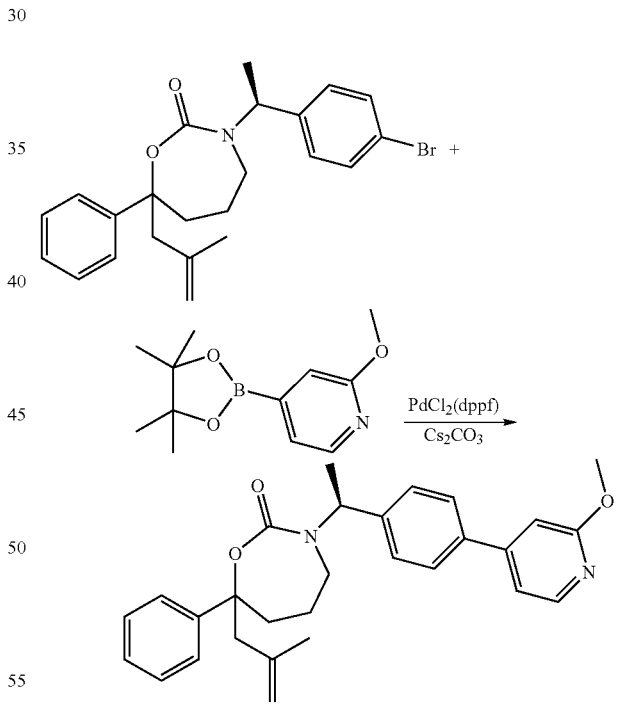

Isomer 1

(S)-3-((S)-1-(4-(2-methoxypyridin-4-yl)phenyl)ethyl)-7-(2-methylallyl)-7-phenyl-1,3-oxazepan-2-one was prepared from (S)-3-((S)-1-(4-bromophenyl)ethyl)-7-(2-methylallyl)-7-phenyl-1,3-oxazepan-2-one and 2-methoxy-4-(4,4,5,5-tetramethyl-1,3,2-dioxaborolan-2-yl)pyridine following conditions analogous to those described in Example 6 using PdCl₂ (dppf) as catalyst. $t_R$=2.25 min, m/z 457 (M+1). ¹H NMR (CD₃OD) δ 8.08 (t, 1H), 7.50-7.27 (m, 7H), 7.11 (t, 1H), 6.92 (d, 1H), 6.86 (t, 2H), 5.13 (m, 1H), 4.71 (s, 1H), 4.53 (s, 1H), 3.88 (d, 3H), 2.95 (m, 2H), 2.58 (m, 2H), 2.47 (m, 1H), 2.04 (m, 1H), 1.51-1.40 (m, 6H), 1.26 (m, 2H).

Isomer 2

(R)-3-((S)-1-(4-(2-methoxypyridin-4-yl)phenyl)ethyl)-7-(2-methylallyl)-7-phenyl-1,3-oxazepan-2-one was prepared from (R)-3-((S)-1-(4-bromophenyl)ethyl)-7-(2-methylallyl)-7-phenyl-1,3-oxazepan-2-one and 2-methoxy-4-(4,4,5,5-tetramethyl-1,3,2-dioxaborolan-2-yl)pyridine following conditions analogous to those described in Example 6 using PdCl$_2$(dppf) as catalyst. $t_R$=2.28 min, m/z 457 (M+1). $^1$H NMR (CD$_3$OD) δ 8.13 (m, 2H), 7.83 (d, 1H), 7.71 (d, 2H), 7.49 (t, 3H), 7.33 (t, 2H), 7.24 (m, 2H), 7.06 (d, 1H), 5.41 (q, 1H), 4.56 (s, 1H), 3.85 (d, 3H), 3.17-2.99 (m, 2H), 2.39 (dt, 1H), 2.09 (m, 1H), 1.45 (s, 3H), 1.38 (d, 3H).

EXAMPLE 17

7-(2-hydroxy-2-methylpropyl)-3-((1S)-1-(4-hydroxyphenyl)ethyl)-7-phenyl-1,3-oxazepan-2-one

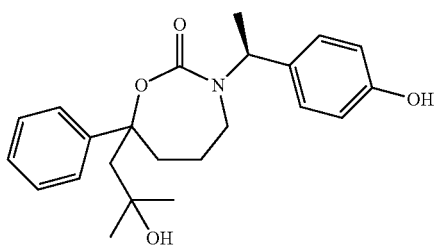

Two isomers of the title compound were isolated as byproducts from Example 18 Step 2.

Isomer 1: LC-MS Method 3 $t_R$=0.898 min, m/z=789.5; $^1$H NMR (CDCl$_3$) d 0.80 (s, 3H), 1.00 (m, 1H), 1.13 (s, 3H), 1.45 (m, 4H), 2.10 (m, 2H), 2.20 (d, 1H), 2.36 (d, 1H), 2.79 (m, 1H), 3.18 (m, 1H), 5.00 (s, 1H), 5.50 (m, 1H), 6.70 (d, 2H), 7.09 (d, 2H), 7.20 (m, 1H), 7.28 (t, 2H), 7.40 (d, 2H)

Isomer 2: LC-MS Method 3 $t_R$=0.933 min, m/z=789.5; $^1$H NMR (CDCl$_3$) d 0.62 (m, 1H), 0.78 (m, 1H), 0.82 (s, 3H), 1.10 (s, 3H), 1.43 (d, 3H), 1.85 (m, 2H), 2.13 (d, 1H), 2.32 (d, 1H), 2.72 (m, 1H), 3.25 (m, 1H), 5.55 (m, 1H), 6.40 (s, 1H), 6.80 (d, 2H), 7.20 (m, 3H), 7.30 (m, 2H), 7.40 (m, 4H)

EXAMPLE 18

(S)-3-((S)-1-(4-(1-cyclopropyl-2-oxo-1,2-dihydropyridin-4-yl)phenyl)ethyl)-7-(2-hydroxy-2-methylpropyl)-7-phenyl-1,3-oxazepan-2-one

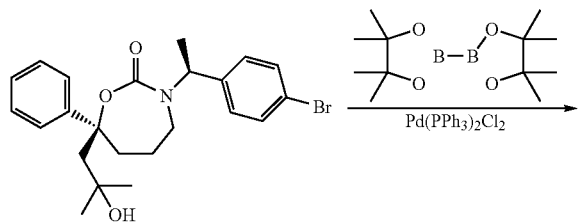

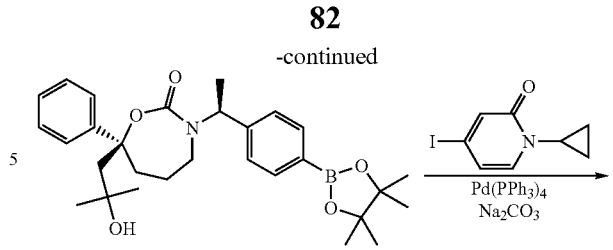

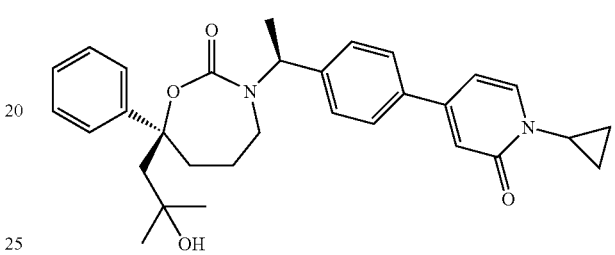

Step 1

To a solution of (S)-3-((S)-1-(4-bromophenyl)ethyl)-7-(2-hydroxy-2-methylpropyl)-7-phenyl-1,3-oxazepan-2-one (150 mg, 0.34 mmol) in DMSO (5 mL) was added 4,4,5,5-tetramethyl-1,3,2-dioxaborolan-2-yl)-1,3,2-dioxaborolane (254 mg, 1.02 mmol), KOAc (466 mg, 4.76 mmol), and Pd(dppf)$_2$Cl$_2$ (10 mg) under N$_2$. The formed mixture was stirred at 100° C. for 2 h, quenched with H$_2$O, and extracted with EtOAc. The organic phase was dried over Na$_2$SO$_4$ and concentrated to give the crude product, which was purified by preparative TLC to give the (S)-7-(2-hydroxy-2-methylpropyl)-7-phenyl-3-((S)-1-(4-(4,4,5,5-tetramethyl-1,3,2-dioxaborolan-2-yl)phenyl)ethyl)-1,3-oxazepan-2-one (84 mg, 50%).

Step 2

A mixture of (S)-7-(2-hydroxy-2-methylpropyl)-7-phenyl-3-((S)-1-(4-(4,4,5,5-tetramethyl-1,3,2-dioxaborolan-2-yl)phenyl)ethyl)-1,3-oxazepan-2-one (20 mg, 0.04 mmol), 1-cyclopropyl-4-iodopyridin-2(1H)-one (10 mg, 0.04 mmol), Pd(PPh$_3$)$_4$ (5 mg), and Na$_2$CO$_3$ (43 mg, 0.36 mmol) in toluene/EtOH/H$_2$O (3 mL/2 mL/2 mL) was stirred under N$_2$ at 100° C. for 2 h. The reaction mixture was diluted with water (5 mL), and extracted with EtOAc. The combined organic layers were washed with brine, dried over Na$_2$SO$_4$, and concentrated to give the crude product, which was purified by preparative-HPLC to give (S)-3-((S)-1-(4-(1-cyclopropyl-2-oxo-1,2-dihydropyridin-4-yl)phenyl)ethyl)-7-(2-hydroxy-2-methylpropyl)-7-phenyl-1,3-oxazepan-2-one (8 mg, yield 40%) LC-MS Method 4 $t_R$=1.166 min, m/z=443.1; $^1$H NMR (CDCl$_3$) d 0.85 (m, 5H), 1.10 (m, 6H), 1.43 (m, 1H), 1.52 (d, 3H), 2.18 (m, 2H), 2.20 (d, 1H), 2.36 (d, 1H), 2.79 (m, 1H), 3.12-3.35 (m, 2H), 4.00 (s, 1H), 5.59 (m, 1H), 6.30 (d, 1H), 6.70 (d, 1H), 7.18-7.32 (m, 6H), 7.45 (m, 4H)

EXAMPLE 19

(S)-7-(2-hydroxy-2-methylpropyl)-3-((S)-1-(4-(1-methyl-2-oxo-1,2-dihydropyridin-4-yl)phenyl)ethyl)-7-phenyl-1,3-oxazepan-2-one

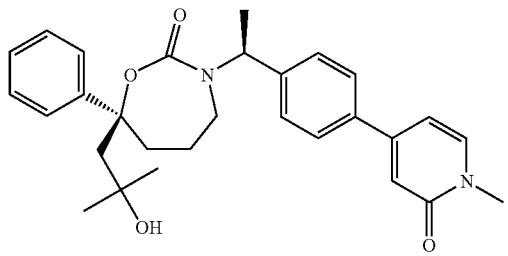

The title compound was prepared from (S)-7-(2-hydroxy-2-methylpropyl)-7-phenyl-3-((S)-1-(4-(4,4,5,5-tetramethyl-1,3,2-dioxaborolan-2-yl)phenyl)ethyl)-1,3-oxazepan-2-one and 4-iodo-1-methylpyridin-2(1H)-one following a procedure analogous to that described in Example 18 Step 2. LC-MS Method 4 $t_R$=1.11 min; m/z=497, 475, 457, 417.

Isomer 2

EXAMPLE 20

(S)-1-((S)-1-(4-(1-cyclopropyl-6-oxo-1,6-dihydropyridin-3-yl)phenyl)ethyl)-4-(2-hydroxy-2-methylpropyl)-4-phenyl-1,3-diazepan-2-one

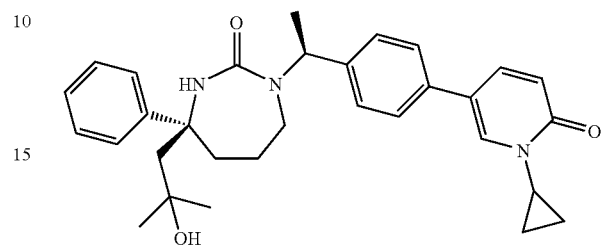

The title compound was prepared from (S)-4-(2-hydroxy-2-methylpropyl)-4-phenyl-1-((S)-1-(4-(4,4,5,5-tetramethyl-1,3,2-dioxaborolan-2-yl)phenyl)ethyl)-1,3-diazepan-2-one and 5-bromo-1-cyclopropylpyridin-2(1H)-one following a procedure analogous to that described in Example 11 Step 2. LC-MS Method 1 $t_R$=1.66 min; m/z=500 (M+1). $^1$H NMR (CD$_3$OD) δ 7.78 (s, 1H), 7.56 (d, 3H), 7.37 (m, 5H), 7.27 (t, 1H), 7.17 (d, 2H), 6.61 (d, 1H), 5.46 (q, 1H), 3.37 (m, 1H), 2.92 (m, 1H), 2.74 (dt, 1H), 2.39 (d, 1H), 1.53 (d, 3H), 1.16 (s, 3H), 0.58 (s, 3H).

Prophetic Compound Tables

TABLE 1

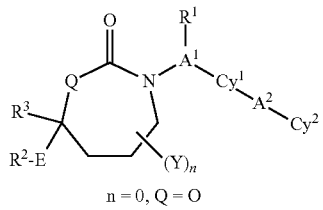

n = 0, Q = O

| Prophetic Example No. | $A^1$-$R^1$ | $Cy^1$ | $A^2$ | $Cy^2$ | E | $R^2$ | $R^3$ |
|---|---|---|---|---|---|---|---|
| 1a | bond | 3-Me-Ph | bond | H | bond | Ph | Me |
| 2a | bond | 3-Br-Ph | bond | H | bond | Ph | Me |
| 3a | bond | 1,3-C$_6$H$_4$ | bond | Ph | bond | Ph | Me |
| 4a | bond | 1,3-C$_6$H$_4$ | bond | 2-Cl-Ph | bond | Ph | Me |
| 5a | bond | 1,3-C$_6$H$_4$ | bond | 2-NC-Ph | bond | Ph | Me |
| 6a | CH | 1,3-C$_6$H$_4$ | bond | 2-MeO-Ph | bond | Ph | Me |
| 7a | bond | 1,3-C$_6$H$_4$ | bond | 2,6-diCl-Ph | bond | Ph | Me |
| 8a | bond | 1,3-C$_6$H$_4$ | bond | 2,4-diF-Ph | bond | Ph | Me |
| 9a | bond | 1,3-C$_6$H$_4$ | bond | 3-Cl-Ph | bond | Ph | Me |
| 10a | bond | 1,3-C$_6$H$_4$ | bond | 3-F-Ph | bond | Ph | Me |
| 11a | bond | 1,3-C$_6$H$_4$ | bond | 2,5-diF-Ph | bond | Ph | Me |
| 12a | bond | 1,3-C$_6$H$_4$ | bond | 3,5-diF-Ph | bond | Ph | Me |
| 13a | bond | 1,3-C$_6$H$_4$ | bond | 4-F-Ph | bond | Ph | Me |
| 14a | bond | 1,3-C$_6$H$_4$ | bond | 2-F-Ph | bond | Ph | Me |
| 15a | bond | 2,6-pyridyl | bond | 2-Cl-4-F-Ph | bond | 2-F-Ph | HOCH$_2$CH$_2$ |
| 16a | CHMe | 1,4-C$_6$H$_4$ | bond | 2,4-diF-Ph | bond | 4-F-Ph | H$_2$NC(=O)CH$_2$ |
| 17a | CHMe | 1,4-C$_6$H$_4$ | bond | 2,4-diF-Ph | bond | 4-F-Ph | HOCH$_2$CH(OH)CH$_2$ |
| 18a | bond | 1,3-C$_6$H$_4$ | bond | 2,4-diF-Ph | bond | Ph | allyl |
| 19a | bond | 1,3-C$_6$H$_4$ | bond | 2,4-diF-Ph | bond | Ph | HOCH$_2$CH$_2$ |
| 20a | bond | 1,3-(4-F)C$_6$H$_3$ | bond | 4-F-Ph | bond | 4-F-Ph | HOCH$_2$CH$_2$ |
| 21a | bond | 1,3-(4-F)C$_6$H$_3$ | bond | 4-F-Ph | bond | 2-F-Ph | HOCH$_2$CH$_2$ |
| 22a | bond | 1,3-C$_6$H$_4$ | bond | 2-Cl-4-F-Ph | bond | Ph | HOCH$_2$CH$_2$ |
| 23a | bond | 1,3-C$_6$H$_4$ | bond | 2,6-diCl-Ph | bond | Ph | HOCH$_2$CH$_2$ |
| 24a | bond | 1,3-C$_6$H$_4$ | bond | 2,4-diF-Ph | bond | Ph | H$_2$NC(=O)CH$_2$ |
| 25a | CH | 1,3-C$_6$H$_4$ | bond | 2,4-diF-Ph | bond | Ph | HOCH$_2$CH(OH)CH$_2$ |
| 26a | bond | 1,3-C$_6$H$_4$ | bond | 2,4-diF-Ph | bond | Ph | HOCH$_2$CH$_2$CH$_2$ |

TABLE 1-continued

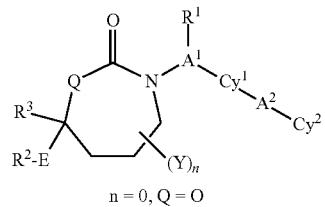

n = 0, Q = O

| Prophetic Example No. | A¹-R¹ | Cy¹ | A² | Cy² | E | R² | R³ |
|---|---|---|---|---|---|---|---|
| 27a | bond | 1,3-C₆H₄ | bond | Ph | bond | 3-Cl-Ph | Me |
| 28a | bond | 1,3-C₆H₄ | bond | 2,4-diF-Ph | bond | 2-pyridyl | Me |
| 29a | CHMe | Ph | bond | H | bond | Ph | Me |
| 30a | CHMe | 3-MeO-Ph | bond | H | bond | Ph | Me |
| 31a | CHMe | 4-MeO-Ph | bond | H | bond | Ph | Me |
| 32a | CHMe | Ph | bond | H | bond | 2-Me-Ph | Me |
| 33a | CHMe | Ph | bond | H | bond | 4-Me-Ph | Me |
| 34a | CHMe | Ph | bond | H | bond | 4-MeS-Ph | Me |
| 35a | CHMe | Ph | bond | H | bond | 4-F-Ph | allyl |
| 36a | bond | 1,3-C₆H₄ | bond | 4-F-Ph | bond | Ph | HOCH₂CH₂ |
| 37a | CHMe | Ph | bond | H | bond | 4-F-Ph | HOCH₂CH₂ |
| 38a | bond | 1,3-C₆H₄ | bond | Ph | bond | Ph | MeSO₂NHCH₂CH₂ |
| 39a | bond | 1,3-(4-F)C₆H₃ | bond | 2-Cl-4-F-Ph | bond | 4-F-Ph | HOCH₂CH₂ |
| 40a | bond | 1,3-C₆H₄ | bond | 2-Cl-4-F-Ph | bond | Ph | HOCH₂CH₂ |
| 41a | bond | 2,6-pyridyl | bond | 4-F-Ph | bond | Ph | HOCH₂CH₂ |
| 42a | bond | 2,6-pyridyl | bond | 4-F-Ph | bond | 4-F-Ph | HOCH₂CH₂ |
| 43a | bond | 2,6-pyridyl | bond | 4-F-Ph | bond | 2-F-Ph | HOCH₂CH₂ |
| 44a | bond | 1,3-(4-F)C₆H₃ | bond | 2,4-diF-Ph | bond | 4-F-Ph | HOCH₂CH₂ |
| 45a | bond | 1,3-(4-F)C₆H₃ | bond | 2,4-diF-Ph | bond | 2-F-Ph | HOCH₂CH₂ |
| 46a | bond | 2,6-pyridyl | bond | 2,4-diF-Ph | bond | Ph | HOCH₂CH₂ |
| 47a | bond | 2,6-pyridyl | bond | 2,4-diF-Ph | bond | 4-F-Ph | HOCH₂CH₂ |
| 48a | bond | 2,6-pyridyl | bond | 2,4-diF-Ph | bond | 2-F-Ph | HOCH₂CH₂ |
| 49a | CHMe | 4-Br-Ph | bond | H | bond | 4-F-Ph | allyl |
| 50a | CHMe | 1,4-C₆H₄ | bond | 2,4-diF-Ph | bond | 4-F-Ph | allyl |
| 51a | CHMe | 1,4-C₆H₄ | bond | 2,4-diF-Ph | bond | 4-F-Ph | HOCH₂CH₂ |
| 52a | CHMe | Ph | bond | H | bond | 4-F-Ph | vinyl |
| 53a | CHMe | 4-Br-Ph | bond | H | bond | 4-F-Ph | HOCH₂CH₂ |
| 54a | bond | 2,6-pyridyl | bond | 2-Cl-4-F-Ph | bond | Ph | HOCH₂CH₂ |
| 55a | bond | 2,6-pyridyl | bond | 2-Cl-4-F-Ph | bond | 4-F-Ph | HOCH₂CH₂ |
| 56a | CHMe | 1,4-C₆H₄ | bond | 4-F-Ph | bond | 4-F-Ph | HOCH₂CH₂ |
| 57a | CHMe | c-hex | bond | H | bond | 4-F-Ph | allyl |
| 58a | CHMe | c-hex | bond | H | bond | 4-F-Ph | HOCH₂CH₂CH₂ |
| 59a | CHMe | 1,4-C₆H₄ | bond | c-Pr | bond | 4-F-Ph | allyl |
| 60a | CHMe | 4-MeO₂C-Ph | bond | H | bond | 4-F-Ph | allyl |
| 61a | CHMe | 1,3-C₆H₄ | bond | c-Pr | bond | 4-F-Ph | HOCH₂CH₂CH₂ |
| 62a | CHMe | 4-MeO₂C-Ph | bond | H | bond | 4-F-Ph | HOCH₂CH₂CH₂ |
| 63a | CHEt | 4-Br-Ph | bond | H | bond | 4-F-Ph | allyl |
| 64a | bond | 2,6-(5-Cl)-pyridyl | bond | 4-F-Ph | bond | 2-F-Ph | HOCH₂CH₂ |
| 65a | CHMe | 1,4-C₆H₄ | bond | 2,4-diF-Ph | bond | 4-F-Ph | H₂NCH₂CH₂ |
| 66a | bond | 2,6-(5-Cl)-pyridyl | bond | 2,4-diF-Ph | bond | 2-F-Ph | HOCH₂CH₂ |
| 67a | CHMe | 1,4-C₆H₄ | bond | 2,4-diF-Ph | bond | 4-F-Ph | HOCH₂CH₂CH₂ |
| 68a | CHMe | 1,4-C₆H₄ | bond | 2,4-diF-Ph | bond | 4-F-Ph | MeCH(OH)CH₂ |
| 69a | CHMe | 1,4-C₆H₄ | bond | 2,4-diF-Ph | bond | 4-F-Ph | MeC(=O)CH₂ |
| 70a | CHMe | 1,4-C₆H₄ | bond | 2,4-diF-Ph | bond | 4-F-Ph | HOC(Me)₂CH₂ |
| 71a | CHMe | 1,4-C₆H₄ | bond | 2,4-diF-Ph | bond | 4-F-Ph | MeOCH₂CH₂ |
| 72a | CHMe | 1,4-C₆H₄ | bond | 2,4-diF-Ph | bond | 4-F-Ph | MeNHC(=O)NHCH₂CH₂ |
| 73a | CHMe | 4-Br-Ph | bond | H | bond | 4-F-Ph | HOCH₂CH₂ |
| 74a | CHMe | 4-Br-Ph | bond | H | bond | 4-F-Ph | HOCH₂CH(OH)CH₂ |
| 75a | CHMe | 1,4-C₆H₄ | bond | 2,4-diF-Ph | bond | 4-F-Ph | H₂NCOCH₂CH₂ |
| 76a | CHMe | 1,4-C₆H₄ | bond | 2,4-diF-Ph | bond | 4-F-Ph | MeNHC(=O)CH₂CH₂ |
| 77a | CHMe | 1,4-C₆H₄ | bond | 2,4-diF-Ph | bond | 4-F-Ph | MeCONHCH₂CH₂ |
| 78a | CHMe | 1,4-C₆H₄ | bond | 2,4-diF-Ph | bond | 4-F-Ph | MeNHC(=O)OCH₂CH₂ |
| 79a | CHMe | 1,4-C₆H₄ | bond | 2,4-diF-Ph | bond | 4-F-Ph | H₂NSO₂NHCH₂CH₂ |
| 80a | CHMe | 1,4-C₆H₄ | bond | 2,4-diF-Ph | bond | 4-F-Ph | H₂NSO₂OCH₂CH₂ |
| 81a | CHMe | 1,4-C₆H₄ | bond | 2,4-diF-Ph | bond | 4-F-Ph | (HO)₂P(=O)OCH₂CH₂ |
| 82a | CHMe | 1,4-C₆H₄ | bond | 2,4-diF-Ph | bond | 4-F-Ph | H₂NCH₂C(=O)NHCH₂CH₂ |
| 83a | CHMe | 4-HOCH₂-Ph | bond | H | bond | 4-F-Ph | HOCH₂CH₂CH₂ |
| 84a | CHMe | 4-HOC(Me)₂-Ph | bond | H | bond | 4-F-Ph | allyl |
| 85a | CHMe | 4-Br-Ph | bond | H | bond | 2-thienyl | allyl |
| 86a | CHMe | 1,4-C₆H₄ | bond | 4-F-Ph | bond | Ph | HOCH₂CH₂ |
| 87a | CHMe | 1,4-C₆H₄ | bond | 4-F-Ph | bond | 2-thienyl | allyl |
| 88a | CHMe | 1,4-C₆H₄ | bond | 4-F-Ph | bond | Ph | HOCH₂CH₂CH₂ |
| 89a | CHMe | 1,4-C₆H₄ | bond | 2,4-diF-Ph | bond | Ph | HOCH2CH2 |
| 90a | CHMe | 1,4-C₆H₄ | bond | 2,4-diF-Ph | bond | 2-thienyl | allyl |

TABLE 1-continued

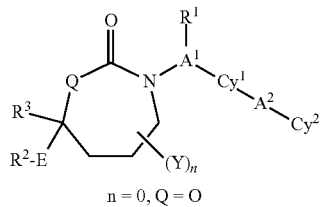

n = 0, Q = O

| Prophetic Example No. | A¹-R¹ | Cy¹ | A² | Cy² | E | R² | R³ |
|---|---|---|---|---|---|---|---|
| 91a | CHMe | 1,4-C$_6$H$_4$ | bond | 4-F-Ph | bond | 2-thienyl | HOCH$_2$CH$_2$CH$_2$ |
| 92a | CHMe | 1,4-C$_6$H$_4$ | bond | 4-F-Ph | bond | 2-thienyl | MeCH(OH)CH$_2$ |
| 93a | CHMe | 1,4-C$_6$H$_4$ | bond | 4-F-Ph | bond | Ph | HOCH$_2$CH(OH)CH$_2$ |
| 94a | CHMe | 1,4-C$_6$H$_4$ | bond | 2,4-diF-Ph | bond | Ph | HOCH$_2$CH$_2$CH$_2$ |
| 95a | CHMe | 1,4-C$_6$H$_4$ | bond | 2,4-diF-Ph | bond | Ph | MeCH(OH)CH$_2$ |
| 96a | CHMe | 1,4-C$_6$H$_4$ | bond | 2,4-diF-Ph | bond | 2-thienyl | HOCH$_2$CH$_2$CH$_2$ |
| 97a | CHMe | Ph | bond | 2,4-diF-Ph | bond | 4-F-Ph | NCCH$_2$CH$_2$ |
| 98a | CHMe | 1,4-C$_6$H$_4$ | bond | 2,4-diF-Ph | bond | Ph | HOCH$_2$CH(OH)CH$_2$ |
| 99a | CHEt | 1,4-C$_6$H$_4$ | bond | 2,4-diF-Ph | bond | 4-F-Ph | HOCH$_2$CH$_2$ |
| 100a | CHMe | 1,4-C$_6$H$_4$ | bond | 2,4-diF-Ph | bond | 4-F-Ph | HOC(=O)CH$_2$CH$_2$ |
| 101a | CHMe | 1,4-C$_6$H$_4$ | bond | 2,4-diF-Ph | bond | 4-F-Ph | HOCH$_2$CH$_2$NHCH$_2$CH$_2$ |
| 102a | CHMe | 1,4-C$_6$H$_4$ | bond | 2,4-diF-Ph | bond | 4-F-Ph | HOCH2C(=O)NHCH$_2$CH$_2$ |
| 103a | CHMe | 1,4-C$_6$H$_4$ | bond | 2,4-diF-Ph | bond | 4-F-Ph | MeOC(=O)NHCH2CH2 |
| 104a | CHMe | 1,4-C$_6$H$_4$ | bond | 2,4-diF-Ph | bond | 4-F-Ph | 2-(4-morpholino)ethyl |
| 105a | CHMe | 1,4-C$_6$H$_4$ | bond | 2,4-diF-Ph | bond | 4-F-Ph | EtNHCONHCH$_2$CH$_2$ |
| 106a | CHMe | 1,4-C$_6$H$_4$ | bond | 2,4-diF-Ph | bond | 4-F-Ph | MeNHC(=NCN)NHCH$_2$CH$_2$ |
| 107a | CHMe | 1,4-C$_6$H$_4$ | bond | 2,4-diF-Ph | bond | 4-F-Ph | MeSO$_2$NHCH$_2$CH$_2$ |
| 108a | CH2Me | 4-Cl-Ph | bond | H | bond | i-Pr | HOCH$_2$CH$_2$CH$_2$ |
| 109a | CH2Me | 4-Me-Ph | bond | H | bond | 4-F-Ph | allyl |
| 110a | CH2Me | 4-MeO-Ph | bond | H | bond | Ph | HOCH$_2$CH$_2$ |
| 111a | CHMe | 4-MeO-Ph | bond | H | bond | 4-F-Ph | allyl |
| 112a | CHMe | 4-HOCH$_2$-Ph | bond | H | bond | Ph | HOCH$_2$CH$_2$CH$_2$ |
| 113a | CHMe | 4-MeO-Ph | bond | H | bond | 4-F-Ph | HOCH$_2$CH$_2$ |
| 114a | CHMe | 4-Cl-Ph | bond | H | bond | 4-F-Ph | allyl |
| 115a | CHMe | c-hex | bond | H | bond | Ph | HOCH$_2$CH(OH)CH$_2$ |
| 116a | CHMe | 4-HOCH$_2$CH$_2$-Ph | bond | H | bond | Ph | HOCH$_2$CH$_2$CH$_2$ |
| 117a | CHMe | 4-MeOCH$_2$-Ph | bond | H | bond | Ph | HOCH$_2$CH$_2$CH$_2$ |
| 118a | CHMe | 4-Br-Ph | bond | H | bond | i-Pr | HOCH$_2$CH$_2$CH$_2$ |
| 119a | CHMe | 4-Cl-Ph | bond | H | bond | 4-F-Ph | HOCH$_2$CH$_2$CH$_2$ |
| 120a | CH2Me | 4-Cl-Ph | bond | H | bond | 4-F-Ph | MeCH(OH)CH2 |
| 121a | CHMe | 4-Br-Ph | bond | H | bond | Ph | allyl |
| 122a | CHMe | 1,4-C$_6$H$_4$ | bond | 3-pyridyl | bond | Ph | HOCH$_2$CH$_2$ |
| 123a | CHMe | 4-MeO-Ph | bond | H | bond | 4-F-Ph | HOCH$_2$CH(OH)CH$_2$ |
| 124a | CHMe | 1,4-C$_6$H$_4$ | bond | 2,4-diF-Ph | bond | i-Pr | HOCH$_2$CH$_2$ |
| 125a | bond | 1-(t-BuOC(=O))pyrrolidin-3-yl | bond | H | bond | Ph | HOCH$_2$CH$_2$CH$_2$ |
| 126a | CHMe | 1,4-C$_6$H$_4$ | bond | 2,4-diF-Ph | bond | 4-F-Ph | MeSO$_2$NHCH$_2$CH$_2$ |
| 127a | CHMe | 1,4-C$_6$H$_4$ | bond | 4-pyridyl | bond | Ph | HOCH$_2$CH$_2$CH$_2$ |
| 128a | CHMe | 1,4-C$_6$H$_4$ | bond | 3-pyridyl | bond | Ph | HOCH$_2$CH$_2$CH$_2$ |
| 129a | CHMe | 1,4-C$_6$H$_4$ | bond | 2,4-diF-Ph | bond | i-Pr | HOCH$_2$CH$_2$CH$_2$ |
| 130a | CHMe | 1,4-C$_6$H$_4$ | bond | 3-pyridyl | bond | 4-F-Ph | HOCH$_2$CH$_2$ |
| 131a | CHMe | 1,4-C$_6$H$_4$ | bond | 2-thienyl | bond | Ph | HOCH$_2$CH$_2$CH$_2$ |
| 132a | CHMe | 1,4-C$_6$H$_4$ | bond | 4-morpholinyl | bond | 4-F-Ph | allyl |
| 133a | CHMe | 1,4-C$_6$H$_4$ | bond | 4-F-Ph | bond | 2-thienyl | HOCH$_2$CH$_2$ |
| 134a | CHMe | 1,4-C$_6$H$_4$ | bond | 4-F-Ph | bond | Ph | NCCH$_2$CH$_2$ |
| 135a | CHEt | 4-Br-Ph | bond | H | bond | Ph | HOCH$_2$CH$_2$CH$_2$ |
| 136a | CHMe | 1,4-C$_6$H$_4$ | bond | 2,4-diF-Ph | bond | 4-F-Ph | HOCH$_2$CH$_2$CH$_2$ |
| 137a | CHMe | 1,4-C$_6$H$_4$ | bond | 1-oxo-3-pyridyl | bond | Ph | HOCH$_2$CH$_2$CH$_2$ |
| 138a | CHMe | 1,4-C$_6$H$_4$ | bond | 2,4-diF-Ph | bond | i-Pr | HOCH$_2$CH(OH)CH$_2$ |
| 139a | CHMe | 1,4-C$_6$H$_4$ | bond | 4-F-Ph | bond | Ph | MeCH(OH)CH$_2$ |
| 140a | CHMe | 1,4-C$_6$H$_4$ | bond | 3-pyridyl | bond | 4-F-Ph | HOCH$_2$CH$_2$CH$_2$ |
| 141a | CHMe | 1,4-C$_6$H$_4$ | bond | 2,4-diF-Ph | bond | Ph | Pr |
| 142a | CHMe | 4-Br-Ph | bond | H | bond | 4-F-Ph | HOCH$_2$CH$_2$CH$_2$ |
| 143a | CHMe | 1,4-C$_6$H$_4$ | bond | 2,4-diF-Ph | bond | 4-F-Ph | MeSO$_2$CH$_2$CH$_2$ |
| 144a | CHMe | 1,4-C$_6$H$_4$ | bond | 5-Me-1,3,4-thiadiazol-2-yl | bond | 4-F-Ph | allyl |
| 145a | CHMe | 1,4-C$_6$H$_4$ | bond | 4-F-Ph | bond | 2-thienyl | HOCH$_2$CH$_2$CH$_2$ |
| 146a | CHMe | 1,4-C$_6$H$_4$ | bond | 2,4-diF-Ph | bond | 2-thienyl | HOCH$_2$CH2 |
| 147a | CHMe | 1,4-C$_6$H$_4$ | bond | 4-F-Ph | bond | Ph | H$_2$NCOCH$_2$CH$_2$ |
| 148a | CHMe | 1,4-C$_6$H$_4$ | bond | 2-MeO-5-pyridyl | bond | Ph | HOCH$_2$CH$_2$CH$_2$ |
| 149a | CHMe | 1,4-C$_6$H$_4$ | bond | 3-pyridyl | bond | 4-F-Ph | H$_2$NCOCH$_2$CH$_2$ |
| 150a | CHEt | 1,4-C$_6$H$_4$ | bond | 4-F-Ph | bond | Ph | HOCH$_2$CH$_2$CH$_2$ |
| 151a | CHMe | 1,4-C$_6$H$_4$ | bond | 4-F-Ph | bond | Ph | HOC(Me)$_2$CH$_2$ |
| 152a | CHEt | 4-Br-Ph | bond | H | bond | Ph | HOCH$_2$CH(OH)CH$_2$ |
| 153a | CHMe | 4-Br-Ph | bond | H | bond | 4-F-Ph | H$_2$NCOCH$_2$CH$_2$ |
| 154a | CHEt | 4-Br-Ph | bond | H | bond | 4-F-Ph | HOCH$_2$CH$_2$CH$_2$ |

TABLE 1-continued

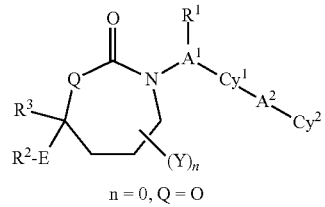

n = 0, Q = O

| Prophetic Example No. | A¹-R¹ | Cy¹ | A² | Cy² | E | R² | R³ |
|---|---|---|---|---|---|---|---|
| 155a | CHMe | 1,4-C$_6$H$_4$ | bond | 2,4-diF-Ph | bond | 4-F-Ph | NCCH$_2$ |
| 156a | CHMe | 1,4-C$_6$H$_4$ | bond | 2,4-diMe-5-thiazolyl | bond | 4-F-Ph | allyl |
| 157a | CHMe | 1,4-C$_6$H$_4$ | bond | 4-F-Ph | bond | 4-F-Ph | HOCH$_2$CH$_2$CH$_2$ |
| 158a | CHMe | 1,4-C$_6$H$_4$ | bond | 4-F-Ph | bond | 2-F-Ph | HOCH$_2$CH$_2$CH$_2$ |
| 159a | CHMe | 1,4-C$_6$H$_4$ | bond | 4-F-Ph | bond | 3-F-Ph | HOCH$_2$CH$_2$CH$_2$ |
| 160a | CHMe | 1,4-C$_6$H$_4$ | bond | 4-F-Ph | bond | Ph | HOC(Me)$_2$CH$_2$CH$_2$ |
| 161a | CHMe | 1,4-C$_6$H$_4$ | bond | 5-MeCO-2-thienyl | bond | Ph | HOCH$_2$CH$_2$CH$_2$ |
| 162a | CHMe | 1,4-C$_6$H$_4$ | bond | 2,4-diF-Ph | bond | Ph | H$_2$NCOCH$_2$CH$_2$ |
| 163a | CHMe | 1,4-C$_6$H$_4$ | bond | 5-(H$_2$NCHMe)-2-thienyl | bond | Ph | HOCH$_2$CH$_2$CH$_2$ |
| 164a | CHEt | 1,4-C$_6$H$_4$ | bond | 4-F-Ph | bond | 4-F-Ph | HOCH$_2$CH$_2$CH$_2$ |
| 165a | CHEt | 1,4-C$_6$H$_4$ | bond | 2,4-diF-Ph | bond | Ph | HOCH$_2$CH$_2$CH$_2$ |
| 166a | CHMe | 1,4-C$_6$H$_4$ | bond | 5-(HOCHMe)-2-thienyl | bond | Ph | HOCH$_2$CH$_2$CH$_2$ |
| 167a | CHEt | 4-Br-Ph | bond | H | bond | 4-F-Ph | HOCH$_2$CH(OH)CH$_2$ |
| 168a | CHMe | 1,4-C$_6$H$_4$ | bond | 2,4-diF-Ph | bond | 4-F-Ph | H$_2$NCH$_2$CH$_2$CH$_2$ |
| 169a | CHMe | 1,4-C$_6$H$_4$ | bond | 2,4-diF-Ph | bond | 4-F-Ph | MeNHCH$_2$CH$_2$ |
| 170a | CHMe | 1,4-C$_6$H$_4$ | bond | 3-(CF$_3$)-1-pyrazolyl | bond | 4-F-Ph | allyl |
| 171a | CHMe | 1,4-C$_6$H$_4$ | bond | 2,4-diF-Ph | bond | Ph | HOC(Me)$_2$CH$_2$CH$_2$ |
| 172a | CHEt | 1,4-C$_6$H$_4$ | bond | 2,4-diF-Ph | bond | 4-F-Ph | HOCH$_2$CH$_2$CH$_2$ |
| 173a | CHMe | 1,4-C$_6$H$_4$ | bond | 2,4-diF-Ph | bond | 4-F-Ph | MeSCH$_2$CH$_2$ |
| 174a | CHMe | Ph | bond | 2,4-diF-Ph | bond | 4-F-Ph | H$_2$NC(=O)NHCH$_2$CH$_2$ |
| 175a | CHMe | 1,4-C$_6$H$_4$ | bond | 2,4-diF-Ph | bond | 4-F-Ph | H$_2$NC(=O)OCH$_2$CH$_2$ |
| 176a | CHMe | 1,4-C$_6$H$_4$ | bond | 2,4-diF-Ph | bond | 4-F-Ph | HOCH$_2$CH$_2$OCH$_2$CH$_2$ |
| 177a | CHMe | 1,4-C$_6$H$_4$ | bond | 2,4-diF-Ph | bond | 4-F-Ph | 2-(1-imidazolyl)ethyl |
| 178a | CHMe | 1,4-C$_6$H$_4$ | bond | 2,4-diF-Ph | bond | 4-F-Ph | MeCONMeCH$_2$CH$_2$ |
| 179a | CHMe | 1,4-C$_6$H$_4$ | bond | 4-F-Ph | bond | Ph | MeSO$_2$NHCH$_2$CH$_2$CH$_2$ |
| 180a | CHMe | 1,4-C$_6$H$_4$ | bond | 2,4-diF-Ph | bond | 4-F-Ph | H$_2$NC(=O)NHCH$_2$CH$_2$CH$_2$ |
| 181a | CHMe | 1,4-C$_6$H$_4$ | bond | 2,4-diF-Ph | bond | 4-F-Ph | H$_2$NC(=O)OCH$_2$CH$_2$CH$_2$ |
| 182a | CHMe | 1,4-C$_6$H$_4$ | bond | 2,4-diF-Ph | bond | 4-F-Ph | 2-(1-aminoimidazol-1-yl)ethyl |
| 183a | CHMe | 1,4-C$_6$H$_4$ | bond | 2,4-diF-Ph | bond | 4-F-Ph | MeNHC(=O)NHCH$_2$CH$_2$ |
| 184a | CHMe | 1,4-C$_6$H$_4$ | bond | 2,4-diF-Ph | bond | 4-F-Ph | H$_2$NC(=O)NHCH$_2$CH(OH)CH$_2$ |
| 185a | CHMe | 1,4-C$_6$H$_4$ | bond | 4-F-Ph | bond | 4-F-Ph | MeSO$_2$NHCH$_2$CH(OH)CH$_2$ |
| 186a | CHMe | 1,4-C$_6$H$_4$ | bond | 4-F-Ph | bond | 4-F-Ph | MeSO$_2$NMeCH$_2$CH(OH)CH$_2$ |
| 187a | CHMe | 1,4-C$_6$H$_4$ | bond | 6-CF$_3$-3-pyridyl | bond | 4-F-Ph | HOCH$_2$CH$_2$CH$_2$ |
| 188a | CHMe | 4-MeO-Ph | bond | H | bond | Ph | HOCH$_2$CH$_2$CH$_2$ |
| 189a | CHMe | 3-F-Ph | bond | H | bond | 4-F-Ph | HOCH$_2$CH$_2$CH$_2$ |
| 190a | CHMe | 2-F-Ph | bond | H | bond | 4-F-Ph | HOCH$_2$CH$_2$CH$_2$ |
| 191a | CHMe | 4-F-Ph | bond | H | bond | 4-F-Ph | HOCH$_2$CH$_2$CH$_2$ |
| 192a | CHMe | 4-MeO-Ph | bond | H | bond | Ph | HOCH$_2$CH(OH)CH$_2$ |
| 193a | CHMe | 4-Cl-Ph | bond | H | bond | Ph | H$_2$NCOCH$_2$CH$_2$ |
| 194a | CHMe | 4-MeO-Ph | bond | H | bond | 4-F-Ph | H$_2$NCOCH$_2$CH$_2$ |
| 195a | CHMe | 4-F$_2$HCO-Ph | bond | H | bond | 4-F-Ph | allyl |
| 196a | CHMe | Ph | bond | 3-pyrazolyl | bond | Ph | HOCH$_2$CH$_2$CH$_2$ |
| 197a | CHMe | 1,4-C$_6$H$_4$ | bond | 5-F-3-pyridyl | bond | Ph | allyl |
| 198a | CHMe | 3-CF$_3$-Ph | bond | H | bond | 4-F-Ph | HOCH$_2$CH$_2$CH$_2$ |
| 199a | CHMe | 4-CF$_3$-Ph | bond | H | bond | 4-F-Ph | HOCH$_2$CH$_2$CH$_2$ |
| 200a | CHMe | 1,4-C$_6$H$_4$ | bond | 3-pyridyl | bond | Ph | H$_2$NCOCH$_2$CH$_2$ |
| 201a | CHMe | 1,4-C$_6$H$_4$ | bond | 4-pyridyl | bond | Ph | H$_2$NCOCH$_2$CH$_2$ |
| 202a | CHMe | 1,4-C$_6$H$_4$ | bond | 4-F-Ph | bond | Ph | HOCH$_2$CH$_2$CH$_2$ |
| 203a | CHMe | 1,4-C$_6$H$_4$ | bond | 5-F-3-pyridyl | bond | Ph | HOCH$_2$CH$_2$CH$_2$ |
| 204a | CHMe | 4-MeO-Ph | bond | H | bond | 4-F-Ph | MeSO$_2$NHCH$_2$CH$_2$ |
| 205a | CHMe | 1,4-C$_6$H$_4$ | bond | 5-F-3-pyridyl | bond | 4-F-Ph | HOCH$_2$CH$_2$CH$_2$ |
| 206a | CHMe | 1,4-C$_6$H$_4$ | bond | 4-F-Ph | bond | Ph | NCC(Me)2CH2 |
| 207a | CHMe | 1,4-C$_6$H$_4$ | bond | 6-MeO-3-pyridyl | bond | Ph | H$_2$NCOCH$_2$CH$_2$ |
| 208a | CHMe | 1,4-C$_6$H$_4$ | bond | 5-MeO-3-pyridyl | bond | 4-F-Ph | HOCH$_2$CH$_2$CH$_2$ |
| 209a | CHMe | 1,4-C$_6$H$_4$ | bond | 5-Cl-3-pyridyl | bond | 4-F-Ph | HOCH$_2$CH$_2$CH$_2$ |
| 210a | CHMe | 1,4-C$_6$H$_4$ | bond | 3-pyridyl | bond | Ph | MeSO$_2$NHCH$_2$CH$_2$ |
| 211a | CHMe | 4-F$_2$HCO-Ph | bond | H | bond | 4-F-Ph | HOCH$_2$CH$_2$CH$_2$ |
| 212a | CHMe | 1,4-C$_6$H$_4$ | bond | 4-F-Ph | bond | Ph | (HO)$_2$P(=O)OCH$_2$CH$_2$CH$_2$ |
| 213a | CHMe | 1,4-C$_6$H$_4$ | bond | 2-Me-4-pyridyl | bond | Ph | HOCH$_2$CH$_2$CH$_2$ |
| 214a | CHMe | 1,4-C$_6$H$_4$ | bond | H | bond | Ph | HOCH$_2$CH$_2$CH$_2$ |
| 215a | CHMe | 1,4-C$_6$H$_4$ | bond | 1-Me-6-oxo-3-(1,6-dihydropyridyl) | bond | Ph | HOCH$_2$CH$_2$CH$_2$ |
| 216a | CHMe | 4-MeO-Ph | bond | H | bond | 4-F-Ph | MeSO$_2$NHCH$_2$CH$_2$ |
| 217a | CHMe | 4-MeO-Ph | bond | H | bond | Ph | H$_2$NCOCH$_2$CH$_2$ |
| 218a | CHMe | 4-F-Ph | bond | H | bond | 4-F-Ph | H$_2$NCOCH$_2$CH$_2$ |

TABLE 1-continued

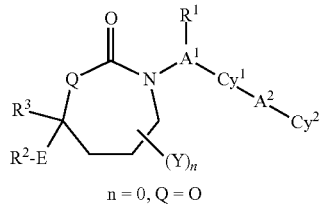

n = 0, Q = O

| Prophetic Example No. | A¹-R¹ | Cy¹ | A² | Cy² | E | R² | R³ |
|---|---|---|---|---|---|---|---|
| 219a | CHMe | c-hex | bond | H | bond | 4-F-Ph | $H_2NCOCH_2CH_2$ |
| 220a | bond | 1,3-(4-F)$C_6H_3$ | bond | 2,4-diF-Ph | bond | 4-F-Ph | $HOCH_2CH_2$ |
| 221a | CHMe | c-hex | bond | H | bond | 4-F-Ph | $MeSO_2NHCH_2CH_2CH_2$ |

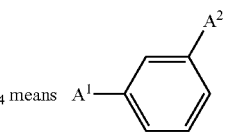

$^a$Cy¹ = 1,3-$C_6H_4$ means

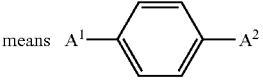

Cy¹ = 1,4-$C_6H_4$ means

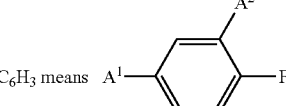

Cy¹ = 1,3-(4-F)$C_6H_3$ means

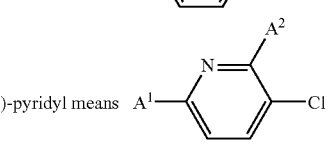

Cy¹ = 2,6-(5-Cl)-pyridyl means

TABLE 2

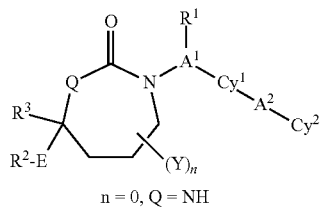

n = 0, Q = NH

| Prophetic Example No. | A¹-R¹ | Cy¹ | A² | Cy² | E | R² | R³ |
|---|---|---|---|---|---|---|---|
| 1b | bond | 3-Me-Ph | bond | H | bond | Ph | Me |
| 2b | bond | 3-Br-Ph | bond | H | bond | Ph | Me |
| 3b | bond | 1,3-$C_6H_4$ | bond | Ph | bond | Ph | Me |
| 4b | bond | 1,3-$C_6H_4$ | bond | 2-Cl-Ph | bond | Ph | Me |
| 5b | bond | 1,3-$C_6H_4$ | bond | 2-NC-Ph | bond | Ph | Me |
| 6b | CH | 1,3-$C_6H_4$ | bond | 2-MeO-Ph | bond | Ph | Me |
| 7b | bond | 1,3-$C_6H_4$ | bond | 2,6-diCl-Ph | bond | Ph | Me |
| 8b | bond | 1,3-$C_6H_4$ | bond | 2,4-diF-Ph | bond | Ph | Me |
| 9b | bond | 1,3-$C_6H_4$ | bond | 3-Cl-Ph | bond | Ph | Me |
| 10b | bond | 1,3-$C_6H_4$ | bond | 3-F-Ph | bond | Ph | Me |
| 11b | bond | 1,3-$C_6H_4$ | bond | 2,5-diF-Ph | bond | Ph | Me |
| 12b | bond | 1,3-$C_6H_4$ | bond | 3,5-diF-Ph | bond | Ph | Me |
| 13b | bond | 1,3-$C_6H_4$ | bond | 4-F-Ph | bond | Ph | Me |
| 14b | bond | 1,3-$C_6H_4$ | bond | 2-F-Ph | bond | Ph | Me |
| 15b | bond | 2,6-pyridyl | bond | 2-Cl-4-F-Ph | bond | 2-F-Ph | $HOCH_2CH_2$ |
| 16b | CHMe | 1,4-$C_6H_4$ | bond | 2,4-diF-Ph | bond | 4-F-Ph | $H_2NC(=O)CH_2$ |
| 17b | CHMe | 1,4-$C_6H_4$ | bond | 2,4-diF-Ph | bond | 4-F-Ph | $HOCH_2CH(OH)CH_2$ |
| 18b | bond | 1,3-$C_6H_4$ | bond | 2,4-diF-Ph | bond | Ph | allyl |

TABLE 2-continued

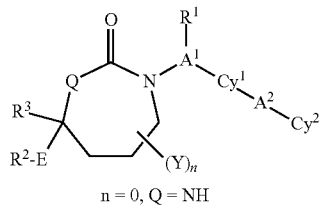

I n = 0, Q = NH

| Prophetic Example No. | $A^1$-$R^1$ | $Cy^1$ | $A^2$ | $Cy^2$ | E | $R^2$ | $R^3$ |
|---|---|---|---|---|---|---|---|
| 19b | bond | 1,3-$C_6H_4$ | bond | 2,4-diF-Ph | bond | Ph | $HOCH_2CH_2$ |
| 20b | bond | 1,3-(4-F)$C_6H_3$ | bond | 4-F-Ph | bond | 4-F-Ph | $HOCH_2CH_2$ |
| 21b | bond | 1,3-(4-F)$C_6H_3$ | bond | 4-F-Ph | bond | 2-F-Ph | $HOCH_2CH_2$ |
| 22b | bond | 1,3-$C_6H_4$ | bond | 2-Cl-4-F-Ph | bond | Ph | $HOCH_2CH_2$ |
| 23b | bond | 1,3-$C_6H_4$ | bond | 2,6-diCl-Ph | bond | Ph | $HOCH_2CH_2$ |
| 24b | bond | 1,3-$C_6H_4$ | bond | 2,4-diF-Ph | bond | Ph | $H_2NC(=O)CH_2$ |
| 25b | CH | 1,3-$C_6H_4$ | bond | 2,4-diF-Ph | bond | Ph | $HOCH_2CH(OH)CH_2$ |
| 26b | bond | 1,3-$C_6H_4$ | bond | 2,4-diF-Ph | bond | Ph | $HOCH_2CH_2CH_2$ |
| 27b | bond | 1,3-$C_6H_4$ | bond | Ph | bond | 3-Cl-Ph | Me |
| 28b | bond | 1,3-$C_6H_4$ | bond | 2,4-diF-Ph | bond | 2-pyridyl | Me |
| 29b | CHMe | Ph | bond | H | bond | Ph | Me |
| 30b | CHMe | 3-MeO-Ph | bond | H | bond | Ph | Me |
| 31b | CHMe | 4-MeO-Ph | bond | H | bond | Ph | Me |
| 32b | CHMe | Ph | bond | H | bond | 2-Me-Ph | Me |
| 33b | CHMe | Ph | bond | H | bond | 4-Me-Ph | Me |
| 34b | CHMe | Ph | bond | H | bond | 4-MeS-Ph | Me |
| 35b | CHMe | Ph | bond | H | bond | 4-F-Ph | allyl |
| 36b | bond | 1,3-$C_6H_4$ | bond | 4-F-Ph | bond | Ph | $HOCH_2CH_2$ |
| 37b | CHMe | Ph | bond | H | bond | 4-F-Ph | $HOCH_2CH_2$ |
| 38b | bond | 1,3-$C_6H_4$ | bond | 2,4-diF-Ph | bond | Ph | $MeSO_2NHCH_2CH_2$ |
| 39b | bond | 1,3-(4-F)$C_6H3$ | bond | 2-Cl-4-F-Ph | bond | 4-F-Ph | $HOCH_2CH_2$ |
| 40b | bond | 1,3-$C_6H_4$ | bond | 2-Cl-4-F-Ph | bond | Ph | $HOCH_2CH_2$ |
| 41b | bond | 2,6-pyridyl | bond | 4-F-Ph | bond | Ph | $HOCH_2CH_2$ |
| 42b | bond | 2,6-pyridyl | bond | 4-F-Ph | bond | 4-F-Ph | $HOCH_2CH_2$ |
| 43b | bond | 2,6-pyridyl | bond | 4-F-Ph | bond | 2-F-Ph | $HOCH_2CH_2$ |
| 44b | bond | 1,3-(4-F)$C_6H_3$ | bond | 2,4-diF-Ph | bond | 4-F-Ph | $HOCH_2CH_2$ |
| 45b | bond | 1,3-(4-F)$C_6H_3$ | bond | 2,4-diF-Ph | bond | 2-F-Ph | $HOCH_2CH_2$ |
| 46b | bond | 2,6-pyridyl | bond | 2,4-diF-Ph | bond | Ph | $HOCH_2CH_2$ |
| 47b | bond | 2,6-pyridyl | bond | 2,4-diF-Ph | bond | 4-F-Ph | $HOCH_2CH_2$ |
| 48b | bond | 2,6-pyridyl | bond | 2,4-diF-Ph | bond | 2-F-Ph | $HOCH_2CH_2$ |
| 49b | CHMe | 4-Br-Ph | bond | H | bond | 4-F-Ph | allyl |
| 50b | CHMe | 1,4-$C_6H_4$ | bond | 2,4-diF-Ph | bond | 4-F-Ph | allyl |
| 51b | CHMe | 1,4-$C_6H_4$ | bond | 2,4-diF-Ph | bond | 4-F-Ph | $HOCH_2CH_2$ |
| 52b | CHMe | Ph | bond | H | bond | 4-F-Ph | vinyl |
| 53b | CHMe | 4-Br-Ph | bond | H | bond | 4-F-Ph | $HOCH_2CH_2$ |
| 54b | bond | 2,6-pyridyl | bond | 2-Cl-4-F-Ph | bond | Ph | $HOCH_2CH_2$ |
| 55b | bond | 2,6-pyridyl | bond | 2-Cl-4-F-Ph | bond | 4-F-Ph | $HOCH_2CH_2$ |
| 56b | CHMe | 1,4-$C_6H_4$ | bond | 4-F-Ph | bond | 4-F-Ph | $HOCH_2CH_2$ |
| 57b | CHMe | c-hex | bond | H | bond | 4-F-Ph | allyl |
| 58b | CHMe | c-hex | bond | H | bond | 4-F-Ph | $HOCH_2CH_2CH_2$ |
| 59b | CHMe | 1,4-$C_6H_4$ | bond | c-Pr | bond | 4-F-Ph | allyl |
| 60b | CHMe | 4-MeO$_2$C-Ph | bond | H | bond | 4-F-Ph | allyl |
| 61b | CHMe | 1,3-$C_6H_4$ | bond | c-Pr | bond | 4-F-Ph | $HOCH_2CH_2CH_2$ |
| 62b | CHMe | 4-MeO$_2$C-Ph | bond | H | bond | 4-F-Ph | $HOCH_2CH_2CH_2$ |
| 63b | CHEt | 4-Br-Ph | bond | H | bond | 4-F-Ph | allyl |
| 64b | bond | 2,6-(5-Cl)-pyridyl | bond | 4-F-Ph | bond | 2-F-Ph | $HOCH_2CH_2$ |
| 65b | CHMe | 1,4-$C_6H_4$ | bond | 2,4-diF-Ph | bond | 4-F-Ph | $H_2NCH_2CH_2$ |
| 66b | bond | 2,6-(5-Cl)-pyridyl | bond | 2,4-diF-Ph | bond | 2-F-Ph | $HOCH_2CH_2$ |
| 67b | CHMe | 1,4-$C_6H_4$ | bond | 2,4-diF-Ph | bond | 4-F-Ph | $HOCH_2CH_2CH_2$ |
| 68b | CHMe | 1,4-$C_6H_4$ | bond | 2,4-diF-Ph | bond | 4-F-Ph | $MeCH(OH)CH_2$ |
| 69b | CHMe | 1,4-$C_6H_4$ | bond | 2,4-diF-Ph | bond | 4-F-Ph | $MeC(=O)CH_2$ |
| 70b | CHMe | 1,4-$C_6H_4$ | bond | 2,4-diF-Ph | bond | 4-F-Ph | $HOC(Me)_2CH_2$ |
| 71b | CHMe | 1,4-$C_6H_4$ | bond | 2,4-diF-Ph | bond | 4-F-Ph | $MeOCH_2CH_2$ |
| 72b | CHMe | 1,4-$C_6H_4$ | bond | 2,4-diF-Ph | bond | 4-F-Ph | $MeNHC(=O)NHCH_2CH_2$ |
| 73b | CHMe | 4-Br-Ph | bond | H | bond | 4-F-Ph | $HOCH_2CH_2$ |
| 74b | CHMe | 4-Br-Ph | bond | H | bond | 4-F-Ph | $HOCH_2CH(OH)CH_2$ |
| 75b | CHMe | 1,4-$C_6H_4$ | bond | 2,4-diF-Ph | bond | 4-F-Ph | $H_2NCOCH_2CH_2$ |
| 76b | CHMe | 1,4-$C_6H_4$ | bond | 2,4-diF-Ph | bond | 4-F-Ph | $MeNHC(=O)CH_2CH_2$ |
| 77b | CHMe | 1,4-$C_6H_4$ | bond | 2,4-diF-Ph | bond | 4-F-Ph | $MeCONHCH_2CH_2$ |
| 78b | CHMe | 1,4-$C_6H_4$ | bond | 2,4-diF-Ph | bond | 4-F-Ph | $MeNHC(=O)OCH_2CH_2$ |
| 79b | CHMe | 1,4-$C_6H_4$ | bond | 2,4-diF-Ph | bond | 4-F-Ph | $H_2NSO_2NHCH_2CH_2$ |
| 80b | CHMe | 1,4-$C_6H_4$ | bond | 2,4-diF-Ph | bond | 4-F-Ph | $H_2NSO_2OCH_2CH_2$ |
| 81b | CHMe | 1,4-$C_6H_4$ | bond | 2,4-diF-Ph | bond | 4-F-Ph | $(HO)_2P(=O)OCH_2CH_2$ |
| 82b | CHMe | 1,4-$C_6H_4$ | bond | 2,4-diF-Ph | bond | 4-F-Ph | $H_2NCH_2C(=O)NHCH_2CH_2$ |
| 83b | CHMe | 4-HOCH$_2$-Ph | bond | H | bond | 4-F-Ph | $HOCH_2CH_2CH_2$ |

TABLE 2-continued

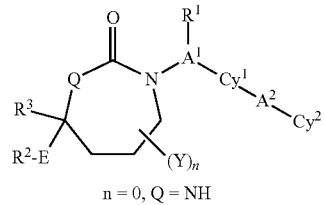

n = 0, Q = NH

| Prophetic Example No. | A¹-R¹ | Cy¹ | A² | Cy² | E | R² | R³ |
|---|---|---|---|---|---|---|---|
| 84b | CHMe | 4-HOC(Me)$_2$-Ph | bond | H | bond | 4-F-Ph | allyl |
| 85b | CHMe | 4-Br-Ph | bond | H | bond | 2-thienyl | allyl |
| 86b | CHMe | 1,4-C$_6$H$_4$ | bond | 4-F-Ph | bond | Ph | HOCH$_2$CH$_2$ |
| 87b | CHMe | 1,4-C$_6$H$_4$ | bond | 4-F-Ph | bond | 2-thienyl | allyl |
| 88b | CHMe | 1,4-C$_6$H$_4$ | bond | 4-F-Ph | bond | Ph | HOCH$_2$CH$_2$CH$_2$ |
| 89b | CHMe | 1,4-C$_6$H$_4$ | bond | 2,4-diF-Ph | bond | Ph | HOCH2CH2 |
| 90b | CHMe | 1,4-C$_6$H$_4$ | bond | 2,4-diF-Ph | bond | 2-thienyl | allyl |
| 91b | CHMe | 1,4-C$_6$H$_4$ | bond | 4-F-Ph | bond | 2-thienyl | HOCH$_2$CH$_2$CH$_2$ |
| 92b | CHMe | 1,4-C$_6$H$_4$ | bond | 4-F-Ph | bond | 2-thienyl | MeCH(OH)CH$_2$ |
| 93b | CHMe | 1,4-C$_6$H$_4$ | bond | 4-F-Ph | bond | Ph | HOCH$_2$CH(OH)CH$_2$ |
| 94b | CHMe | 1,4-C$_6$H$_4$ | bond | 2,4-diF-Ph | bond | Ph | HOCH$_2$CH$_2$CH$_2$ |
| 95b | CHMe | 1,4-C$_6$H$_4$ | bond | 2,4-diF-Ph | bond | Ph | MeCH(OH)CH$_2$ |
| 96b | CHMe | 1,4-C$_6$H$_4$ | bond | 2,4-diF-Ph | bond | 2-thienyl | HOCH$_2$CH$_2$CH$_2$ |
| 97b | CHMe | 1,4-C$_6$H$_4$ | bond | 2,4-diF-Ph | bond | 4-F-Ph | NCCH$_2$CH$_2$ |
| 98b | CHMe | Ph | bond | 2,4-diF-Ph | bond | Ph | HOCH$_2$CH(OH)CH$_2$ |
| 99b | CHEt | 1,4-C$_6$H$_4$ | bond | 2,4-diF-Ph | bond | 4-F-Ph | HOCH$_2$CH$_2$ |
| 100b | CHMe | 1,4-C$_6$H$_4$ | bond | 2,4-diF-Ph | bond | 4-F-Ph | HOC(=O)CH$_2$CH$_2$ |
| 101b | CHMe | 1,4-C$_6$H$_4$ | bond | 2,4-diF-Ph | bond | 4-F-Ph | HOCH$_2$CH$_2$NHCH$_2$CH$_2$ |
| 102b | CHMe | 1,4-C$_6$H$_4$ | bond | 2,4-diF-Ph | bond | 4-F-Ph | HOCH2C(=O)NHCH$_2$CH$_2$ |
| 103b | CHMe | 1,4-C$_6$H$_4$ | bond | 2,4-diF-Ph | bond | 4-F-Ph | MeOC(=O)NHCH2CH2 |
| 104b | CHMe | 1,4-C$_6$H$_4$ | bond | 2,4-diF-Ph | bond | 4-F-Ph | 2-(4-morpholino)ethyl |
| 105b | CHMe | 1,4-C$_6$H$_4$ | bond | 2,4-diF-Ph | bond | 4-F-Ph | EtNHCONHCH$_2$CH$_2$ |
| 106b | CHMe | 1,4-C$_6$H$_4$ | bond | 2,4-diF-Ph | bond | 4-F-Ph | MeNHC(=NCN)NHCH$_2$CH$_2$ |
| 107b | CHMe | 1,4-C$_6$H$_4$ | bond | 2,4-diF-Ph | bond | 4-F-Ph | MeSO$_2$NHCH$_2$CH$_2$CH$_2$ |
| 108b | CH2Me | 4-Cl-Ph | bond | H | bond | i-Pr | HOCH$_2$CH$_2$CH$_2$ |
| 109b | CH2Me | 4-Me-Ph | bond | H | bond | 4-F-Ph | allyl |
| 110b | CH2Me | 4-MeO-Ph | bond | H | bond | Ph | HOCH$_2$CH$_2$ |
| 111b | CHMe | 4-MeO-Ph | bond | H | bond | 4-F-Ph | allyl |
| 112b | CHMe | 4-HOCH$_2$-Ph | bond | H | bond | Ph | HOCH$_2$CH$_2$CH$_2$ |
| 113b | CHMe | 4-MeO-Ph | bond | H | bond | 4-F-Ph | HOCH$_2$CH$_2$ |
| 114b | CHMe | 4-Cl-Ph | bond | H | bond | 4-F-Ph | allyl |
| 115b | CHMe | c-hex | bond | H | bond | Ph | HOCH$_2$CH(OH)CH$_2$ |
| 116b | CHMe | 4-HOCH$_2$CH$_2$-Ph | bond | H | bond | Ph | HOCH$_2$CH$_2$CH$_2$ |
| 117b | CHMe | 4-MeOCH$_2$-Ph | bond | H | bond | Ph | HOCH$_2$CH$_2$CH$_2$ |
| 118b | CHMe | 4-Br-Ph | bond | H | bond | i-Pr | HOCH$_2$CH$_2$CH$_2$ |
| 119b | CHMe | 4-Cl-Ph | bond | H | bond | 4-F-Ph | HOCH$_2$CH$_2$CH$_2$ |
| 120b | CH2Me | 4-Cl-Ph | bond | H | bond | 4-F-Ph | MeCH(OH)CH2 |
| 121b | CHMe | 4-Br-Ph | bond | H | bond | Ph | allyl |
| 122b | CHMe | 1,4-C$_6$H$_4$ | bond | 3-pyridyl | bond | Ph | HOCH$_2$CH$_2$ |
| 123b | CHMe | 4-MeO-Ph | bond | H | bond | 4-F-Ph | HOCH$_2$CH(OH)CH$_2$ |
| 124b | CHMe | 1,4-C$_6$H$_4$ | bond | 2,4-diF-Ph | bond | i-Pr | HOCH$_2$CH$_2$ |
| 125b | bond | 1-(t-BuOC(=O))pyrrolidin-3-yl | bond | H | bond | Ph | HOCH$_2$CH$_2$CH$_2$ |
| 126b | CHMe | 1,4-C$_6$H$_4$ | bond | 2,4-diF-Ph | bond | 4-F-Ph | MeSO$_2$NHCH$_2$CH$_2$ |
| 127b | CHMe | 1,4-C$_6$H$_4$ | bond | 4-pyridyl | bond | Ph | HOCH$_2$CH$_2$CH$_2$ |
| 128b | CHMe | 1,4-C$_6$H$_4$ | bond | 3-pyridyl | bond | Ph | HOCH$_2$CH$_2$CH$_2$ |
| 129b | CHMe | 1,4-C$_6$H$_4$ | bond | 2,4-diF-Ph | bond | i-Pr | HOCH$_2$CH$_2$CH$_2$ |
| 130b | CHMe | 1,4-C$_6$H$_4$ | bond | 3-pyridyl | bond | 4-F-Ph | HOCH$_2$CH$_2$ |
| 131b | CHMe | 1,4-C$_6$H$_4$ | bond | 2-2-thienyl | bond | Ph | HOCH$_2$CH$_2$CH$_2$ |
| 132b | CHMe | 1,4-C$_6$H$_4$ | bond | 4-morpholinyl | bond | 4-F-Ph | allyl |
| 133b | CHMe | 1,4-C$_6$H$_4$ | bond | 4-F-Ph | bond | 2-thienyl | HOCH$_2$CH$_2$ |
| 134b | CHMe | 1,4-C$_6$H$_4$ | bond | 4-F-Ph | bond | Ph | NCCH$_2$CH$_2$ |
| 135b | CHEt | 4-Br-Ph | bond | H | bond | Ph | HOCH$_2$CH$_2$CH$_2$ |
| 136b | CHMe | 1,4-C$_6$H$_4$ | bond | 2,4-diF-Ph | bond | 4-F-Ph | HOCH$_2$CH$_2$CH$_2$ |
| 137b | CHMe | 1,4-C$_6$H$_4$ | bond | 1-oxo-3-pyridyl | bond | Ph | HOCH$_2$CH$_2$CH$_2$ |
| 138b | CHMe | 1,4-C$_6$H$_4$ | bond | 2,4-diF-Ph | bond | i-Pr | HOCH$_2$CH(OH)CH$_2$ |
| 139b | CHMe | 1,4-C$_6$H$_4$ | bond | 4-F-Ph | bond | Ph | MeCH(OH)CH$_2$ |
| 140b | CHMe | 1,4-C$_6$H$_4$ | bond | 3-pyridyl | bond | 4-F-Ph | HOCH$_2$CH$_2$CH$_2$ |
| 141b | CHMe | 1,4-C$_6$H$_4$ | bond | 2,4-diF-Ph | bond | Ph | Pr |
| 142b | CHMe | 4-Br-Ph | bond | H | bond | 4-F-Ph | HOCH$_2$CH$_2$CH$_2$ |
| 143b | CHMe | 1,4-C$_6$H$_4$ | bond | 2,4-diF-Ph | bond | 4-F-Ph | MeSO$_2$CH$_2$CH$_2$ |
| 144b | CHMe | 1,4-C$_6$H$_4$ | bond | 5-Me-1,3,4-thiadiazol-2-yl | bond | 4-F-Ph | allyl |
| 145b | CHMe | 1,4-C$_6$H$_4$ | bond | 4-F-Ph | bond | 2-thienyl | HOCH$_2$CH$_2$CH$_2$ |
| 146b | CHMe | 1,4-C$_6$H$_4$ | bond | 2,4-diF-Ph | bond | 2-thienyl | HOCH$_2$CH2 |
| 147b | CHMe | 1,4-C$_6$H$_4$ | bond | 4-F-Ph | bond | Ph | H$_2$NCOCH$_2$CH$_2$ |
| 148b | CHMe | 1,4-C$_6$H$_4$ | bond | 2-MeO-5-pyridyl | bond | Ph | HOCH$_2$CH$_2$CH$_2$ |

TABLE 2-continued

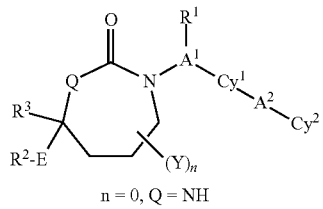

n = 0, Q = NH

| Prophetic Example No. | A¹-R¹ | Cy¹ | A² | Cy² | E | R² | R³ |
|---|---|---|---|---|---|---|---|
| 149b | CHMe | 1,4-C$_6$H$_4$ | bond | 3-pyridyl | bond | 4-F-Ph | H$_2$NCOCH$_2$CH$_2$ |
| 150b | CHEt | 1,4-C$_6$H$_4$ | bond | 4-F-Ph | bond | Ph | HOCH$_2$CH$_2$CH$_2$ |
| 151b | CHMe | 1,4-C$_6$H$_4$ | bond | 4-F-Ph | bond | Ph | HOC(Me)$_2$CH$_2$ |
| 152b | CHEt | 4-Br-Ph | bond | H | bond | Ph | HOCH$_2$CH(OH)CH$_2$ |
| 153b | CHEt | 4-Br-Ph | bond | H | bond | 4-F-Ph | H$_2$NCOCH$_2$CH$_2$ |
| 154b | CHEt | 4-Br-Ph | bond | H | bond | 4-F-Ph | HOCH$_2$CH$_2$CH$_2$ |
| 155b | CHMe | 1,4-C$_6$H$_4$ | bond | 2,4-diF-Ph | bond | 4-F-Ph | NCCH$_2$ |
| 156b | CHMe | 1,4-C$_6$H$_4$ | bond | 2,4-diMe-5-thiazolyl | bond | 4-F-Ph | allyl |
| 157b | CHMe | 1,4-C$_6$H$_4$ | bond | 4-F-Ph | bond | 4-F-Ph | HOCH$_2$CH$_2$CH$_2$ |
| 158b | CHMe | 1,4-C$_6$H$_4$ | bond | 4-F-Ph | bond | 2-F-Ph | HOCH$_2$CH$_2$CH$_2$ |
| 159b | CHMe | 1,4-C$_6$H$_4$ | bond | 4-F-Ph | bond | 3-F-Ph | HOCH$_2$CH$_2$CH$_2$ |
| 160b | CHMe | 1,4-C$_6$H$_4$ | bond | 4-F-Ph | bond | Ph | HOC(Me)$_2$CH$_2$CH$_2$ |
| 161b | CHMe | 1,4-C$_6$H$_4$ | bond | 5-MeCO-2-thienyl | bond | Ph | HOCH$_2$CH$_2$CH$_2$ |
| 162b | CHMe | 1,4-C$_6$H$_4$ | bond | 2,4-diF-Ph | bond | Ph | H$_2$NCOCH$_2$CH$_2$ |
| 163b | CHMe | 1,4-C$_6$H$_4$ | bond | 5-(H$_2$NCHMe)-2-thienyl | bond | Ph | HOCH$_2$CH$_2$CH$_2$ |
| 164b | CHEt | 1,4-C$_6$H$_4$ | bond | 4-F-Ph | bond | 4-F-Ph | HOCH$_2$CH$_2$CH$_2$ |
| 165b | CHEt | 1,4-C$_6$H$_4$ | bond | 2,4-diF-Ph | bond | Ph | HOCH$_2$CH$_2$CH$_2$ |
| 166b | CHMe | 1,4-C$_6$H$_4$ | bond | 5-(HOCHMe)-2-thienyl | bond | Ph | HOCH$_2$CH$_2$CH$_2$ |
| 167b | CHEt | 4-Br-Ph | bond | H | bond | 4-F-Ph | HOCH$_2$CH(OH)CH$_2$ |
| 168b | CHMe | 1,4-C$_6$H$_4$ | bond | 2,4-diF-Ph | bond | 4-F-Ph | H$_2$NCH$_2$CH$_2$CH$_2$ |
| 169b | CHMe | 1,4-C$_6$H$_4$ | bond | 2,4-diF-Ph | bond | 4-F-Ph | MeNHCH$_2$CH$_2$ |
| 170b | CHMe | 1,4-C$_6$H$_4$ | bond | 3-(CF$_3$)-1-pyrazolyl | bond | 4-F-Ph | allyl |
| 171b | CHMe | 1,4-C$_6$H$_4$ | bond | 2,4-diF-Ph | bond | Ph | HOC(Me)$_2$CH$_2$CH$_2$ |
| 172b | CHEt | 1,4-C$_6$H$_4$ | bond | 2,4-diF-Ph | bond | 4-F-Ph | HOCH$_2$CH$_2$CH$_2$ |
| 173b | CHMe | 1,4-C$_6$H$_4$ | bond | 2,4-diF-Ph | bond | 4-F-Ph | MeSCH$_2$CH$_2$ |
| 174b | CHMe | Ph | bond | 2,4-diF-Ph | bond | 4-F-Ph | H$_2$NC(=O)NHCH$_2$CH$_2$ |
| 175b | CHMe | 1,4-C$_6$H$_4$ | bond | 2,4-diF-Ph | bond | 4-F-Ph | H$_2$NC(=O)OCH$_2$CH$_2$ |
| 176b | CHMe | 1,4-C$_6$H$_4$ | bond | 2,4-diF-Ph | bond | 4-F-Ph | HOCH$_2$CH$_2$OCH$_2$CH$_2$ |
| 177b | CHMe | 1,4-C$_6$H$_4$ | bond | 2,4-diF-Ph | bond | 4-F-Ph | 2-(1-imidazolyl)ethyl |
| 178b | CHMe | 1,4-C$_6$H$_4$ | bond | 2,4-diF-Ph | bond | 4-F-Ph | MeCONMeCH$_2$CH$_2$ |
| 179b | CHMe | 1,4-C$_6$H$_4$ | bond | 4-F-Ph | bond | Ph | MeSO$_2$NHCH$_2$CH$_2$CH$_2$ |
| 180b | CHMe | 1,4-C$_6$H$_4$ | bond | 2,4-diF-Ph | bond | 4-F-Ph | H$_2$NC(=O)NHCH$_2$CH$_2$CH$_2$ |
| 181b | CHMe | 1,4-C$_6$H$_4$ | bond | 2,4-diF-Ph | bond | 4-F-Ph | H$_2$NC(=O)OCH$_2$CH$_2$CH$_2$ |
| 182b | CHMe | 1,4-C$_6$H$_4$ | bond | 2,4-diF-Ph | bond | 4-F-Ph | 2-(1-aminoimidazol-1-yl)ethyl |
| 183b | CHMe | 1,4-C$_6$H$_4$ | bond | 2,4-diF-Ph | bond | 4-F-Ph | MeNHC(=O)NHCH$_2$CH$_2$ |
| 184b | CHMe | 1,4-C$_6$H$_4$ | bond | 2,4-diF-Ph | bond | 4-F-Ph | H$_2$NC(=O)NHCH$_2$CH(OH)CH$_2$ |
| 185b | CHMe | 1,4-C$_6$H$_4$ | bond | 4-F-Ph | bond | 4-F-Ph | MeSO$_2$NHCH$_2$CH(OH)CH$_2$ |
| 186b | CHMe | 1,4-C$_6$H$_4$ | bond | 4-F-Ph | bond | 4-F-Ph | MeSO$_2$NMeCH$_2$CH(OH)CH$_2$ |
| 187b | CHMe | 1,4-C$_6$H$_4$ | bond | 6-CF$_3$-3-pyridyl | bond | 4-F-Ph | HOCH$_2$CH$_2$CH$_2$ |
| 188b | CHMe | 4-MeO-Ph | bond | H | bond | Ph | HOCH$_2$CH$_2$CH$_2$ |
| 189b | CHMe | 3-F-Ph | bond | H | bond | 4-F-Ph | HOCH$_2$CH$_2$CH$_2$ |
| 190b | CHMe | 2-F-Ph | bond | H | bond | 4-F-Ph | HOCH$_2$CH$_2$CH$_2$ |
| 191b | CHMe | 4-F-Ph | bond | H | bond | 4-F-Ph | HOCH$_2$CH$_2$CH$_2$ |
| 192b | CHMe | 4-MeO-Ph | bond | H | bond | Ph | HOCH$_2$CH(OH)CH$_2$ |
| 193b | CHMe | 4-Cl-Ph | bond | H | bond | Ph | H$_2$NCOCH$_2$CH$_2$ |
| 194b | CHMe | 4-MeO-Ph | bond | H | bond | 4-F-Ph | H$_2$NCOCH$_2$CH$_2$ |
| 195b | CHMe | 4-F$_2$HCO-Ph | bond | H | bond | 4-F-Ph | allyl |
| 196b | CHMe | Ph | bond | 3-pyrazolyl | bond | Ph | HOCH$_2$CH$_2$CH$_2$ |
| 197b | CHMe | 1,4-C$_6$H$_4$ | bond | 5-F-3-pyridyl | bond | Ph | allyl |
| 198b | CHMe | 3-CF$_3$-Ph | bond | H | bond | 4-F-Ph | HOCH$_2$CH$_2$CH$_2$ |
| 199b | CHMe | 4-CF$_3$-Ph | bond | H | bond | 4-F-Ph | HOCH$_2$CH$_2$CH$_2$ |
| 200b | CHMe | 1,4-C$_6$H$_4$ | bond | 3-pyridyl | bond | Ph | H$_2$NCOCH$_2$CH$_2$ |
| 201b | CHMe | 1,4-C$_6$H$_4$ | bond | 4-pyridyl | bond | Ph | H$_2$NCOCH$_2$CH$_2$ |
| 202b | CHMe | 1,4-C$_6$H$_4$ | bond | 4-F-Ph | bond | Ph | HOCH$_2$CH$_2$CH$_2$ |
| 203b | CHMe | 1,4-C$_6$H$_4$ | bond | 5-F-3-pyridyl | bond | Ph | HOCH$_2$CH$_2$CH$_2$ |
| 204b | CHMe | 4-MeO-Ph | bond | H | bond | 4-F-Ph | MeSO$_2$NHCH$_2$CH$_2$ |
| 205b | CHMe | 1,4-C$_6$H$_4$ | bond | 5-F-3-pyridyl | bond | 4-F-Ph | HOCH$_2$CH$_2$CH$_2$ |
| 206b | CHMe | 1,4-C$_6$H$_4$ | bond | 4-F-Ph | bond | Ph | NCC(Me)2CH2 |
| 207b | CHMe | 1,4-C$_6$H$_4$ | bond | 6-MeO-3-pyridyl | bond | Ph | H$_2$NCOCH$_2$CH$_2$ |
| 208b | CHMe | 1,4-C$_6$H$_4$ | bond | 5-MeO-3-pyridyl | bond | 4-F-Ph | HOCH$_2$CH$_2$CH$_2$ |
| 209b | CHMe | 1,4-C$_6$H$_4$ | bond | 5-Cl-3-pyridyl | bond | 4-F-Ph | HOCH$_2$CH$_2$CH$_2$ |
| 210b | CHMe | 1,4-C$_6$H$_4$ | bond | 3-pyridyl | bond | Ph | MeSO$_2$NHCH$_2$CH$_2$ |
| 211b | CHMe | 4-F$_2$HCO-Ph | bond | H | bond | 4-F-Ph | HOCH$_2$CH$_2$CH$_2$ |
| 212b | CHMe | 1,4-C$_6$H$_4$ | bond | 4-F-Ph | bond | Ph | (HO)$_2$P(=O)OCH$_2$CH$_2$CH$_2$ |
| 213b | CHMe | 1,4-C$_6$H$_4$ | bond | 2-Me-4-pyridyl | bond | 4-F-Ph | HOCH$_2$CH$_2$CH$_2$ |

TABLE 2-continued

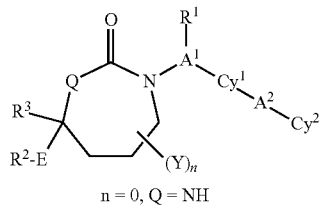

n = 0, Q = NH

| Prophetic Example No. | A¹-R¹ | Cy¹ | A² | Cy² | E | R² | R³ |
|---|---|---|---|---|---|---|---|
| 214b | CHMe | 1,4-C$_6$H$_4$ | bond | H | bond | Ph | HOCH$_2$CH$_2$CH$_2$ |
| 215b | CHMe | 1,4-C$_6$H$_4$ | bond | 1-Me-6-oxo-3-(1,6-dihydropyridyl) | bond | Ph | HOCH$_2$CH$_2$CH$_2$ |
| 216b | CHMe | 4-MeO-Ph | bond | H | bond | 4-F-Ph | MeSO$_2$NHCH$_2$CH$_2$CH$_2$ |
| 217b | CHMe | 4-MeO-Ph | bond | H | bond | Ph | H$_2$NCOCH$_2$CH$_2$ |
| 218b | CHMe | 4-F-Ph | bond | H | bond | 4-F-Ph | H$_2$NCOCH$_2$CH$_2$ |
| 219b | CHMe | c-hex | bond | H | bond | 4-F-Ph | H$_2$NCOCH$_2$CH$_2$ |
| 220b | bond | 1,3-(4-F)C$_6$H$_3$ | bond | 2,4-diF-Ph | bond | 4-F-Ph | HOCH$_2$CH$_2$ |
| 221b | CHMe | c-hex | bond | H | bond | 4-F-Ph | MeSO$_2$NHCH$_2$CH$_2$CH$_2$ |

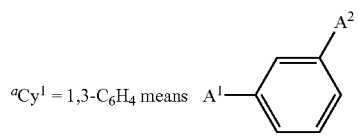

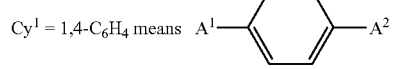

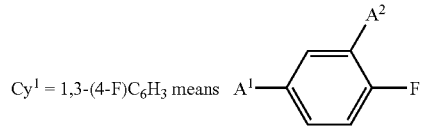

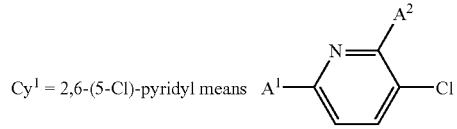

Biological Test Example 1

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxysteroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at rt. The reaction was stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

Biological Test Example 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% CO$_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 µL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 µL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE OF BIOLOGICAL ASSAY RESULTS

| Compound | $IC_{50}$ Range[a] | Biological Test Example 1 Average % inhibition at 100 nM |
|---|---|---|
| EXAMPLE 1 | ++ | 95.6 |
| EXAMPLE 2 Isomer 1 | ++ | 96.3 |
| EXAMPLE 2 Isomer 2 | ++ | 96.2 |
| EXAMPLE 3 Isomer 1 | ++ | 85.8 |
| EXAMPLE 3 Isomer 2 | ++ | 97.6 |
| EXAMPLE 4 | ++ | 95.8 |
| EXAMPLE 5 | ++ | 93.7 |
| EXAMPLE 6 | ++ | 95.5 |
| EXAMPLE 7 | ++ | 93.0 |
| EXAMPLE 8 | ++ | 97.5 |
| EXAMPLE 9 | ++ | 95.2 |
| EXAMPLE 10 | ++ | 97.1 |
| EXAMPLE 11 | ++ | 98.3 |
| EXAMPLE 12 | ++ | 92.9 |
| EXAMPLE 13 | ++ | 94.2 |
| EXAMPLE 14 Isomer 1 | ++ | 97.4 |
| EXAMPLE 14 Isomer 2 | ++ | 111.1 |
| EXAMPLE 15 Isomer 1 | ++ | 86.2 |
| EXAMPLE 15 Isomer 2 | # | 31.7 |
| EXAMPLE 16 Isomer 1 | ++ | 89.9 |
| EXAMPLE 16 Isomer 2 | ++ | 96.1 |
| EXAMPLE 17 Isomer 1 | # | 41.6 |
| EXAMPLE 17 Isomer 2 | ++ | 68.5 |
| EXAMPLE 18 | ++ | 86.8 |
| EXAMPLE 19 | ++ | 80.3 |
| EXAMPLE 20 | ++ | 97.4 |

The compounds of the invention are useful for ameliorating or treating disorders or diseases in which decreasing the level of cortisol is effective in treating a disease state. Thus, the compounds of the invention can be used in the treatment or prevention of diabetes mellitus, obesity (especially abdominal obesity), symptoms of metabolic syndrome, prothrombotic state, proinflammatory state, glucose intolerance, hyperglycemia, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypertriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

The disclosed compounds can be used alone (i.e. as a monotherapy) or in combination with another therapeutic agent effective for treating any of the above indications. The pharmaceutical compositions can comprise the disclosed compounds alone as the only pharmaceutically active agent or can comprise one or more additional pharmaceutically active agents. The disclosed 11β-HSD1 inhibitors can be used alone or in a combination therapy with one or more additional agents for the treatment of diabetes, dyslipidemia, cardiovascular disease, hypertension, obesity, cancer or glaucoma.

A pharmaceutical composition of the invention may, alternatively or in addition to a compound of Formula I, Ia, Ib, Ic, Id, Ie, If, Ig, Il$^{1-3}$, Im$^{1-3}$, In$^{1-3}$, or Io$^{1-2}$ comprise a pharmaceutically acceptable salt of a compound of Formula I, Ia, Ib, Ic, Id, Ie, If, Ig, Il$^{1-3}$, Im$^{1-3}$, In$^{1-3}$, or Io$^{1-2}$ or a prodrug or pharmaceutically active metabolite of such a compound or salt and one or more pharmaceutically acceptable carriers therefore. Alternatively, a pharmaceutical composition of the invention may comprise a compound of Formula I, Ia, Ib, Ic, Id, Ie, If, Ig, Il$^{1-3}$, Im$^{1-3}$, In$^{1-3}$, or Io$^{1-2}$ or a pharmaceutical salt thereof as the only pharmaceutically active agent in the pharmaceutical composition.

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefore. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of a compound of Formula I, or an enantiomer, diastereomer, or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of Formula I or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitazone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL®D and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors such as Januvia® (sitagliptin, Merck) and Galvus® (vildagliptin, Novartis); PTB-1B inhibitors; protein kinase inhibitors (including AMP-activated protein kinase inhibitors); glucagon antagonists, glycogen synthase kinase-3 beta inhibitors; glucose-6-phosphatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium carboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound of Formula (I)

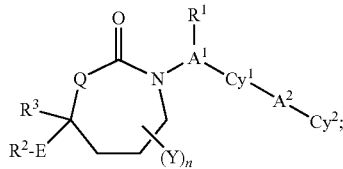

wherein
- $R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy or $(C_1-C_3)$alkoxy$(C_1-C_3)$alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;
- $A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;
- $Cy^1$ is aryl, heteroaryl, monocyclic cycloalkyl or monocyclic heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;
- $A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;
- $Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino ($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

Y is ($C_1$-$C_6$)alkyl or halo($C_1$-$C_6$)alkyl;

n is 0, 1 or 2;

E is (a) a bond or (b) ($C_1$-$C_3$)alkylene or ($C_1$-$C_2$)alkylenyloxy, wherein the O is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, and ($C_1$-$C_3$)alkoxy($C_1$-$C_3$)alkyl, wherein each is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$, $(R^4)_2NS(=O)_2O$, $(R^4)_2NS(=O)_2NR^4$, $R^4S(=O)_2\ NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, spirocycloalkyl; heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

Q is O or $NR^5$;

$R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

$R^5$ is H, ($C_1$-$C_6$)alkyl, halo($C_1$-$C_6$)alkyl, or hydroxy($C_1$-$C_6$)alkyl;

or a pharmaceutically acceptable salt, enantiomer or diastereomer thereof.

2. The compound of claim 1, wherein $R^1$ is (a) absent or (b) is selected from ($C_1$-$C_6$)alkyl, ($C_2$-$C_6$)alkenyl, ($C_2$-$C_6$)alkynyl or ($C_1$-$C_3$)alkoxy($C_1$-$C_3$)alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2\ NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

$R^3$ is selected from ($C_1$-$C_6$)alkyl, ($C_2$-$C_6$)alkenyl, ($C_2$-$C_6$) alkynyl and ($C_1$-$C_3$)alkoxy($C_1$-$C_3$)alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$, $(R^4)_2NS(=O)_2O$, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

Q is O or $NR^5$;

$R^4$ is independently selected from H, ($C_1$-$C_6$)alkyl, halo ($C_1$-$C_6$)alkyl, amino($C_1$-$C_6$)alkyl, ($C_1$-$C_6$)alkylamino ($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

$R^5$ is H, ($C_1$-$C_6$)alkyl, halo($C_1$-$C_6$)alkyl, or hydroxy($C_1$-$C_6$)alkyl;

or a pharmaceutically acceptable salt, enantiomer or diastereomer thereof.

3. The compound of claim 2, wherein the compound is of Formula (I*)

wherein $R^1$ is ($C_1$-$C_6$)alkyl, optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2 NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$Cy^2$ is aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$) alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$) cycloalkoxy, ($C_4$-$C_7$)cycloalkylalkoxy, halo($C_1$-$C_6$) alkoxy, halo($C_3$-$C_6$)cycloalkoxy, halo($C_4$-$C_7$) cycloalkylalkoxy, ($C_1$-$C_6$)alkylthio, ($C_3$-$C_6$) cycloalkylhio, ($C_4$-$C_7$)cycloalkylalkylthio, halo($C_1$-$C_6$) alkylthio, halo($C_3$-$C_6$)cycloalkylhio, halo($C_4$-$C_7$) cycloalkylalkylthio, ($C_1$-$C_6$)alkanesulfinyl, ($C_3$-$C_6$) cycloalkanesulfinyl, ($C_4$-$C_7$)cycloalkylalkanesulfinyl, halo($C_1$-$C_6$)alkane-sulfinyl, halo($C_3$-$C_6$)cycloalkane-sulfinyl, halo($C_4$-$C_7$)cycloalkylalkanesulfinyl, ($C_1$-$C_6$) alkanesulfonyl, ($C_3$-$C_6$)cycloalkanesulfonyl, ($C_4$-$C_7$) cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

X is independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$) cycloalkoxy, ($C_4$-$C_7$)cycloalkylalkoxy, halo($C_1$-$C_6$) alkoxy, halo($C_3$-$C_6$)cycloalkoxy, halo($C_4$-$C_7$)

cycloalkylalkoxy, (C₁-C₆)alkylthio, (C₃-C₆)cycloalkylhio, (C₄-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkyl-alkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl;

m is 0, 1, 2, 3, 4;

R³ is (C₁-C₆)alkyl substituted with up to four groups independently selected from cyano, oxo, HO—, (R⁴)₂N—, R⁴O₂C—, R⁴S, R⁴S(═O)—, R⁴S(═O)₂—, R⁴C(═O)NR⁴, (R⁴)₂NC(═O)—, (R⁴)₂NC(═O)O—, (R⁴)₂NC(═O)NR⁴—, R⁴OC(═O)NR⁴—, (R⁴)₂NC(═NCN)NR⁴, (R⁴O)₂P(═O)O—, (R⁴O)₂P(═O)NR⁴—, R⁴OS(═O)₂NR⁴—, (R⁴)₂NS(═O)₂O—, (R⁴)₂NS(═O)₂NR⁴, R⁴S(═O)₂NR⁴—, R⁴S(═O)₂NHC(═O)—, R⁴S(═O)₂NHC(═O)O—, R⁴S(═O)₂NHC(═O)NR⁴, R⁴OS(═O)₂NHC(═O)—, R⁴OS(═O)₂NHC(═O)O—, R⁴OS(═O)₂NHC(═O)NR⁴, (R⁴)₂NS(═O)₂NHC(═O)—, (R⁴)₂NS(═O)₂NHC(═O)O—, (R⁴)₂NS(═O)₂NHC(═O)NR⁴, R⁴C(═O)NHS(═O)₂—, R⁴C(═O)NHS(═O)₂O—, R⁴C(═O)NHS(═O)₂NR⁴, R⁴OC(═O)NHS(═O)₂—, R⁴OC(═O)NHS(═O)₂O—, R⁴OC(═O)NHS(═O)₂NR⁴, (R⁴)₂NC(═O)NHS(═O)₂—, (R⁴)₂NC(═O)NHS(═O)₂O—, (R⁴)₂NC(═O)NHS(═O)₂NR⁴, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, CO₂H, CONH₂, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, CO₂H, CONH₂, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, CO₂H, CONH₂, N-monoalkyl-substituted amido, N,N-dialkyl-substituted amido, or oxo;

or a pharmaceutically acceptable salt, enantiomer or diastereomer thereof.

4. The compound of claim 2, wherein the compound is of Formula (I**)

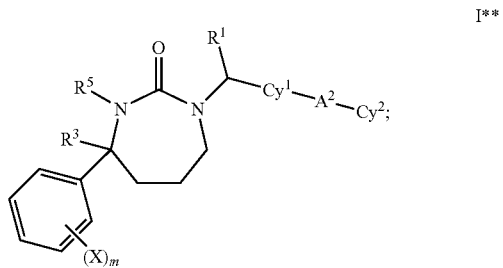

wherein

R¹ is (C₁-C₆)alkyl, optionally substituted with up to four groups independently selected from fluorine, cyano, oxo, R⁴, R⁴O—, (R⁴)₂N—, R⁴O₂C—, R⁴S, R⁴S(═O)—, R⁴S(═O)₂—, R⁴C(═O)NR⁴—, (R⁴)₂NC(═O)—, (R⁴)₂NC(═O)O—, (R⁴)₂NC(═O)NR⁴—, R⁴OC(═O)NR⁴—, (R⁴)₂NC(═NCN)NR⁴—, (R⁴O)₂P(═O)O—, (R⁴O)₂P(═O)NR⁴—, R⁴OS(═O)₂NR⁴—, (R⁴)₂NS(═O)₂O—, (R⁴)₂NS(═O)₂NR⁴—, R⁴S(═O)₂ NR⁴—, R⁴S(═O)₂NHC(═O)—, R⁴S(═O)₂ NHC(═O)O—, R⁴S(═O)₂NHC(═O)NR⁴—, R⁴OS(═O)₂NHC(═O)—, R⁴OS(═O)₂NHC(═O)O—, R⁴OS(═O)₂NHC(═O)NR⁴—, (R⁴)₂NS(═O)₂NHC(═O)—, (R⁴)₂NS(═O)₂NHC(═O)O—, (R⁴)₂NS(═O)₂NHC(═O)NR⁴—, R⁴C(═O)NHS(═O)₂—, R⁴C(═O)NHS(═O)₂O—, R⁴C(═O)NHS(═O)₂NR⁴—, R⁴OC(═O)NHS(═O)₂—, R⁴OC(═O)NHS(═O)₂O—, R⁴OC(═O)NHS(═O)₂NR⁴—, (R⁴)₂NC(═O)NHS(═O)₂—, (R⁴)₂NC(═O)NHS(═O)₂O—, (R⁴)₂NC(═O)NHS(═O)₂NR⁴—, aryl, cycloalkyl, heterocyclyl, heteroaryl, arylamino and heteroarylamino;

Cy¹ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₄-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-

$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

$A^2$ is a bond;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_1$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

X is independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

$R^3$ is ($C_1$-$C_6$)alkyl substituted with up to four groups independently selected from cyano, oxo, $R^4$, HO—, $(R^4)_2$N—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

or a pharmaceutically acceptable salt, enantiomer or diastereomer thereof.

5. The compound of claim 2, wherein $A^1$ is CH and $R^1$ is present.

6. The compound of claim 5, wherein $R^1$ is unsubstituted methyl or ethyl.

7. The compound of claim 2, wherein $Cy^1$ is optionally substituted phenyl.

8. The compound of claim 2, wherein $R^3$ is hydroxy($C_2$-$C_4$)alkyl.

9. The compound of claim 2, wherein $R^3$ is allyl.

10. The compound of claim 2, wherein $R^2$ is optionally substituted phenyl.

11. The compound of claim 2, wherein E is a bond.

12. The compound of claim 2, wherein $R^2$ is fluorophenyl.

13. The compound of claim 2, wherein $R^1$ is absent or is methyl or ethyl;

$A^1$ is a bond or $CH_2$ or if $R^1$ is present, then $A^1$ is CH;

$Cy^1$ is phenyl, cyclopropyl, cyclohexyl, pyrrolidinyl, pyridyl, N-oxo-pyridyl, thiazolyl or pyrimidinyl each optionally substituted with 1 to 4 groups independently selected from halo, methyl, trifluoromethyl, hydroxy, methoxy, methoxycarbonyl, carboxy, ethoxycarbonylmethoxy 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;

$A^2$ is a bond, O, $OCH_2CO$ or C=O;

$Cy^2$ is (a) hydrogen or (b) phenyl, thienyl, pyridyl, N-oxopyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl each optionally substituted by 1 to 4 groups independently selected from aminomethyl, 1-aminoethyl, halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

n is 0;

E is a bond or $CH_2$;

$R^2$ is cyclohexyl, isopropyl, thienyl, phenyl or pyridyl, each optionally substituted with one group selected from halo, methyl, methylthio or (4-morpholino)methyl;

$R^3$ is methyl, ethyl, propyl, butyl, vinyl, allyl or ethoxyethyl, each optionally substituted with up to two groups independently selected from methyl, $H_2C=CH$, HO—, MeO—, MeC(=O), $H_2N$—, MeC(=O)NH—, MeS(=O)$_2$NH—, $H_2NC$(=O)—, MeNHC(=O)—, $HO_2C$—, HO—$(CH_2)_2$O—, $(HO)_2P$(=O)O—, $H_2NS$(=O)$_2$O—, $H_2NS$(=O)$_2$NH—, MeNHC(=O)NH—, MeNHC(=O)O—, cyano, $HO_2C$—, $HOCH_2CH_2NH$—, 4-morpholino, $HOCH_2C$(=O)NH—, $H_2NCH_2C$(=O)NH—, EtNHC(=O)NH, $H_2NHC$(=O)NH, $H_2NHC$(=O)O—, $CH_3C$(=O)—, MeOC(=O)NH—, MeNHC(=NC≡N)NH—, Me-, MeS-, $MeSO_2$— $MeSO_2N$(Me)—, $MeS$(=O)$_2NHC$(=O)—, imidazolylamino-, imidazolyl, morpholino, tetrazolyl, $H_2NCONH$—, $H_2NCO_2$—, $HOCH_2CH_2O$—, MeNH—, $Me_2N$— and MeCONMe; and $R^5$ is hydrogen or methyl.

14. The compound of claim 2, wherein the compound is of Formula (Ia)

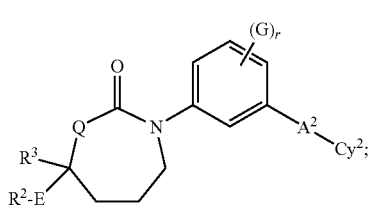

wherein r is 0, 1, 2, 3 or 4; and

G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl or $(C_1-C_6)$alkylcarbonyl;

or a pharmaceutically acceptable salt, enantiomer or diastereomer thereof.

15. The compound of claim 2, wherein the compound is of Formula (Ib)

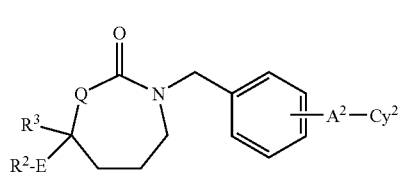

or a pharmaceutically acceptable salt, enantiomer or diastereomer thereof.

16. The compound of claim 2, wherein the compound is of Formula (Ic)

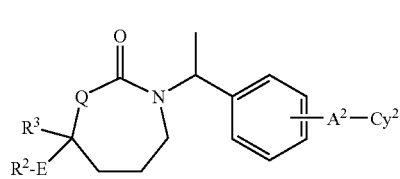

or a pharmaceutically acceptable salt, enantiomer or diastereomer thereof.

17. The compound of claim 2, wherein the compound is of Formula (Id)

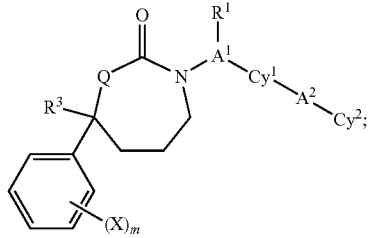

wherein
m is 0, 1, 2, 3 or 4;
X is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;
or a pharmaceutically acceptable salt, enantiomer or diastereomer thereof.

18. The compound of claim 2, wherein the compound is of Formula (Ie)

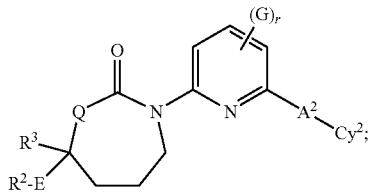

wherein
r is 0, 1, 2, 3 or 4;
G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;
or a pharmaceutically acceptable salt, enantiomer or diastereomer thereof.

19. The compound of claim 2, wherein the compound is of Formula (If)

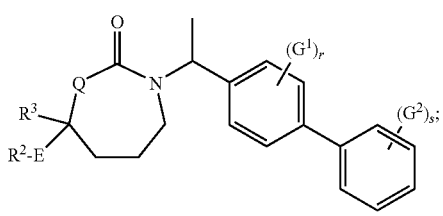

wherein
r and s are independently 0, 1, 2, 3 or 4; and
$G^1$ and $G^2$ are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$ cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkyl-aminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

or a pharmaceutically acceptable salt, enantiomer or diastereomer thereof.

20. The compound of claim 2, wherein the compound is of Formula (Ig)

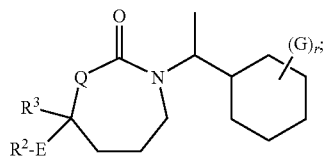

Ig wherein r is 0, 1, 2, 3 or 4; and

G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_1-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkyl-aminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_1-C_6)$alkoxyl and $(C_1-C_6)$alkylcarbonyl;

or a pharmaceutically acceptable salt, enantiomer or diastereomer thereof.

21. The compound of claim 2, wherein the compound is represented one of the following structural formulas:

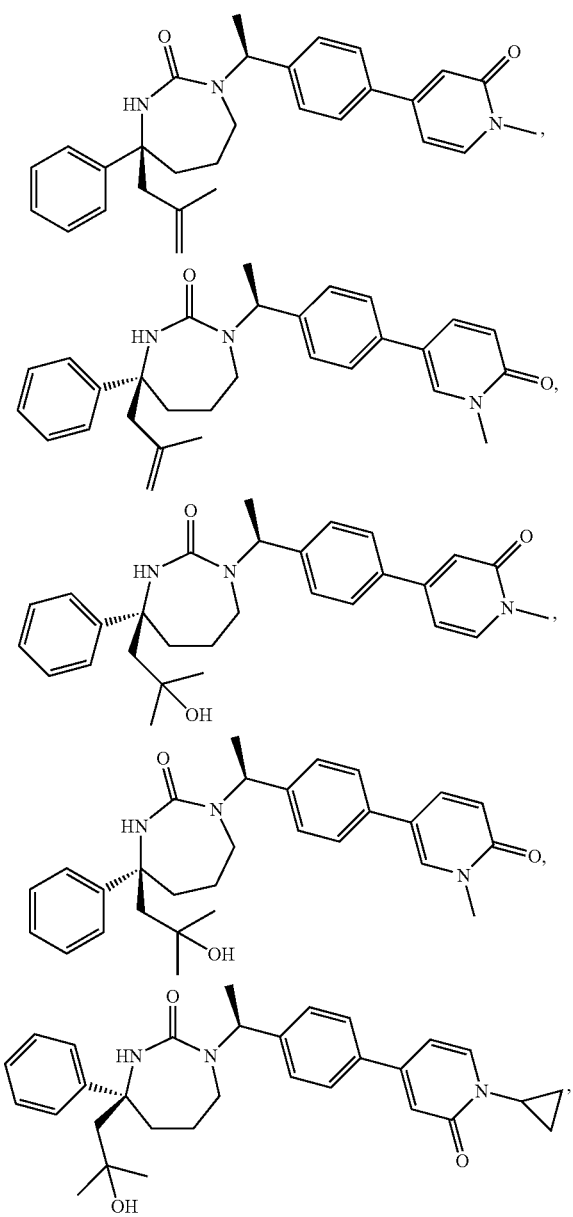

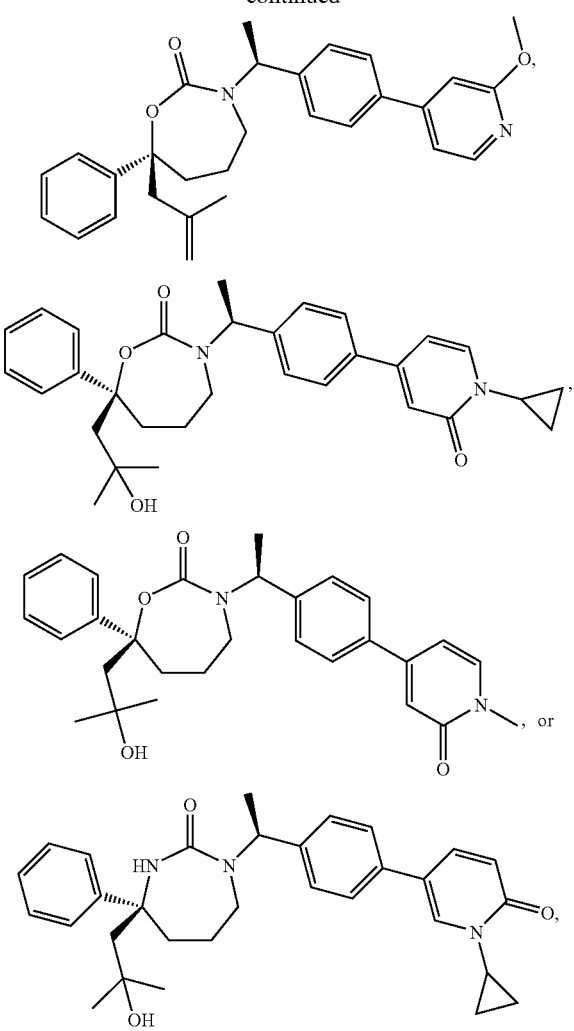

or a pharmaceutically acceptable salt, enantiomer or diastereomer thereof.

22. The compound of claim 1, wherein the compound is represented by a structural formula selected from:

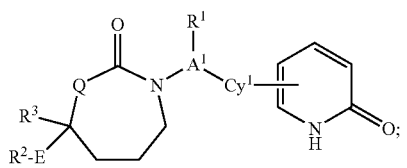

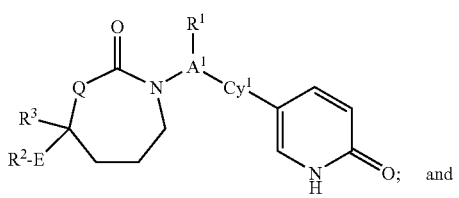

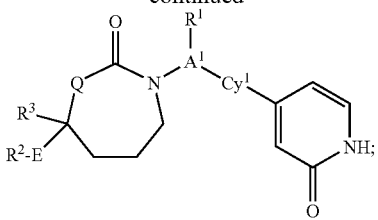

or a pharmaceutically acceptable salt, enantiomer or diastereomer thereof, wherein the oxodihydropyridyl group is optionally substituted with up to four substitutents selected from fluorine, chlorine, bromine, iodine, cyano, nitro, amino, hydroxy, carboxy, $(C_1-C_6)$alkyl, hydroxy $(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl.

23. The compound of claim 22, wherein the compound is represented by a structural formula selected from:

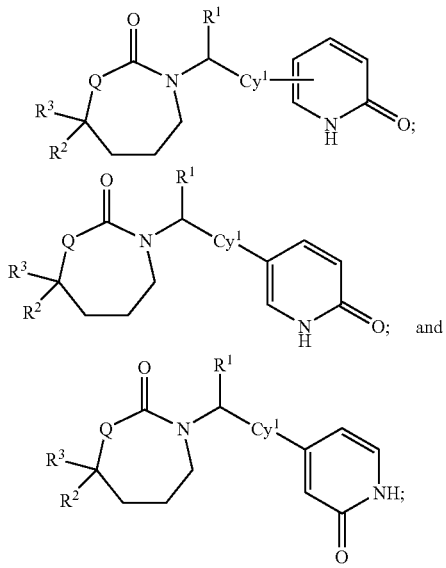

or a pharmaceutically acceptable salt, enantiomer or diastereomer thereof, wherein the oxodihydropyridyl group is optionally substituted with up to four substitutents selected from fluorine, chlorine, bromine, iodine, cyano, nitro, amino, hydroxy, carboxy, $(C_1-C_6)$alkyl, hydroxy $(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo $(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy $(C_1-C_6)$alkyl, halo$(C_1-C_6)$alkoxy$(C_1-C_6)$alkyl, hydroxy $(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino $(C_1-C_6)$alkyl, amino$(C_2-C_6)$alkoxy, $(C_1-C_6)$alkylamino $(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl.

24. The compound of claim 22, wherein the compound is represented by a structural formula selected from:

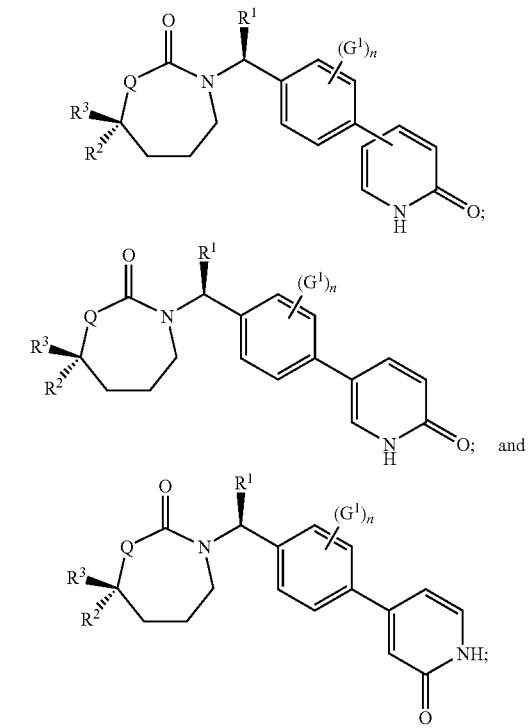

or a pharmaceutically acceptable salt, enantiomer or diastereomer thereof, wherein:

n is 0, 1, 2, or 3;

each $G^1$ is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkyl-aminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl; and the oxodihydropyridyl group is optionally substituted with up to four substituents selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkane-sulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl.

25. The compound of claim 1, wherein the compound is represented by a structural formula selected from:

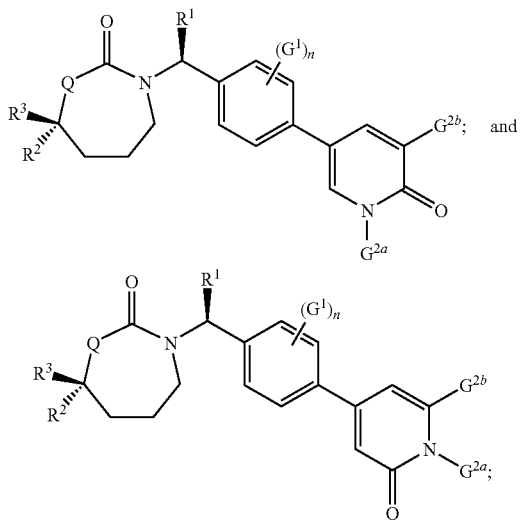

or a pharmaceutically acceptable salt thereof, wherein: $G^1$ is $(C_1-C_4)$alkyl, $(C_1-C_4)$alkoxy, $(C_1-C_4)$haloalkyl, $(C_1-C_4)$haloalkoxy, halogen, cyano or nitro; n is 0, 1 or 2; $G^{2a}$ is $(C_1-C_4)$alkyl, $(C_3-C_4)$cycloalkyl or $(C_1-C_4)$haloalkyl; $G^{2b}$ is hydrogen, fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino; Q is O or NH; $R^1$ is methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

26. A method of treating a subject with a disease selected from diabetes mellitus, obesity, glucose intolerance, hyperglycemia, hyperlipidemia, insulin resistance, hypertriglyceridemia and hyperinsulinemia; comprising the step of administering to the subject an effective amount of a compound of Formula (I)

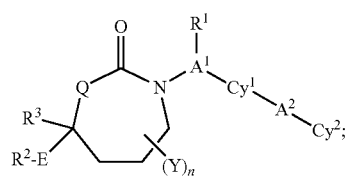

wherein $R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy or $(C_1-C_3)$alkoxy$(C_1-C_3)$alkyl, wherein each is optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)$ O—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkane-sulfinyl, halo($C_4$-$C_7$)cycloalkylalkanesulfinyl, ($C_1$-$C_6$) alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{ ($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$) cycloalkyl}{($C_1$-$C_6$)alkyl}aminosulfonyl, di($C_3$-$C_6$) cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$) alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_1$-$C_6$)alkyl, ($C_2$-$C_6$)alkenyl, ($C_2$-$C_6$) alkynyl, ($C_3$-$C_5$)cycloalkyl($C_1$-$C_4$)alkyl, ($C_1$-$C_3$)alkoxy ($C_1$-$C_3$)alkoxy, and ($C_1$-$C_3$)alkoxy($C_1$-$C_3$)alkyl, wherein each is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$, $(R^4)_2NS(=O)_2O$, $(R^4)_2NS(=O)_2NR^4$, $R^4S(=O)_2$ $NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $(R^4)_2NC(=O)NHS(=O)_2$—, $(R^4)_2NC(=O)NHS(=O)_2O$—, $(R^4)_2$ $NC(=O)NHS(=O)_2NR^4$, spirocycloalkyl; heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

Q is O or $NR^5$;

$R^4$ is independently selected from H, ($C_1$-$C_6$)alkyl, halo ($C_1$-$C_6$)alkyl, amino($C_1$-$C_6$)alkyl, ($C_1$-$C_6$)alkylamino ($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

$R^5$ is H, ($C_1$-$C_6$)alkyl, halo($C_1$-$C_6$)alkyl, or hydroxy($C_1$-$C_6$)alkyl;

or a pharmaceutically acceptable salt, enantiomer or diastereomer thereof.

27. The method of claim 26, wherein $R^1$ is (a) absent or (b) is selected from ($C_1$-$C_6$)alkyl, ($C_2$-$C_6$)alkenyl, ($C_2$-$C_6$)alkynyl or ($C_1$-$C_3$)alkoxy($C_1$-$C_3$) alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2$ $NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$A^1$ is (a) a bond, or (b) ($C_1$-$C_3$)alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$) cycloalkoxy, ($C_4$-$C_7$)cycloalkylalkoxy, halo($C_1$-$C_6$) alkoxy, halo($C_3$-$C_6$)cycloalkoxy, halo($C_4$-$C_7$) cycloalkylalkoxy, ($C_1$-$C_6$)alkylthio, ($C_3$-$C_6$) cycloalkylhio, ($C_4$-$C_7$)cycloalkylalkylthio, halo($C_1$-$C_6$) alkylthio, halo($C_3$-$C_6$)cycloalkylhio, halo($C_4$-$C_7$)

cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_1-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$allyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$R^3$ is selected from $(C_1-C_6)$alkyl, $(C_2-C_6)$alkenyl, $(C_2-C_6)$alkynyl and $(C_1-C_3)$alkoxy$(C_1-C_3)$alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4$, $(R^4O)_2P(=O)O-$, $(R^4O)_2P(=O)NR^4-$, $R^4OS(=O)_2NR^4$, $(R^4)_2NS(=O)_2O$, $(R^4)_2NS(=O)_2NR^4$, $R^4S(=O)_2NR^4-$, $R^4S(=O)_2NHC(=O)-$, $R^4S(=O)_2NHC(=O)O-$, $R^4S(=O)_2NHC(=O)NR^4$, $R^4OS(=O)_2NHC(=O)-$, $R^4OS(=O)_2NHC(=O)O-$, $R^4OS(=O)_2NHC(=O)NR^4$, $(R^4)_2NS(=O)_2NHC(=O)-$, $(R^4)_2NS(=O)_2NHC(=O)O-$, $(R^4)_2NS(=O)_2NHC(=O)NR^4$, $R^4C(=O)NHS(=O)_2-$, $R^4C(=O)NHS(=O)_2O-$, $R^4C(=O)NHS(=O)_2NR^4$, $R^4OC(=O)NHS(=O)_2-$, $R^4OC(=O)NHS(=O)_2O-$, $R^4OC(=O)NHS(=O)_2NR^4$, $(R^4)_2NC(=O)NHS(=O)_2-$, $(R^4)_2NC(=O)NHS(=O)_2O-$, $(R^4)_2NC(=O)NHS(=O)_2NR^4$, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

Q is O or $NR^5$;

$R^4$ is independently selected from H, $(C_1-C_6)$alkyl, halo $(C_1-C_6)$alkyl, amino$(C_1-C_6)$alkyl, $(C_1-C_6)$alkylamino $(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

$R^5$ is H, $(C_1-C_6)$alkyl, halo$(C_1-C_6)$alkyl, or hydroxy$(C_1-C_6)$alkyl;

or a pharmaceutically acceptable salt, enantiomer or diastereomer thereof.

28. The method of claim 27, wherein the compound is of Formula (I*)

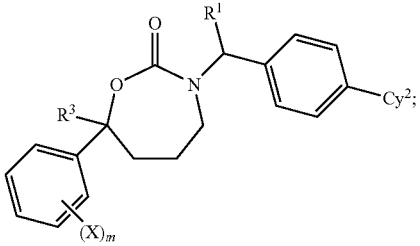

I* wherein $R^1$ is $(C_1-C_6)$alkyl, optionally substituted with up to four groups independently selected, from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2 NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O, R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;

$Cy^2$ is aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

X is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

m is 0, 1, 2, 3, 4;

$R^3$ is ($C_1$-$C_6$)alkyl substituted with up to four groups independently selected from cyano, oxo, HO—, $(R^4)_2$N—, $R^4O_2$C—, $R^4$S, $R^4$S(=O)—, $R^4$S(=O)$_2$—, $R^4$C(=O)NR$^4$, $(R^4)_2$NC(=O)—, $(R^4)_2$NC(=O)O—, $(R^4)_2$NC(=O)NR$^4$—, $R^4$OC(=O)NR$^4$—, $(R^4)_2$NC(=NCN)NR$^4$, $(R^4O)_2$P(=O)O—, $(R^4O)_2$P(=O)NR$^4$—, $R^4$OS(=O)$_2$NR$^4$—, $(R^4)_2$NS(=O)$_2$O—, $(R^4)_2$NS(=O)$_2$NR$^4$, $R^4$S(=O)$_2$NR$^4$—, $R^4$S(=O)$_2$NHC(=O)—, $R^4$S(=O)$_2$NHC(=O)O—, $R^4$S(=O)$_2$NHC(=O)NR$^4$, $R^4$OS(=O)$_2$NHC(=O)—, $R^4$OS(=O)$_2$NHC(=O)O—, $R^4$OS(=O)$_2$NHC(=O)NR$^4$, $(R^4)_2$NS(=O)$_2$NHC(=O)—, $(R^4)_2$NS(=O)$_2$NHC(=O)O—, $(R^4)_2$NS(=O)$_2$NHC(=O)NR$^4$, $R^4$C(=O)NHS(=O)$_2$—, $R^4$C(=O)NHS(=O)$_2$O—, $R^4$C(=O)NHS(=O)$_2$NR$^4$, $R^4$OC(=O)NHS(=O)$_2$—, $R^4$OC(=O)NHS(=O)$_2$O—, $R^4$OC(=O)NHS(=O)$_2$NR$^4$, $(R^4)_2$NC(=O)NHS(=O)$_2$—, $(R^4)_2$NC(=O)NHS(=O)$_2$O—, $(R^4)_2$NC(=O)NHS(=O)$_2$NR$^4$, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2$H, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo;

or a pharmaceutically acceptable salt, enantiomer or diastereomer thereof.

29. The method of claim 27, wherein the compound is of Formula (I**)

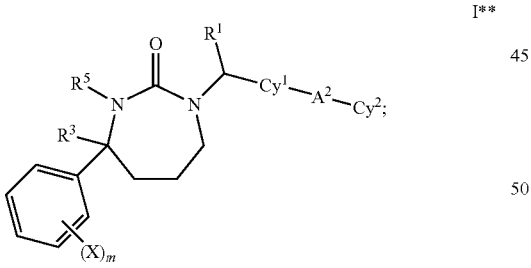

I** wherein $R^1$ is ($C_1$-$C_6$)alkyl, optionally substituted with up to four groups independently selected from fluorine, cyano, oxo, $R^4$, $R^4$O—, $(R^4)_2$N—, $R^4O_2$C—, $R^4$S, $R^4$S(=O)—, $R^4$S(=O)$_2$—, $R^4$C(=O)NR$^4$—, $(R^4)_2$NC(=O)—, $(R^4)_2$NC(=O)O—, $(R^4)_2$NC(=O)NR$^4$—, $R^4$OC(=O)NR$^4$—, $(R^4)_2$NC(=NCN)NR$^4$—, $(R^4O)_2$P(=O)O—, $(R^4O)_2$P(=O)NR$^4$—, $R^4$OS(=O)$_2$NR$^4$—, $(R^4)_2$NS(=O)$_2$O—, $(R^4)_2$NS(=O)$_2$NR$^4$—, $R^4$S(=O)$_2$NR$^4$—, $R^4$S(=O)$_2$NHC(=O)—, $R^4$S(=O)$_2$NHC(=O)O—, $R^4$S(=O)$_2$NHC(=O)NR$^4$—, $R^4$OS(=O)$_2$NHC(=O)—, $R^4$OS(=O)$_2$NHC(=O)O—, $R^4$OS(=O)$_2$NHC(=O)NR$^4$—, $(R^4)_2$NS(=O)$_2$NHC(=O)—, $(R^4)_2$NS(=O)$_2$NHC(=O)O—, $(R^4)_2$NS(=O)$_2$NHC(=O)NR$^4$—, $R^4$C(=O)NHS(=O)$_2$—, $R^4$C(=O)NHS(=O)$_2$O—, $R^4$C(=O)NHS(=O)$_2$NR$^4$—, $R^4$OC(=O)NHS(=O)$_2$—, $R^4$OC(=O)NHS(=O)$_2$O—, $R^4$OC(=O)NHS(=O)$_2$NR$^4$—, $(R^4)_2$NC(=O)NHS(=O)$_2$—, $(R^4)_2$NC(=O)NHS(=O)$_2$O—, $(R^4)_2$NC(=O)NHS(=O)$_2$NR$^4$—, aryl, cycloalkyl, heterocyclyl, heteroaryl, arylamino and heteroarylamino;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$NSO$_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

$A^2$ is a bond;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_1$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo ($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

X is independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$) cycloalkoxy, ($C_4$-7)cycloalkylalkoxy, halo($C_1$-$C_6$) alkoxy, halo($C_3$-$C_6$)cycloalkoxy, halo($C_4$-$C_7$) cycloalkylalkoxy, ($C_1$-$C_6$)alkylthio, ($C_3$-$C_6$) cycloalkylalkoxy, ($C_4$-$C_7$)cycloalkylalkylthio, halo($C_1$-$C_6$) alkylthio, halo($C_3$-$C_6$)cycloalkylhio, halo($C_4$-$C_7$) cycloalkylalkylthio, ($C_1$-$C_6$)alkanesulfinyl, ($C_3$-$C_6$) cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

m is 0, 1, 2, 3, 4; and $R^3$ is ($C_1$-$C_6$)alkyl substituted with up to four groups independently selected from cyano, oxo, $R^4$, HO—, $(R^4)_2$N—, $R^4O_2C$—, $R^4S$, $R^4S(=O)$—, $R^4C(=O)NR^4$, $(R^4)_2$ NC(=O)—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2$NR$^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2$NHC(=O)O—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC$ (=O)—, $(R^4)_2NS(=O)_2NHC(=O)O$—, $(R^4)_2NS$ (=O)$_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2$O—, $R^4OC(=O)NHS(=O)_2NR^4$, $(R^4)_2NC(=O)NHS$ (=O)$_2$—, $(R^4)_2NC(=O)NHS(=O)_2O$—, $(R^4)_2NC (=O)NHS(=O)_2NR^4$, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

or a pharmaceutically acceptable salt, enantiomer or diastereomer thereof.

30. The method of claim 27, wherein $A^1$ is CH and $R^1$ is present.

31. The method of claim 30, wherein $R^1$ is unsubstituted methyl or ethyl.

32. The method of claim 27, wherein $Cy^1$ is optionally substituted phenyl.

33. The method of claim 27, wherein $R^3$ is hydroxy($C_2$-$C_4$) alkyl.

34. The method of claim 27, wherein $R^3$ is allyl.

35. The method of claim 27, wherein $R^2$ is optionally substituted phenyl.

36. The method of claim 27, wherein E is a bond.

37. The method of claim 27, wherein $R^2$ is fluorophenyl.

38. The method of claim 27, wherein $R^1$ is absent or is methyl or ethyl;

$A^1$ is a bond or $CH_2$ or if $R^1$ is present, then $A^1$ is CH;

$Cy^1$ is phenyl, cyclopropyl, cyclohexyl, pyrrolidinyl, pyridyl, N-oxo-pyridyl, thiazolyl or pyrimidinyl each optionally substituted with 1 to 4 groups independently selected from halo, methyl, trifluoromethyl, hydroxy, methoxy, methoxycarbonyl, carboxy, ethoxycarbonyl-methoxy 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;

$A^2$ is a bond, O, $OCH_2CO$ or C=O;

$Cy^2$ is (a) hydrogen or (b) phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl each optionally substituted by 1 to 4 groups independently selected from aminomethyl, 1-aminoethyl, halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

n is 0;

E is a bond or CH$_2$;

R$^2$ is cyclohexyl, isopropyl, thienyl, phenyl or pyridyl, each optionally substituted with one group selected from halo, methyl, methylthio or (4-morpholino)methyl;

R$^3$ is methyl, ethyl, propyl, butyl, vinyl, allyl or ethoxyethyl, each optionally substituted with up to two groups independently selected from methyl, H$_2$C=CH, HO—, MeO—, MeC(=O), H$_2$N—, MeC(=O)NH—, MeS(=O)$_2$NH—, H$_2$NC(=O)—, MeNHC(=O)—, HO$_2$C—, HO—(CH$_2$)$_2$O—, (HO)$_2$P(=O)O—, H$_2$NS(=O)$_2$O—, H$_2$NS(=O)$_2$NH—, MeNHC(=O)NH—, MeNHC(=O)O—, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, H$_2$NHC(=O)NH, H$_2$NHC(=O)O—, CH$_3$C(=O)—, MeOC(=O)NH—, MeNHC(=NC≡N)NH—, Me-, MeS-, MeSO$_2$— MeSO$_2$N(Me)—, MeS(=O)$_2$NHC(=O)—, imidazolylamino-, imidazolyl, morpholino, tetrazolyl, H$_2$NCONH—, H$_2$NCO$_2$—, HOCH$_2$CH$_2$O—, MeNH—, Me$_2$N— and MeCONMe; and R$^5$ is hydrogen or methyl.

39. The method of claim 27, wherein the compound is of Formula (Ia)

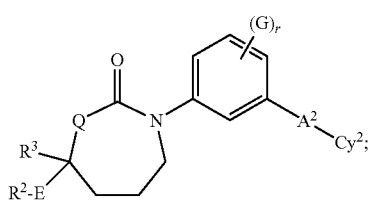

Ia wherein r is 0, 1, 2, 3 or 4; and

G is independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkylhio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkane-sulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocylsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl or (C$_1$-C$_6$)alkylcarbonyl;

or a pharmaceutically acceptable salt, enantiomer or diastereomer thereof.

40. The method of claim 27, wherein the compound is of Formula (Ib)

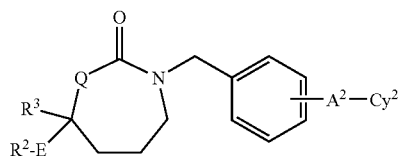

Ib or a pharmaceutically acceptable salt, enantiomer or diastereomer thereof.

41. The method of claim 27, wherein the compound is of Formula (Ic)

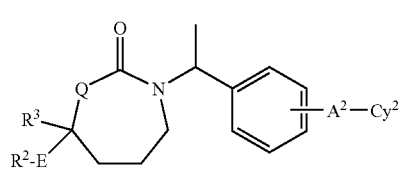

Ic or a pharmaceutically acceptable salt, enantiomer or diastereomer thereof.

42. The method of claim 27, wherein the compound is of Formula (Id)

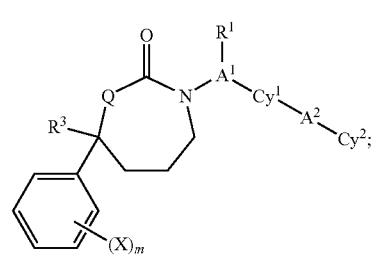

Id wherein m is 0, 1, 2, 3 or 4;

X is independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)

cycloalkylhio, (C₄-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkane-sulfinyl, halo(C₄-C₇)cycloalkylalkanesulfinyl, (C₁-C₆)alkanesulfonyl, (C₃-C₆)cycloalkanesulfonyl, (C₄-C₇)cycloalkyl-alkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkyl, heteroaryl, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl;

or a pharmaceutically acceptable salt, enantiomer or diastereomer thereof.

43. The method of claim 27, wherein the compound is of Formula (Ie)

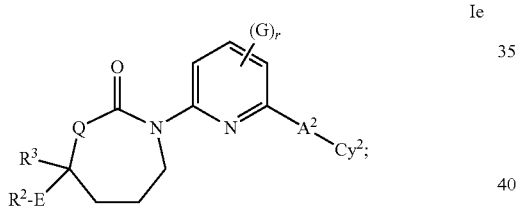

wherein
r is 0, 1, 2, 3 or 4;
G is independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₄-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkane-sulfinyl, halo(C₄-C₇)cycloalkylalkanesulfinyl, (C₁-C₆)alkanesulfonyl, (C₃-C₆)cycloalkanesulfonyl, (C₄-C₇)cycloalkyl-alkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl;

or a pharmaceutically acceptable salt, enantiomer or diastereomer thereof.

44. The method of claim 27, wherein the compound is of Formula (If)

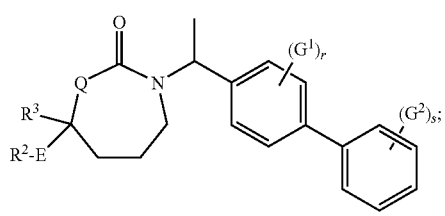

wherein
r and s are independently 0, 1, 2, 3 or 4; and
G¹ and G² are independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₄-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkanesulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkyl-alkanesulfonyl, halo(C₁-C₆)alkanesulfonyl, halo(C₃-C₆)cycloalkanesulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkyl-aminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, amino(C₁-C₆)alkyl, (C₁-C₆)alkylamino(C₁-C₆)alkyl, di(C₁-C₆)alkylamino(C₁-C₆)

alkyl, amino($C_2$-$C_6$)alkoxy, ($C_1$-$C_6$)alkylamino($C_2$-$C_6$) alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

45. The method of claim 27, wherein the compound is of Formula (Ig)

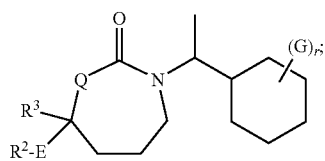

wherein r is 0, 1, 2, 3 or 4; and

G is independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$) cycloalkoxy, ($C_4$-$C_7$)cycloalkylalkoxy, halo($C_1$-$C_6$) alkoxy, halo($C_3$-$C_6$)cycloalkoxy, halo($C_4$-$C_7$) cycloalkylalkoxy, ($C_1$-$C_6$)alkylthio, ($C_3$-$C_6$) cycloalkylhio, ($C_4$-$C_7$)cycloalkylalkylthio, halo($C_1$-$C_6$) alkylthio, halo($C_3$-$C_6$)cycloalkylhio, halo($C_4$-$C_7$) cycloalkylalkylthio, ($C_1$-$C_6$)alkanesulfinyl, ($C_3$-$C_6$) cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$) alkanesulfonyl, ($C_3$-$C_6$)cycloalkanesulfonyl, ($C_4$-$C_7$) cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkyl-aminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, amino($C_1$-$C_6$)alkyl, ($C_1$-$C_6$) alkylamino($C_1$-$C_6$)alkyl, di($C_1$-$C_6$)alkylamino($C_1$-$C_6$) alkyl, amino($C_2$-$C_6$)alkoxy, ($C_1$-$C_6$)alkylamino($C_1$-$C_6$) alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

46. The method of claim 27, wherein the compound is represented one of the following structural formulas:

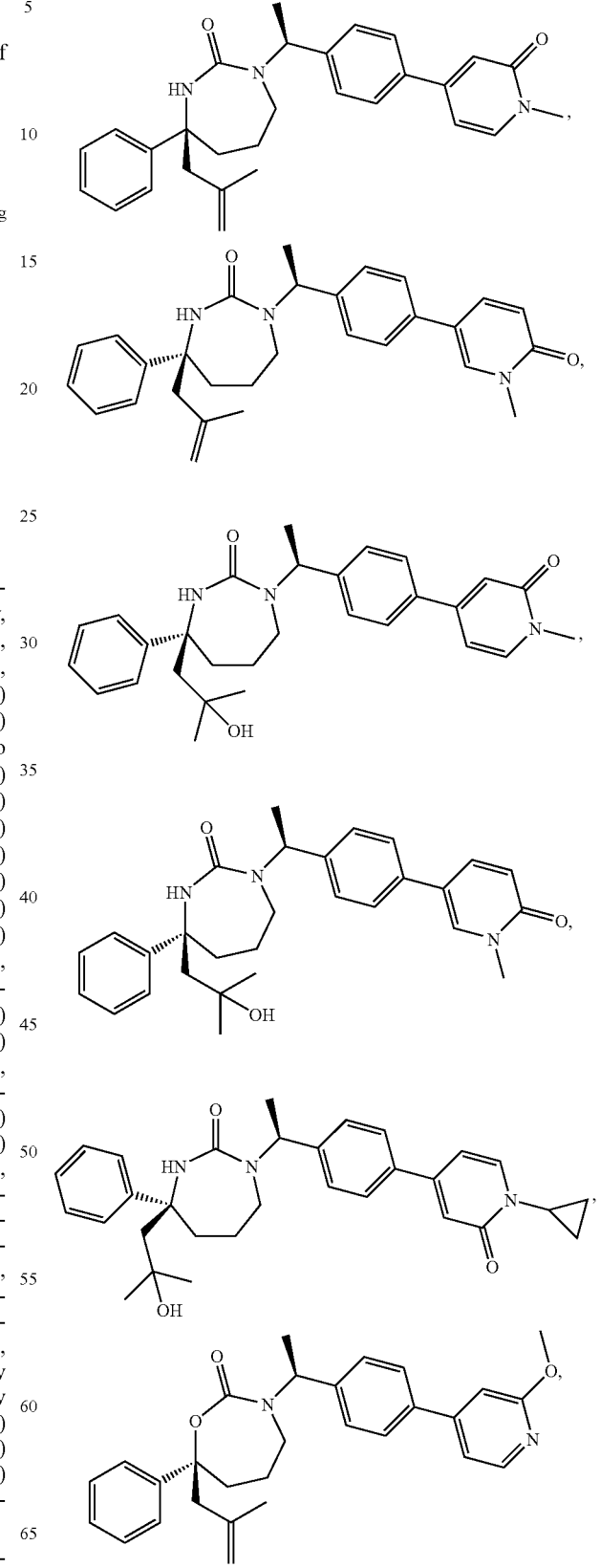

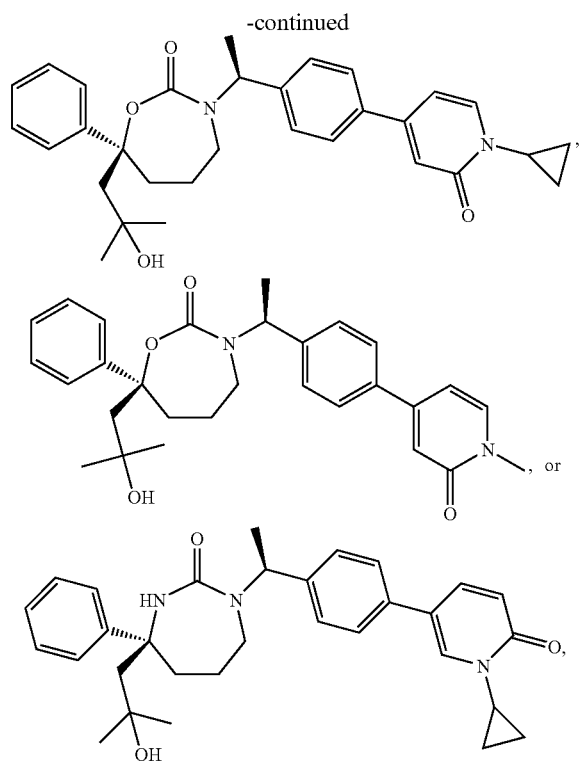

or a pharmaceutically acceptable salt, enantiomer or diastereomer thereof.

47. The method of claim 26, wherein the compound is represented by a structural formula selected from:

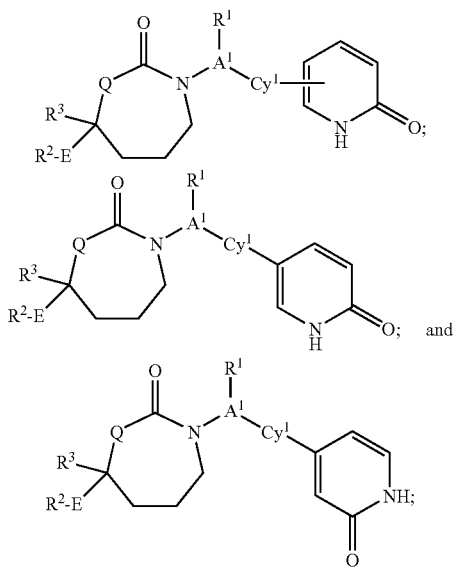

or a pharmaceutically acceptable salt, enantiomer or diastereomer thereof, wherein the oxodihydropyridyl group is optionally substituted with up to four substitutents selected from fluorine, chlorine, bromine, iodine, cyano, nitro, amino, hydroxy, carboxy, $(C_1\text{-}C_6)$alkyl, hydroxy$(C_1\text{-}C_6)$alkyl, $(C_3\text{-}C_6)$cycloalkyl, hydroxy$(C_3\text{-}C_6)$cycloalkyl, $(C_4\text{-}C_7)$cycloalkylalkyl, $(C_2\text{-}C_6)$alkenyl, halo$(C_2\text{-}C_6)$alkenyl, hydroxy$(C_2\text{-}C_6)$alkenyl, $(C_2\text{-}C_6)$alkynyl, $(C_3\text{-}C_6)$cycloalkyl$(C_2\text{-}C_4)$alkynyl, halo$(C_1\text{-}C_6)$alkyl, halo$(C_3\text{-}C_6)$cycloalkyl, halo$(C_4\text{-}C_7)$cycloalkylalkyl, $(C_1\text{-}C_6)$alkoxy, $(C_3\text{-}C_6)$cycloalkoxy, $(C_4\text{-}C_7)$cycloalkylalkoxy, halo$(C_1\text{-}C_6)$alkoxy, halo$(C_3\text{-}C_6)$cycloalkoxy, halo$(C_4\text{-}C_7)$cycloalkylalkoxy, $(C_1\text{-}C_6)$alkylthio, $(C_3\text{-}C_6)$cycloalkylthio, $(C_4\text{-}C_7)$cycloalkylalkylthio, halo$(C_1\text{-}C_6)$alkylthio, halo$(C_3\text{-}C_6)$cycloalkylthio, halo$(C_4\text{-}C_7)$cycloalkylalkylthio, $(C_1\text{-}C_6)$alkanesulfinyl, $(C_3\text{-}C_6)$cycloalkanesulfinyl, $(C_4\text{-}C_7)$cycloalkylalkanesulfinyl, halo$(C_1\text{-}C_6)$alkane-sulfinyl, halo$(C_3\text{-}C_6)$cycloalkanesulfinyl, halo$(C_4\text{-}C_7)$cycloalkylalkanesulfinyl, $(C_1\text{-}C_6)$alkanesulfonyl, $(C_3\text{-}C_6)$cycloalkanesulfonyl, $(C_4\text{-}C_7)$cycloalkylalkanesulfonyl, halo$(C_1\text{-}C_6)$alkanesulfonyl, halo$(C_3\text{-}C_6)$cycloalkanesulfonyl, halo$(C_4\text{-}C_7)$cycloalkylalkanesulfonyl, $(C_1\text{-}C_6)$alkylamino, di$(C_1\text{-}C_6)$alkylamino, $(C_1\text{-}C_6)$alkoxy$(C_1\text{-}C_6)$alkoxy, halo$(C_1\text{-}C_6)$alkoxy$(C_1\text{-}C_6)$alkoxy, $(C_1\text{-}C_6)$alkoxycarbonyl, $H_2NCO$, $H_2NSO_2$, $(C_1\text{-}C_6)$alkylaminocarbonyl, di$(C_1\text{-}C_6)$alkylaminocarbonyl, $(C_1\text{-}C_3)$alkoxy$(C_1\text{-}C_3)$alkylaminocarbonyl, heterocyclylcarbonyl, $(C_1\text{-}C_6)$alkylaminosulfonyl, di$(C_1\text{-}C_6)$alkylaminosulfonyl, heterocyclsulfonyl, $(C_1\text{-}C_6)$alkylcarbonylamino, $(C_1\text{-}C_6)$alkyl-carbonylamino$(C_1\text{-}C_6)$alkyl, $(C_1\text{-}C_6)$alkylsulfonylamino, $(C_1\text{-}C_6)$alkylsulfonylamino$(C_1\text{-}C_6)$alkyl, $(C_1\text{-}C_6)$alkoxycarbonyl$(C_1\text{-}C_6)$alkoxy, $(C_1\text{-}C_6)$alkoxy$(C_1\text{-}C_6)$alkyl, halo$(C_1\text{-}C_6)$alkoxy$(C_1\text{-}C_6)$alkyl, hydroxy$(C_1\text{-}C_6)$alkoxy, heteroaryl, oxo, amino$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$alkyl, amino$(C_2\text{-}C_6)$alkoxy, $(C_1\text{-}C_6)$alkylamino$(C_2\text{-}C_6)$alkoxy, di$(C_1\text{-}C_6)$alkylamino$(C_2\text{-}C_6)$alkoxyl, $(C_1\text{-}C_6)$alkylcarbonyl, $(C_3\text{-}C_6)$cycloalkylcarbonyl, $(C_3\text{-}C_6)$cycloalkylaminocarbonyl, {$(C_3\text{-}C_6)$cycloalkyl}{$(C_1\text{-}C_6)$alkyl}aminocarbonyl, di$(C_3\text{-}C_6)$cycloalkylaminocarbonyl, $(C_3\text{-}C_6)$cycloalkylaminosulfonyl, {$(C_3\text{-}C_6)$cycloalkyl}{$(C_1\text{-}C_6)$alkyl}aminosulfonyl, di$(C_3\text{-}C_6)$cycloalkylaminosulfonyl, cyano$(C_1\text{-}C_6)$alkyl, aminocarbonyl$(C_1\text{-}C_6)$alkyl, $(C_1\text{-}C_6)$alkylaminocarbonyl$(C_1\text{-}C_6)$alkyl, di$(C_1\text{-}C_6)$alkylaminocarbonyl$(C_1\text{-}C_6)$alkyl, $(C_3\text{-}C_6)$cycloalkylaminocarbonyl$(C_1\text{-}C_6)$alkyl, {$(C_3\text{-}C_6)$cycloalkyl}{$(C_1\text{-}C_6)$alkyl}aminocarbonyl$(C_1\text{-}C_6)$alkyl and di$(C_3\text{-}C_6)$cycloalkylaminocarbonyl$(C_1\text{-}C_6)$alkyl.

48. The method of claim 47, wherein the compound is represented by a structural formula selected from:

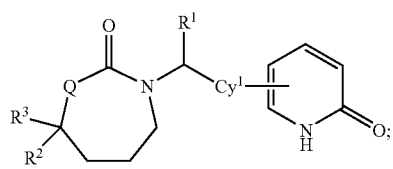

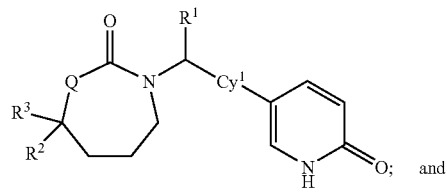

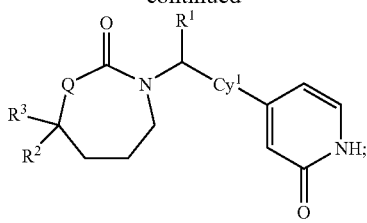

or a pharmaceutically acceptable salt, enantiomer or diastereomer thereof, wherein the oxodihydropyridyl group is optionally substituted with up to four substitutents selected from fluorine, chlorine, bromine, iodine, cyano, nitro, amino, hydroxy, carboxy, $(C_1-C_6)$alkyl, hydroxy $(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo $(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_1-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy $(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl.

49. The method of claim 47, wherein the compound is represented by a structural formula selected from:

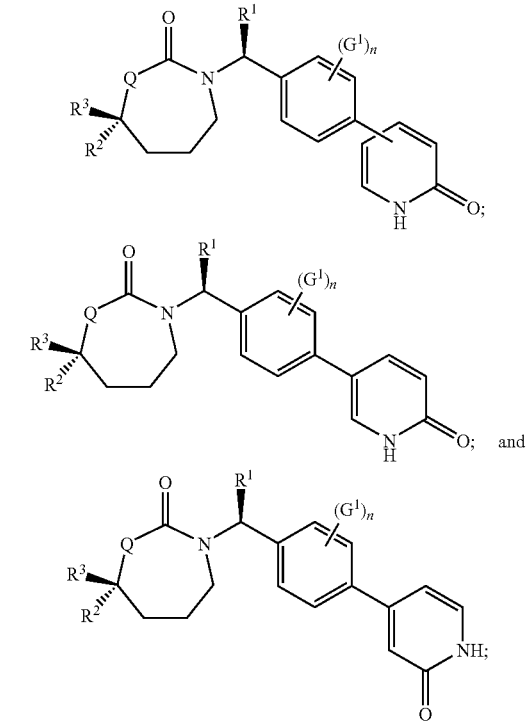

or a pharmaceutically acceptable salt, enantiomer or diastereomer thereof, wherein:

n is 0, 1, 2, or 3;

each $G^1$ is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkyl-aminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $C_6$)alkylsulfonylamino$(C_1-C_6)$alkyl, $(C_1-C_6)$alkoxycarbonyl$(C_1-C_6)$alkoxy, $(C_1-C_6)$alkoxy$(C_1-$ $C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, $C_6$)alkylamino($C_2$-$C_6$)alkoxy, di($C_1$-$C_6$)alkylamino($C_2$-$C_6$)alkoxyl and ($C_1$-$C_6$)alkylcarbonyl; and the oxodihydropyridyl group is optionally substituted with up to four substitutents selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkane-sulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl.

50. The method of claim 26, wherein the compound is represented by a structural formula selected from:

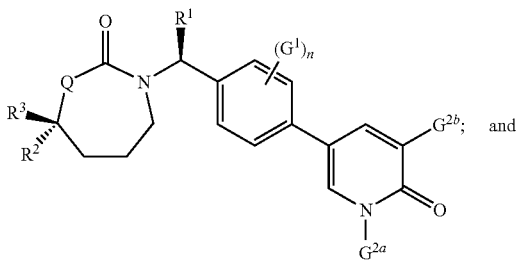

-continued

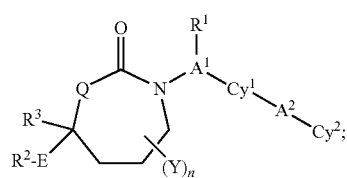

or a pharmaceutically acceptable salt thereof, wherein: $G^1$ is ($C_1$-$C_4$)alkyl, ($C_1$-$C_4$)alkoxy, ($C_1$-$C_4$)haloalkyl, ($C_1$-$C_4$)haloalkoxy, halogen, cyano or nitro; n is 0, 1 or 2; $G^{2a}$ is ($C_1$-$C_4$)alkyl, ($C_3$-$C_4$)cycloalkyl or ($C_1$-$C_4$)haloalkyl; $G^{2b}$ is hydrogen, fluorine, chlorine, cyano, hydroxy, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, $CONH_2$, ($C_1$-$C_4$)alkylaminocarbonyl, di($C_1$-$C_4$)alkylaminocarbonyl or ($C_1$-$C_4$)alkylcarbonylamino; Q is O or NH; $R^1$ is methyl or ethyl; $R^2$ is phenyl optionally substituted with 1, 2 or 3 substituents selected from halo, cyano, $CONH_2$, ($C_1$-$C_4$)alkyl, ($C_1$-$C_4$)haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

51. A pharmaceutical composition comprising: i) a pharmaceutically acceptable carrier or diluent; and ii) a compound of Formula (I)

I wherein $R^1$ is (a) absent or (b) is selected from ($C_1$-$C_6$)alkyl, ($C_2$-$C_6$)alkenyl, ($C_2$-$C_6$)alkynyl, ($C_1$-$C_3$)alkoxy($C_1$-$C_3$)alkoxy or ($C_1$-$C_3$)alkoxy($C_1$-$C_3$)alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4OC(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$A^1$ is (a) a bond, or (b) ($C_1$-$C_3$)alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkyl-carbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$A^2$ is (a) a bond, O, S or $NR^4$; or (b) ($C_1$-$C_3$)alkylene or ($C_1$-$C_2$)alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

Y is ($C_1$-$C_6$)alkyl or halo($C_1$-$C_6$)alkyl;

n is 0, 1 or 2;

E is (a) a bond or (b) ($C_1$-$C_3$)alkylene or ($C_1$-$C_2$)alkylenyloxy, wherein the 0 is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, and ($C_1$-$C_3$)alkoxy($C_1$-$C_3$)alkyl, wherein each is optionally substituted with up to four groups independently selected from fluorine, cyano, oxo, $R^4$, $R^4$O—, $(R^4)_2$N—, $R^4$$O_2$C—, $R^4$C(=O)O—, $R^4$S, $R^4$S(=O)—, $R^4$S(=O)$_2$—, $R^4$C(=O)$NR^4$, $(R^4)_2$NC(=O)—, $(R^4)_2$NC(=O)O—, $(R^4)_2$NC(=O)$NR^4$—, $R^4$OC(=O)$NR^4$—, $(R^4)_2$NC(=NCN)$NR^4$, $(R^4O)_2$P(=O)O—, $(R^4O)_2$P(=O)$NR^4$—, $R^4$OS(=O)$_2$$NR^4$, $(R^4)_2$NS(=O)$_2$O, $(R^4)_2$NS(=O)$_2$$NR^4$, $R^4$S(=O)$_2$ $NR^4$—, $R^4$S(=O)$_2$NHC(=O)—, $R^4$S(=O)$_2$NHC(=O)O—, $R^4$S(=O)$_2$NHC(=O)$NR^4$, $R^4$OS(=O)$_2$NHC(=O)—, $R^4$OS(=O)$_2$NHC(=O)O—, $R^4$OS(=O)$_2$NHC(=O)$NR^4$, $(R^4)_2$NS(=O)$_2$NHC(=O)—, $(R^4)_2$NS(=O)$_2$NHC(=O)O—, $(R^4)_2$NS(=O)$_2$NHC(=O)$NR^4$, $R^4$C(=O)NHS(=O)$_2$—, $R^4$C(=O)NHS(=O)$_2$O—, $R^4$C(=O)NHS(=O)$_2$$NR^4$, $R^4$OC(=O)NHS(=O)$_2$—, $R^4$OC(=O)NHS(=O)$_2$O—, $R^4$OC(=O)NHS(=O)$_2$$NR^4$, $(R^4)_2$NC(=O)NHS(=O)$_2$—, $(R^4)_2$NC(=O)NHS(=O)$_2$O—, $(R^4)_2$NC(=O)NHS(=O)$_2$$NR^4$, spirocycloalkyl; heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

Q is O or $NR^5$;

$R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

$R^5$ is H, ($C_1$-$C_6$)alkyl, halo($C_1$-$C_6$)alkyl, or hydroxy($C_1$-$C_6$)alkyl;

or a pharmaceutically acceptable salt, enantiomer or diastereomer thereof.

52. The pharmaceutical composition of claim 51, wherein $R^1$ is (a) absent or (b) is selected from ($C_1$-$C_6$)alkyl, ($C_2$-$C_6$)alkenyl, ($C_2$-$C_6$)alkynyl or ($C_1$-$C_3$)alkoxy($C_1$-$C_3$)alkyl, wherein each is optionally substituted with up to four groups independently selected from fluorine, cyano, oxo, $R^4$, $R^4$O—, $(R^4)_2$N—, $R^4$$O_2$C—, $R^4$S, $R^4$S(=O)—, $R^4$S(=O)$_2$—, $R^4$C(=O)$NR^4$—, $(R^4)_2$NC(=O)—, $(R^4)_2$NC(=O)O—, $(R^4)_2$NC(=O)$NR^4$—, $R^4$OC(=O)$NR^4$—, $(R^4)_2$NC(=NCN)$NR^4$—, $(R^4O)_2$P(=O)O—, $(R^4O)_2$P(=O)$NR^4$—, $R^4$OS(=O)$_2$$NR^4$—, $(R^4)_2$NS(=O)$_2$O—, $(R^4)_2$NS(=O)$_2$$NR^4$—, $R^4$S(=O)$_2$ $NR^4$—, $R^4$S(=O)$_2$NHC(=O)—, $R^4$S(=O)$_2$NHC(=O)O—, $R^4$S(=O)$_2$NHC(=O)$NR^4$—, $R^4$OS(=O)$_2$NHC(=O)—, $R^4$OS(=O)$_2$NHC(=O)O—, $R^4$OS(=O)$_2$NHC(=O)$NR^4$—, $(R^4)_2$NS(=O)$_2$NHC(=O)—, $(R^4)_2$NS(=O)$_2$NHC(=O)O—, $(R^4)_2$NS(=O)$_2$NHC(=O)$NR^4$—, $R^4$C(=O)NHS(=O)$_2$—, $R^4$C(=O)NHS(=O)$_2$O—, $R^4$C(=O)NHS(=O)$_2$$NR^4$—, $R^4$OC(=O)NHS(=O)$_2$—, $R^4$OC(=O)NHS(=O)$_2$O—, $R^4$OC(=O)NHS(=O)$_2$$NR^4$—, $(R^4)_2$NC(=O)NHS(=O)$_2$—, $(R^4)_2$NC(=O)NHS(=O)$_2$O—, $(R^4)_2$NC(=O)NHS(=O)$_2$$NR^4$—, aryl, cycloalkyl, heterocyclyl, heteroaryl, arylamino and heteroarylamino;

$A^1$ is (a) a bond, or (b) ($C_1$-$C_3$)alkylene, $CH_2CH_2O$, wherein the oxygen is attached to $Cy^1$, or $CH_2C$(=O), wherein the carbonyl carbon is attached to $Cy^1$;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

$A^2$ is (a) a bond, O, S or $NR^4$; or (b) ($C_1$-$C_3$)alkylene or ($C_1$-$C_2$)alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

Y is ($C_1$-$C_6$)alkyl or halo($C_1$-$C_6$)alkyl;

n is 0, 1 or 2;

E is (a) a bond or (b) ($C_1$-$C_3$)alkylene or ($C_1$-$C_2$)alkylenyloxy, wherein the O is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

$R^3$ is selected from ($C_1$-$C_6$)alkyl, ($C_2$-$C_6$)alkenyl, ($C_2$-$C_6$) alkynyl and ($C_1$-$C_3$)alkoxy($C_1$-$C_3$)alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4$, $(R^4O)_2P(=O)O-$, $(R^4O)_2P(=O)NR^4-$, $R^4OS(=O)_2NR^4$, $(R^4)_2NS(=O)_2O$, $(R^4)_2NS(=O)_2NR^4$, $R^4S(=O)_2NR^4-$, $R^4S(=O)_2NHC(=O)-$, $R^4S(=O)_2NHC(=O)O-$, $R^4S(=O)_2NHC(=O)NR^4$, $R^4OS(=O)_2NHC(=O)-$, $R^4OS(=O)_2NHC(=O)O-$, $R^4OS(=O)_2NHC(=O)NR^4$, $(R^4)_2NS(=O)_2NHC(=O)-$, $(R^4)_2NS(=O)_2NHC(=O)O-$, $(R^4)_2NS(=O)_2NHC(=O)NR^4$, $R^4C(=O)NHS(=O)_2-$, $R^4C(=O)NHS(=O)_2O-$, $R^4C(=O)NHS(=O)_2NR^4$, $R^4OC(=O)NHS(=O)_2-$, $R^4OC(=O)NHS(=O)_2O-$, $R^4OC(=O)NHS(=O)_2NR^4$, $(R^4)_2NC(=O)NHS(=O)_2-$, $(R^4)_2NC(=O)NHS(=O)_2O-$, $(R^4)_2NC(=O)NHS(=O)_2NR^4$, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

Q is O or $NR^5$;

$R^4$ is independently selected from H, ($C_1$-$C_6$)alkyl, halo ($C_1$-$C_6$)alkyl, amino($C_1$-$C_6$)alkyl, ($C_1$-$C_6$)alkylamino (C₁-C₆)alkyl, di(C₁-C₆)alkylamino(C₁-C₆)alkyl, hydroxy(C₁-C₆)alkyl and (C₁-C₆)alkoxy(C₁-C₆)alkyl;

$R^5$ is H, (C₁-C₆)alkyl, halo(C₁-C₆)alkyl, or hydroxy(C₁-C₆)alkyl;

or a pharmaceutically acceptable salt, enantiomer or diastereomer thereof.

53. The pharmaceutical composition of claim 52, wherein the compound is of Formula (I*)

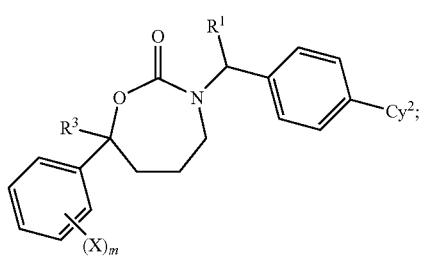

I* wherein $R^1$ is (C₁-C₆)alkyl, optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$Cy^2$ is aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₄-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkyl-alkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₁-C₆)alkoxyl and (C₁-C₆)alkylcarbonyl;

X is independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₄-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkyl-alkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl;

m is 0, 1, 2, 3, 4;

$R^3$ is (C₁-C₆)alkyl substituted with up to four groups independently selected from cyano, oxo, HO—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O-$, $R^4C(=O)NHS(=O)_2NR^4$, $R^4OC(=O)NHS(=O)_2-$, $R^4OC(=O)NHS(=O)_2O-$, $R^4OC(=O)NHS(=O)_2NR^4$, $(R^4)_2NC(=O)NHS(=O)_2-$, $(R^4)_2NC(=O)NHS(=O)_2O-$, $(R^4)_2NC(=O)NHS(=O)_2NR^4$, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo;

or a pharmaceutically acceptable salt, enantiomer or diastereomer thereof.

54. The pharmaceutical composition of claim 52, wherein the compound is of Formula (I**)

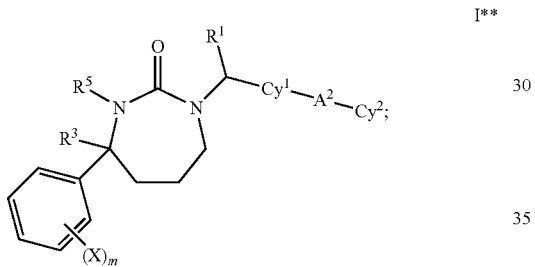

wherein $R^1$ is $(C_1-C_6)$alkyl, optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$A^2$ is a bond;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

X is independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$) cycloalkoxy, ($C_4$-$C_7$)cycloalkylalkoxy, halo($C_1$-$C_6$) alkoxy, halo($C_3$-$C_6$)cycloalkoxy, halo($C_4$-$C_7$) cycloalkylalkoxy, ($C_1$-$C_6$)alkylthio, ($C_3$-$C_6$) cycloalkylthio, ($C_4$-$C_7$)cycloalkylalkylthio, halo($C_1$-$C_6$) alkylthio, halo($C_3$-$C_6$)cycloalkylthio, halo($C_4$-$C_7$) cycloalkylalkylthio, ($C_1$-$C_6$)alkanesulfinyl, ($C_3$-$C_6$) cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$) alkanesulfonyl, ($C_3$-$C_6$)cycloalkanesulfonyl, ($C_4$-$C_7$) cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl, amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

m is 0, 1, 2, 3, 4; and $R^3$ is ($C_1$-$C_6$)alkyl substituted with up to four groups independently selected from cyano, oxo, $R^4$, HO—, $(R^4)_2$N—, $R^4O_2$C—, $R^4$S, $R^4$S($=$O)—, $R^4$S($=$O)$_2$—, $R^4$C ($=$O)$NR^4$, $(R^4)_2$NC($=$O)—, $(R^4)_2$NC($=$O)O—, $(R^4)_2$NC($=$O)$NR^4$—, $R^4$OC($=$O)$NR^4$—, $(R^4)_2$NC ($=$NCN)$NR^4$, $(R^4O)_2$P($=$O)O—, $(R^4O)_2$P($=$O) $NR^4$—, $R^4$OS($=$O)$_2$$NR^4$—, $(R^4)_2$NS($=$O)$_2$O—, $(R^4)_2$ NS($=$O)$_2$$NR^4$, $R^4$S($=$O)$_2$$NR^4$—, $R^4$S($=$O)$_2$NHC ($=$O)—, $R^4$S($=$O)$_2$NHC($=$O)O—, $R^4$S($=$O)$_2$NHC ($=$O)$NR^4$, $R^4$OS($=$O)$_2$NHC($=$O)—, $R^4$OS($=$O)$_2$ NHC($=$O)O—, $R^4$OS($=$O)$_2$NHC($=$O)$NR^4$, $(R^4)_2$NS ($=$O)$_2$NHC($=$O)—, $(R^4)_2$NS($=$O)$_2$NHC($=$O)O—, $(R^4)_2$NS($=$O)$_2$NHC($=$O)$NR^4$, $R^4$C($=$O)NHS ($=$O)$_2$—, $R^4$C($=$O)NHS($=$O)$_2$O—, $R^4$C($=$O)NHS ($=$O)$_2$$NR^4$, $R^4$OC($=$O)NHS($=$O)$_2$—, $R^4$OC($=$O) NHS($=$O)$_2$O—, $R^4$OC($=$O)NHS($=$O)$_2$$NR^4$, $(R^4)_2$ NC($=$O)NHS($=$O)$_2$—, $(R^4)_2$NC($=$O)NHS($=$O)$_2$ O—, $(R^4)_2$NC($=$O)NHS($=$O)$_2$$NR^4$, heterocyclyl which may be optionally substituted with alkyl, haloalkyl or oxo; heteroaryl which may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo; arylamino which may be optionally substituted with alkyl, alkoxy, alkylthio, alkylsulfonyl, halogen, trifluoromethyl, dialkylamino, nitro, cyano, $CO_2$H, $CONH_2$, N-monoalkyl-substituted amido and N,N-dialkyl-substituted amido; and heteroarylamino which may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo;

or a pharmaceutically acceptable salt, enantiomer or diastereomer thereof.

55. The pharmaceutical composition of claim 52, wherein $A^1$ is CH and $R^1$ is present.

56. The pharmaceutical composition of claim 55, wherein $R^1$ is unsubstituted methyl or ethyl.

57. The pharmaceutical composition of claim 52, wherein $Cy^1$ is optionally substituted phenyl.

58. The pharmaceutical composition of claim 52, wherein $R^3$ is hydroxy($C_2$-$C_4$)alkyl.

59. The pharmaceutical composition of claim 52, wherein $R^3$ is allyl.

60. The pharmaceutical composition of claim 52, wherein $R^2$ is optionally substituted phenyl.

61. The pharmaceutical composition of claim 52, wherein E is a bond.

62. The pharmaceutical composition of claim 52, wherein $R^2$ is fluorophenyl.

63. The pharmaceutical composition of claim 52, wherein $R^1$ is absent or is methyl or ethyl;

$A^1$ is a bond or $CH_2$ or if $R^1$ is present, then $A^1$ is CH;

$Cy^1$ is phenyl, cyclopropyl, cyclohexyl, pyrrolidinyl, pyridyl, N-oxo-pyridyl, thiazolyl or pyrimidinyl each optionally substituted with 1 to 4 groups independently selected from halo, methyl, trifluoromethyl, hydroxy, methoxy, methoxycarbonyl, carboxy, ethoxycarbonylmethoxy 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;

$A^2$ is a bond, O, $OCH_2$CO or C$=$O;

$Cy^2$ is (a) hydrogen or (b) phenyl, thienyl, pyridyl, N-oxopyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl each optionally substituted by 1 to 4 groups independently selected fromaminomethyl, 1-aminoethyl, halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

n is 0;

E is a bond or $CH_2$;

$R^2$ is cyclohexyl, isopropyl, thienyl, phenyl or pyridyl, each optionally substituted with one group selected from halo, methyl, methylthio or (4-morpholino)methyl;

$R^3$ is methyl, ethyl, propyl, butyl, vinyl, allyl or ethoxyethyl, each optionally substituted with up to two groups independently selected from methyl, $H_2$C$=$CH, HO—, MeO—, MeC($=$O), $H_2$N—, MeC($=$O)NH—, MeS ($=$O)$_2$NH—, $H_2$NC($=$O)—, MeNHC($=$O)—, $HO_2$C—, HO—($CH_2$)$_2$O—, (HO)$_2$P($=$O)O—, $H_2$NS ($=$O)$_2$O—, $H_2$NS($=$O)$_2$NH—, MeNHC($=$O)NH—, MeNHC($=$O)O—, cyano, $HO_2$C—, HOCH₂CH₂NH—, 4-morpholino, HOCH₂C(=O)NH—, H₂NCH₂C(=O)NH—, EtNHC(=O)NH, H₂NHC(=O)NH, H₂NHC(=O)O—, CH₃C(=O)—, MeOC(=O)NH—, MeNHC(=NC=N)NH—, Me-, MeS-, MeSO₂—, MeSO₂N(Me)—, MeS(=O)₂NHC(=O)—, imidazolylamino-, imidazolyl, morpholino, tetrazolyl, H₂NCONH—, H₂NCO₂—, HOCH₂CH₂O—, MeNH—, Me₂N— and MeCONMe; and R⁵ is hydrogen or methyl.

64. The pharmaceutical composition of claim 52, wherein the compound is of Formula (Ia)

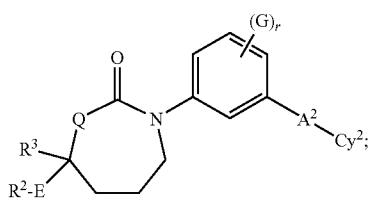

Ia wherein r is 0, 1, 2, 3 or 4; and

G is independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₁-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, amino(C₁-C₆)alkyl, (C₁-C₆)alkylamino(C₁-C₆)alkyl, di(C₁-C₆)alkylamino(C₁-C₆)alkyl, amino(C₂-C₆)alkoxy, (C₁-C₆)alkylamino(C₂-C₆)alkoxy, di(C₁-C₆)alkylamino(C₂-C₆)alkoxyl or (C₁-C₆)alkylcarbonyl;

or a pharmaceutically acceptable salt, enantiomer or diastereomer thereof.

65. The pharmaceutical composition of claim 52, wherein the compound is of Formula (Ib)

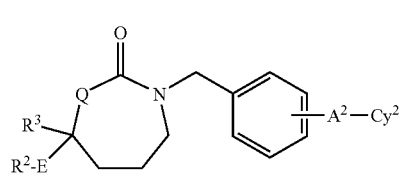

Ib or a pharmaceutically acceptable salt, enantiomer or diastereomer thereof.

66. The pharmaceutical composition of claim 52, wherein the compound is of Formula (Ic)

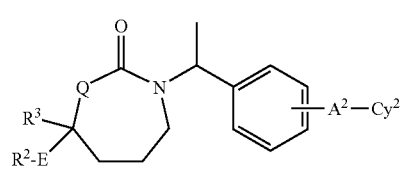

Ic or a pharmaceutically acceptable salt, enantiomer or diastereomer thereof.

67. The pharmaceutical composition of claim 52, wherein the compound is of Formula (Id)

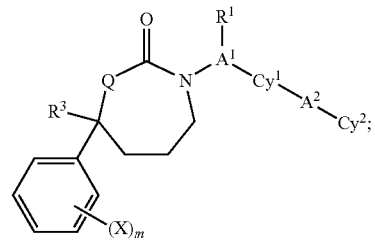

Id wherein m is 0, 1, 2, 3 or 4;

X is independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(Q-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₄-C₇)cycloalkylalkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkyl-alkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)

alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy(Q-$C_6$)alkyl, halo($C_1$-$C_6$)alkoxy($C_1$-$C_6$)alkyl, hydroxy($C_1$-$C_6$)alkoxy, heteroaryl, amino(Q-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

68. The pharmaceutical composition of claim 52, wherein the compound is of Formula (Ie)

Ie wherein r is 0, 1, 2, 3 or 4;

G is independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, (Q-$C_6$)alkoxy, ($C_3$-$C_6$)cycloalkoxy, ($C_4$-$C_7$)cycloalkylalkoxy, halo(Q-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

69. The pharmaceutical composition of claim 52, wherein the compound is of Formula (If)

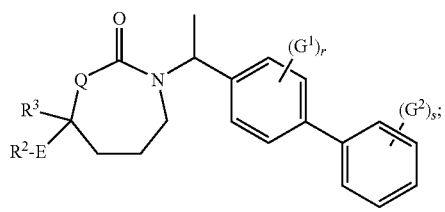

If wherein r and s are independently 0, 1, 2, 3 or 4; and $G^1$ and $G^2$ are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkyl-aminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

70. The pharmaceutical composition of claim 52, wherein the compound is of Formula (Ig)

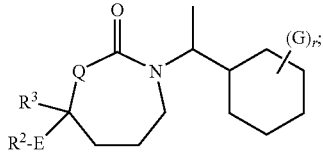

wherein
r is 0, 1, 2, 3 or 4; and
G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkyl-aminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;
or a pharmaceutically acceptable salt, enantiomer or diastereomer thereof.

71. The pharmaceutical composition of claim 52, wherein the compound is represented one of the following structural formulas:

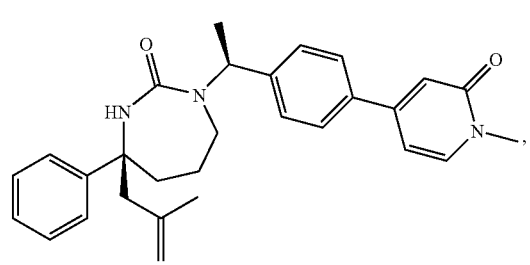

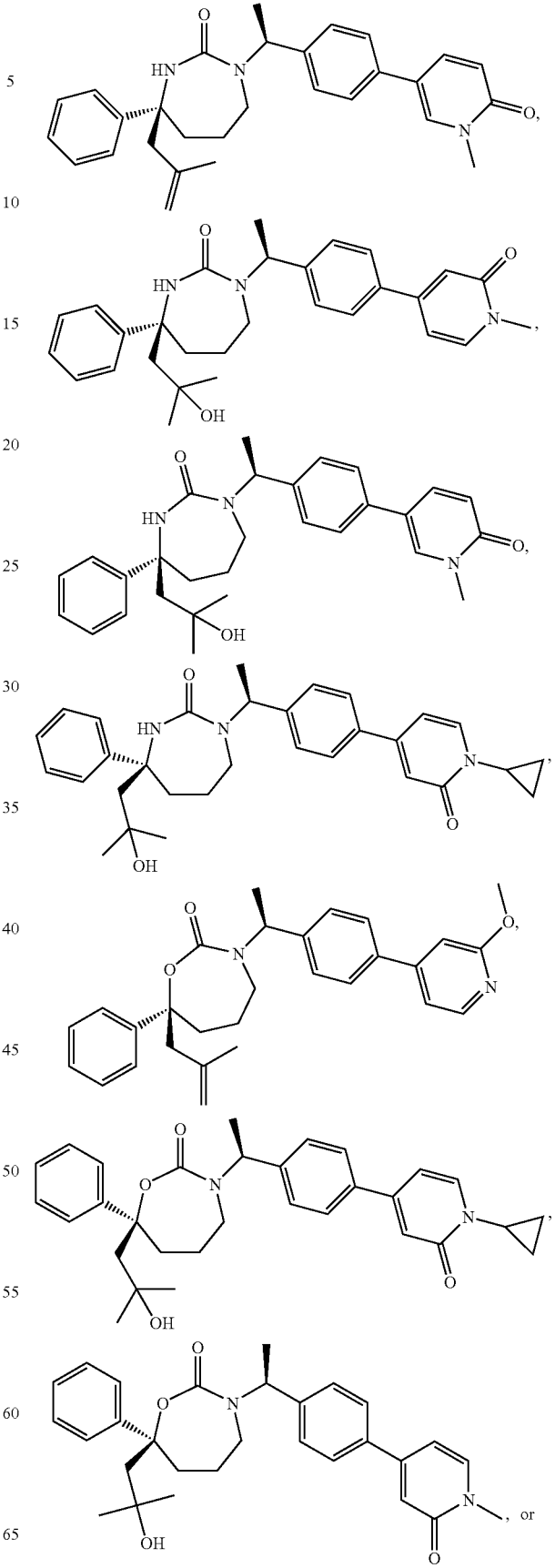

-continued

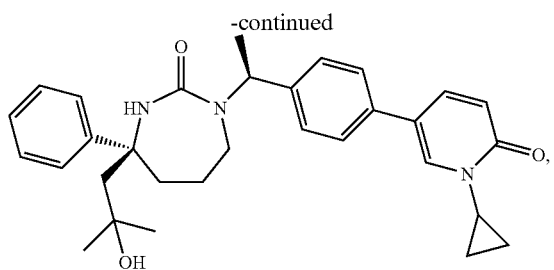

or a pharmaceutically acceptable salt, enantiomer or diastereomer thereof.

72. The pharmaceutical composition of claim 51, wherein the compound is represented by a structural formula selected from:

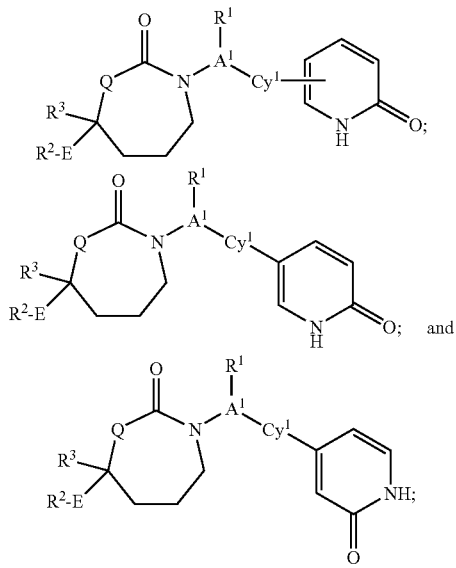

or a pharmaceutically acceptable salt, enantiomer or diastereomer thereof, wherein the oxodihydropyridyl group is optionally substituted with up to four substitutents selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, amino$(C_2-C_6)$alkoxy, $(C_1-C_6)$alkylamino$(C_2-C_6)$alkoxy, di$(C_1-C_6)$alkylamino$(C_2-C_6)$alkoxyl, $(C_1-C_6)$alkylcarbonyl, $(C_3-C_6)$cycloalkylcarbonyl, $(C_3-C_6)$cycloalkylaminocarbonyl, $\{(C_3-C_6)\text{cycloalkyl}\}\{(C_1-C_6)\text{alkyl}\}$aminocarbonyl, di$(C_3-C_6)$cycloalkylaminocarbonyl, $(C_3-C_6)$cycloalkylaminosulfonyl, $\{(C_3-C_6)\text{cycloalkyl}\}\{(C_1-C_6)\text{alkyl}\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_1-C_6)$cycloalkylaminocarbonyl$(C_1-C_6)$alkyl, $\{(C_3-C_6)\text{cycloalkyl}\}\{(C_1-C_6)\text{alkyl}\}$aminocarbonyl$(C_1-C_6)$alkyl and di$(C_3-C_6)$cycloalkylaminocarbonyl$(C_1-C_6)$alkyl.

73. The pharmaceutical composition of claim 72, wherein the compound is represented by a structural formula selected from:

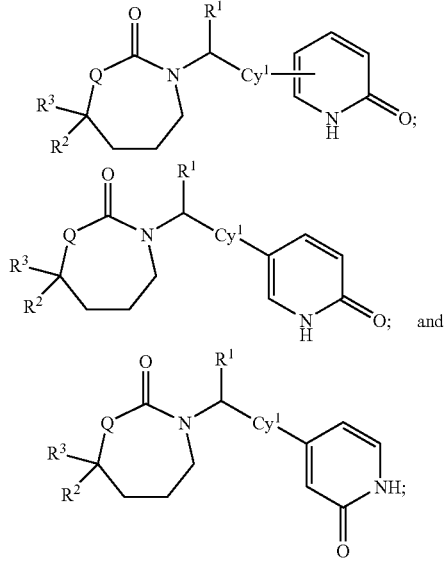

or a pharmaceutically acceptable salt, enantiomer or diastereomer thereof, wherein the oxodihydropyridyl group is optionally substituted with up to four substitutents selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$ alkylthio, (C$_3$-C$_6$)cycloalkylhio, (C$_4$-C$_7$)cycloalkylalkylthio, halo(C$_1$-C$_6$)alkylthio, halo(C$_3$-C$_6$)cycloalkylhio, halo(C$_4$-C$_7$)cycloalkylalkylthio, (C$_1$-C$_6$)alkanesulfinyl, (C$_1$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkyl-carbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl, (C$_1$-C$_6$)alkylcarbonyl, (C$_3$-C$_6$)cycloalkylcarbonyl, (C$_3$-C$_6$)cycloalkylaminocarbonyl, {(C$_3$-C$_6$)cycloalkyl}{(C$_1$-C$_6$)alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$)alkyl}aminosulfonyl, di(C$_3$-C$_6$)cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl.

74. The pharmaceutical composition of claim 72, wherein the compound is represented by a structural formula selected from:

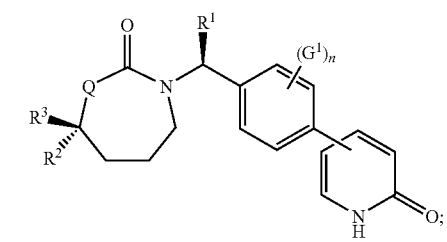

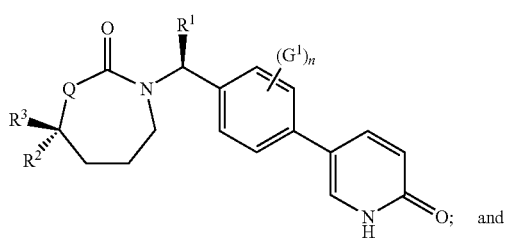

-continued

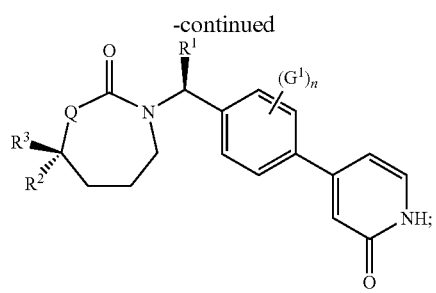

or a pharmaceutically acceptable salt, enantiomer or diastereomer thereof, wherein:

n is 0, 1, 2, or 3;

each G$^1$ is independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylhio, (C$_4$-C$_7$)cycloalkylalkylthio, halo(C$_1$-C$_6$)alkylthio, halo(C$_3$-C$_6$)cycloalkylhio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkyl-alkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkyl-aminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl and (C$_1$-C$_6$)alkylcarbonyl; and the oxodihydropyridyl group is optionally substituted with up to four substitutents selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)

alkynyl, halo(C₁-C₆)alkyl, halo(C₃-C₆)cycloalkyl; halo (C₄-C₇)cycloalkylalkyl, (C₁-C₆)alkoxy, (C₃-C₆)cycloalkoxy, (C₄-C₇)cycloalkylalkoxy, halo(C₁-C₆) alkoxy, halo(C₃-C₆)cycloalkoxy, halo(C₄-C₇) cycloalkylalkoxy, (C₁-C₆)alkylthio, (C₃-C₆) cycloalkylhio, (C₄-C₇)cycloalkylalkylthio, halo(C₁-C₆) alkylthio, halo(C₃-C₆)cycloalkylhio, halo(C₄-C₇) cycloalkylalkylthio, (C₁-C₆)alkanesulfinyl, (C₃-C₆) cycloalkanesulfinyl, (C₄-C₇)cycloalkylalkanesulfinyl, halo(C₁-C₆)alkane-sulflnyl, halo(C₃-C₆)cycloalkanesulfinyl, halo(C₄-C₇)cycloalkylalkanesulfinyl, (C₁-C₆) alkanesulfonyl, (C₃-C₆)cycloalkanesulfonyl, (C₄-C₇) cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆) alkylamino, (C₁-C₆)alkoxy(C₁-C₆)alkoxy, halo(C₁-C₆) alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy (C₁-C₆)alkyl, halo(C₁-C₆)alkoxy(C₁-C₆)alkyl, hydroxy (C₁-C₆)alkoxy, heteroaryl, oxo, amino(C₁-C₆)alkyl, (C₁-C₆)alkylamino(C₁-C₆)alkyl, di(C₁-C₆)alkylamino (C₁-C₆)alkyl, amino(C₂-C₆)alkoxy, (C₁-C₆)alkylamino (C₂-C₆)alkoxy, di(C₁-C₆)alkylamino(C₂-C₆)alkoxyl, (C₁-C₆)alkylcarbonyl, (C₃-C₆)cycloalkylcarbonyl, (C₃-C₆)cycloalkylaminocarbonyl, {(C₃-C₆)cycloalkyl}{(C₁-C₆)alkyl}aminocarbonyl, di(C₃-C₆)cycloalkylaminocarbonyl, (C₃-C₆)cycloalkylaminosulfonyl, {(C₃-C₆) cycloalkyl}{(C₁-C₆)alkyl}aminosulfonyl, di(C₃-C₆) cycloalkylaminosulfonyl, cyano(C₁-C₆)alkyl, aminocarbonyl(C₁-C₆)alkyl, (C₁-C₆)alkylaminocarbonyl(C₁-C₆)alkyl, di(C₁-C₆)alkylaminocarbonyl(C₁-C₆) alkyl, (C₃-C₆)cycloalkylaminocarbonyl(C₁-C₆)alkyl, {(C₃-C₆)cycloalkyl}{(C₁-C₆)alkyl}aminocarbonyl(C₁-C₆)alkyl and di(C₃-C₆)cycloalkylaminocarbonyl(C₁-C₆)alkyl.

75. The pharmaceutical composition of claim 51, wherein the compound is represented by a structural formula selected from:

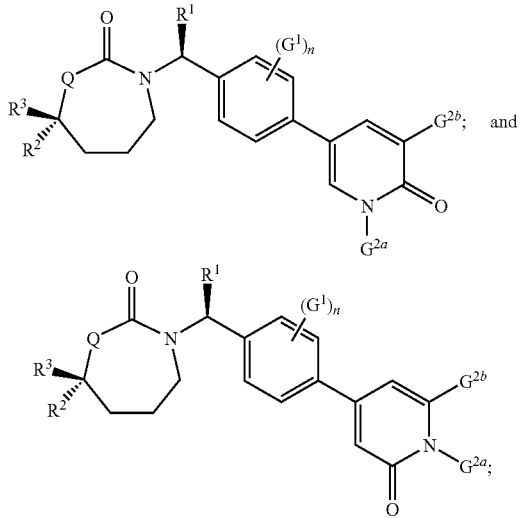

or a pharmaceutically acceptable salt thereof, wherein: $G^1$ is $(C_1-C_4)$alkyl, $(C_1-C_4)$alkoxy, $(C_1-C_4)$haloalkyl, $(C_1-C_4)$haloalkoxy, halogen, cyano or nitro; n is 0, 1 or 2; $G^{2a}$ is $(C_1-C_4)$alkyl, $(C_3-C_4)$cycloalkyl or $(C_1-C_4)$haloalkyl; $G^{2b}$ is hydrogen, fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino; Q is O or NH; $R^1$ is methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

\* \* \* \* \*